US011976296B2

(12) United States Patent
Bolognin et al.

(10) Patent No.: US 11,976,296 B2
(45) Date of Patent: May 7, 2024

(54) MEANS AND METHODS FOR GENERATING MIDBRAIN ORGANOIDS

(71) Applicant: UNIVERSITÉ DU LUXEMBOURG, Esch-sur-Alzette (LU)

(72) Inventors: Silvia Bolognin, Belvaux (LU); Anna Monzel, Belvaux (LU); Jens Schwamborn, Belvaux (LU)

(73) Assignee: UNIVERSITÉ DU LUXEMBOURG, Esch-sur-Alzette (LU)

( * ) Notice: Subject to any disclaimer, the term of this patent is extended or adjusted under 35 U.S.C. 154(b) by 642 days.

(21) Appl. No.: 15/766,779

(22) PCT Filed: Oct. 10, 2016

(86) PCT No.: PCT/IB2016/056054
§ 371 (c)(1),
(2) Date: Apr. 6, 2018

(87) PCT Pub. No.: WO2017/060884
PCT Pub. Date: Apr. 13, 2017

(65) Prior Publication Data
US 2018/0298330 A1    Oct. 18, 2018

(30) Foreign Application Priority Data
Oct. 8, 2015   (LU) .......................... 92845

(51) Int. Cl.
*C12N 5/0793*   (2010.01)
*C12N 5/079*   (2010.01)
*G01N 33/50*   (2006.01)

(52) U.S. Cl.
CPC ......... *C12N 5/0619* (2013.01); *C12N 5/0622* (2013.01); *G01N 33/5058* (2013.01); *G01N 33/5088* (2013.01); *C12N 2500/38* (2013.01); *C12N 2501/01* (2013.01); *C12N 2501/115* (2013.01); *C12N 2501/119* (2013.01); *C12N 2501/13* (2013.01); *C12N 2501/15* (2013.01); *C12N 2501/155* (2013.01); *C12N 2501/41* (2013.01); *C12N 2501/415* (2013.01); *C12N 2501/727* (2013.01); *C12N 2506/11* (2013.01); *C12N 2506/1307* (2013.01); *C12N 2506/45* (2013.01); *C12N 2513/00* (2013.01); *C12N 2533/90* (2013.01)

(58) Field of Classification Search
CPC .............. C12N 5/0619; C12N 5/0622; C12N 2500/38; C12N 2501/01; C12N 2501/115; C12N 2501/119; C12N 2501/13; C12N 2501/15; C12N 2501/155; C12N 2501/41; C12N 2501/415; C12N 2501/727; C12N 2506/11; C12N 2506/1307; C12N 2506/45; C12N 2513/00; C12N 2533/90; G01N 33/5058; G01N 33/5088

USPC ........................................ 435/1.1
See application file for complete search history.

(56) References Cited

U.S. PATENT DOCUMENTS

2015/0087541 A1   3/2015  Gonzalez et al.
2015/0330970 A1*  11/2015  Knoblich ............. C12N 5/0696
                                                  435/29

FOREIGN PATENT DOCUMENTS

| EP | 2218778 A1 | 8/2010 |
| EP | 2614829 A1 | 7/2013 |
| WO | 2009115295 A1 | 9/2009 |
| WO | 2009144008 A1 | 12/2009 |
| WO | 2013104752 A1 | 7/2013 |

OTHER PUBLICATIONS

Tieng et al. "Engineering of midbrain organoids containing long-lived dopaminergic neurons." Stem Cells and Development 23.13 (2014): 1535-1547 (Year: 2014).*
Freeman et al. "Evolving concepts of gliogenesis: a look way back and ahead to the next 25 years." Neuron 80.3 (2013): 613-623 (Year: 2013).*
International Search Report & Written Opinion issued in PCT/IB2016/056054 dated Dec. 19, 2016.
Madeline A. Lancaster, et al.; "Generation of cerebral organoids from human pluripotent stem cells"; Nature Protocols; vol. 9, No. 10; pp. 2329-2340; (Sep. 2014).
Madeline A. Lancaster, et al.; "Cerebral organoids model human brain development and microcephaly"; Nature; vol. 501, No. 7467; pp. 373-379; (Aug. 2013).
Peter Reinhardt, et al.; "Derivation and Expansion Using Only Small Molecules of Human Neural Progenitors for Neurodegenerative Disease Modeling"; PLOS ONE; vol. 8, No. 3; pp. 1-18; (Mar. 2013).
Emily Gale, et al.; "Midbrain dopaminergic neuron fate specification: Of mice and embryonic stem cells"; Molecular Brain, BioMed Central; vol. 1, No. 1; pp. 1-10; (Sep. 2008).
Marius Ader, et al.; "Modeling human development in 3D culture"; Current Opinion in Cell Biology, vol. 31, No. 1; pp. 23-28; (Dec. 2014).
Nancy Stanslowsky, et al.; "Functional differentiation of midbrain neurons from human cord blood-derived induced pluripotent stem cells"; Stem Cell Research & Therapy; vol. 5, No. 2; pp. 1-14; (Mar. 2014).

(Continued)

*Primary Examiner* — Janet L Epps-Smith
*Assistant Examiner* — Alexander W Nicol
(74) *Attorney, Agent, or Firm* — DITTHAVONG, STEINER & MLOTKOWSKI

(57) ABSTRACT

The present invention provides means and methods for the generation of midbrain organoids which are useful for studying neurodevelopmental and neurodegenerative diseases. Neuroepithelial stem cells serve as a starting population for the generation of midbrain organoids by contacting them with differentiation medium under agitating conditions in three-dimensional cell culture comprising a matrix.

14 Claims, 22 Drawing Sheets

Figure 1:
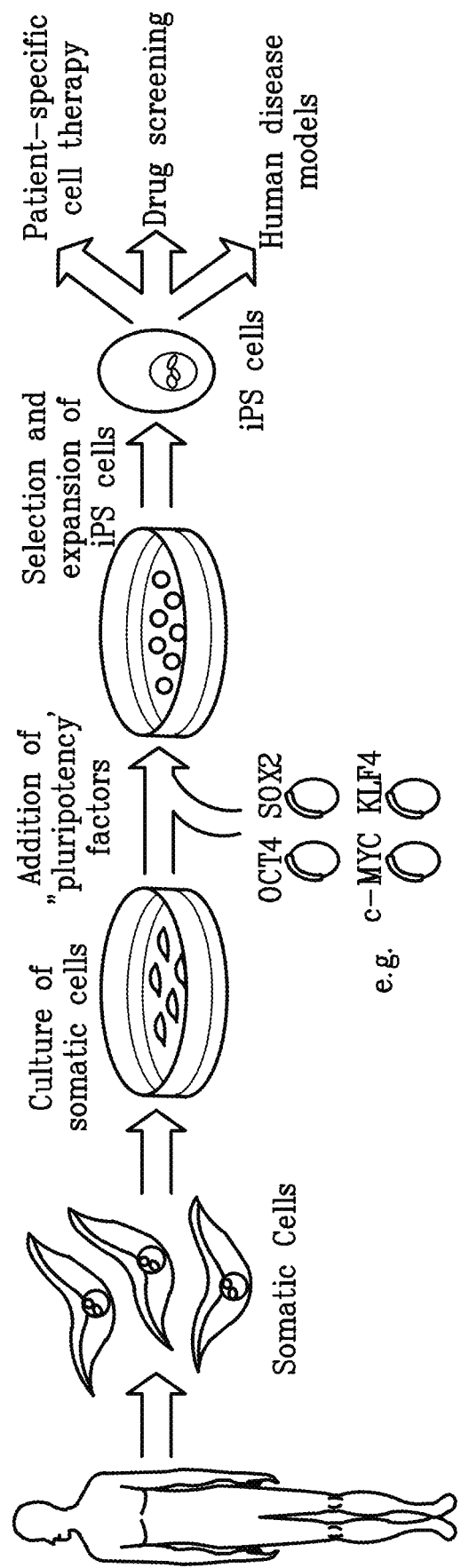

Specification includes a Sequence Listing.

(56) References Cited

OTHER PUBLICATIONS

Mototsugu Eiraku, et al.; "Self-Organized Formation of Polarized Cortical Tissues from ESCs and Its Active Manipulation by Extrinsic Signals"; Cell Stem Cell, Cell Press; vol. 3, No. 5; pp. 519-532; (Nov. 2008).
Stuart M. Chambers, et al.; "Highly efficient neural conversion of human ES and iPS cells by dual inhibition of SMAD signaling"; Nature Biotechnology; vol. 27, No. 3; pp. 275-280; (Mar. 2009).
Madeline A. Lancaster, et al.; "Organogenesis in a dish: Modeling development and disease using organoid technologies"; Science; vol. 345, No. 6194; pp. 283 & 1247125-1 through 1247125-9; (Jul. 2014).
Asa Abeliovich, et al.; "Midbrain dopamine neuron differentiation: Factors and fates"; Developmental Biology; vol. 304; pp. 447-454; (2007).
S.L. Ang; "Foxa1 and Foxa2 transcription factors regulate differentiation of midbrain dopaminergic neurons"; Advances in experimental medicine and biology; vol. 651; pp. 58-65; (2009); Abstract Only.
Cedric Bardy, et al.; "Neuronal medium that supports basic synaptic functions and activity of human neurons in vitro"; Proceedings of the National Academy of Sciences of the USA; pp. E2725-E2734; (2015).
Jeffrey L. Cummings, et al.; "Alzheimer's disease drug-development pipeline: few candidates, frequent failures"; Alzheimer's Research & Therapy; vol. 6, No. 4; pp. 1-7; (2014).
Ferran Diego, et al.; "Automated identification of neuronal activity from calcium imaging by sparse dictionary learning"; Proceedings of the IEEE 10th International Symposium on Biomedical Imaging; pp. 1058-1061; (2013); Abstract Only.
Fred H. Gage; "Mammalian Neural Stem Cells"; Science; vol. 287; pp. 1433-1438; (Feb. 2000).
Carl-Henrik Heldin, et al.; "TGF-β signalling from cell membrane to nucleus through SMAD proteins"; Nature; vol. 390; pp. 465-471; (Dec. 1997).
Tommy L. Lewis, Jr., et al.; "Cellular and molecular mechanisms underlying axon formation, growth, and branching"; The Journal of Cell Biology; vol. 202, No. 6; pp. 837-848; (2013).
Catriona Y. Logan, et al.; "The WNT Signaling Pathway in Development and Disease"; Annual Rev. Cell Dev. Biology; vol. 20; pp. 781-810; (2004).
Masato Nakagawa, et al.; "A novel efficient feeder-free culture system for the derivation of human induced pluripotent stem cells"; Scientific Reports; vol. 4, No. 3594; pp. 1-7; (2014).
Edinson Lucumi Moreno, et al.; "Differentiation of neuroepithelial stem cells into functional dopaminergic neurons in 3D microfluidic cell culture"; Royal Society of Chemistry, Lab Chip; vol. 15; pp. 2419-2428; (2015).
Hitoshi Niwa; "How is pluripotency determined and maintained?"; Development; vol. 134; pp. 635-646; (2007).
Simon A. Sharples, et al.; "Dopamine: a parallel pathway for the modulation of spinal locomotor networks"; Frontiers in Neural Circuits; vol. 8, Article 55; pp. 1-16; (Jun. 2014).
Taisuke Kadoshima, et al.; "Self-organization of axial polarity, inside-out laer pattern, and species-specific progenitor dynamics in human ES cell-derived neocortex"; Proceedings of the National Academy of Sciences of the USA; vol. 110, No. 50; pp. 20284-20289; (Dec. 2013).
Kazutoshi Takahashi, et al.; "Induction of Pluripotent Stem Cells from Mouse Embryonic and Adult Fibroblast Cultures by Defined Factors"; Cell; vol. 126; pp. 663-676; (Aug. 2006).
Kazutoshi Takahashi, et al.; "Induction of Pluripotent Stem Cells from Adult Human Fibroblasts by Defined Factors"; Cell; vol. 131; pp. 861-872; (Nov. 2007).
James A. Thomson, et al.; "Human embryonic stem cell and embryonic germ cell lines"; Trends in Biotechnology; vol. 18; pp. 53-57; (Feb. 2000).
Irving L. Weissman; "Stem Cells: Units of Development, Units of Regeneration, and Units in Evolution"; Cell; vol. 100; pp. 157-168; (Jan. 2000).
Shinya Yamanaka, et al.; "Nuclear reprogramming to a pluripotent state by three approaches"; Nature; vol. 465; pp. 704-712; (Jun. 2010).
Junying Yu, et al.; "Induced Pluripotent Stem Cell Lines Derived from Human Somatic Cells"; Science; vol. 318; pp. 1917-1920; (Dec. 2007).
Jiwang Zhang, et al.; "BMP signaling and stem cell regulation"; Developmental Biology; vol. 284; pp. 1-11; (2005).
Office Action issued in the corresponding Japanese Patent Application No. 2018-517798 dated Nov. 17, 2020.
Smits et al., "Midbrain Organoids: A New Tool to Investigate Parkinson's Disease", Frontiers in Cell and Developmental Biology, May 2020, vol. 8, Article 359, 12 pages.
Tieng et al., "Engineering of midbrain organoids containing long-lived dopaminergic neurons", Stem cells and development, 2014, vol. 23 No. 13, pp. 1535-1547.
Dono, "Fibroblast growth factors as regulators of central nervous system development and function", Am J Physiol Regul Integr Comp Physiol vol. 284, Apr. 2003, pp. R867-R881.
Beenken et al., "The FGF family: biology, pathophysiology and therapy", Nat Rev Drug Discov. Mar. 2009 ; 8(3), 42 pages.
Horner et al., "Defining the NG2-expressing cell of the adult CNS", Journal of Neurocytology 31, 2003, pp. 469-480.

\* cited by examiner

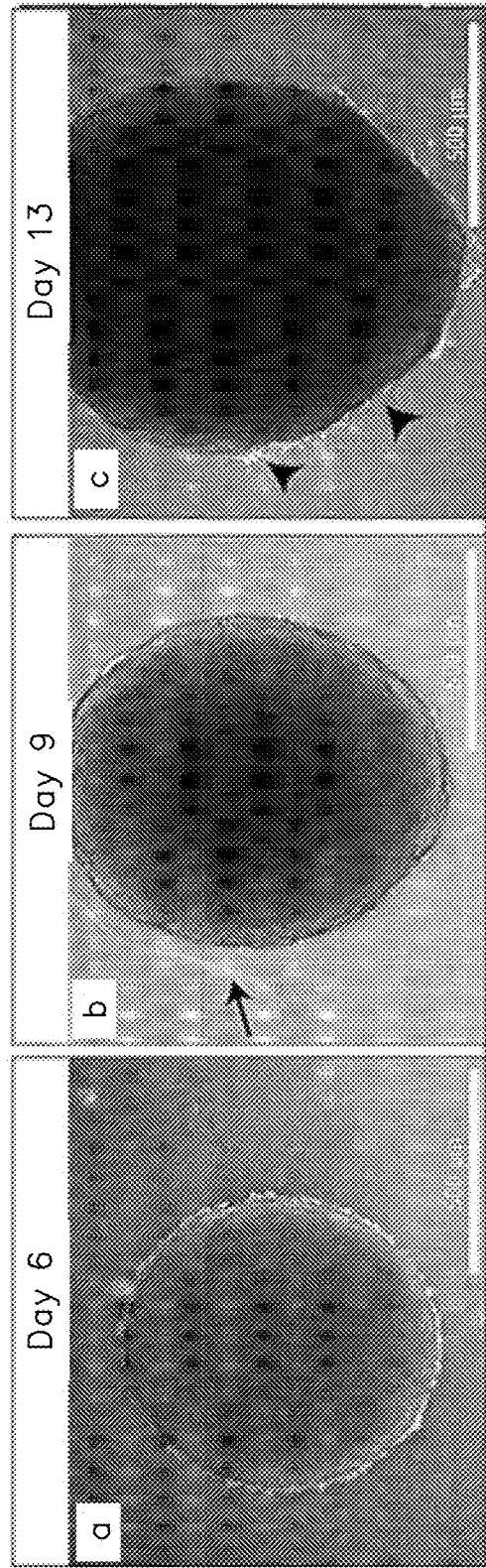
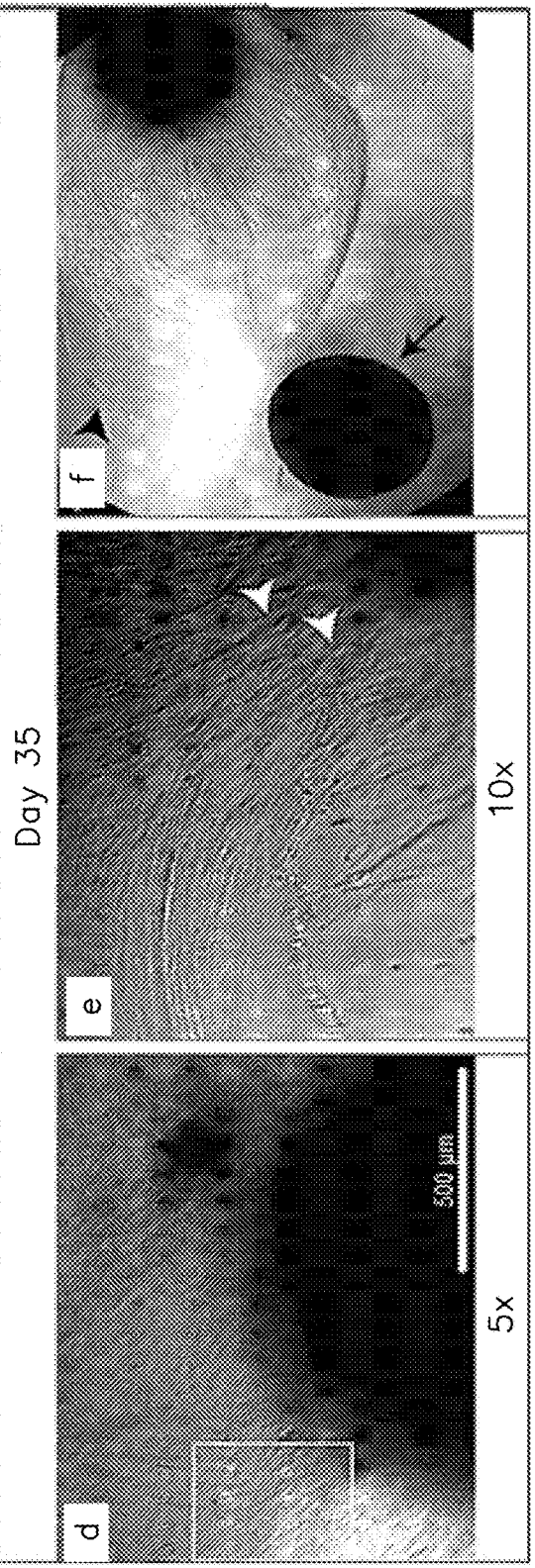

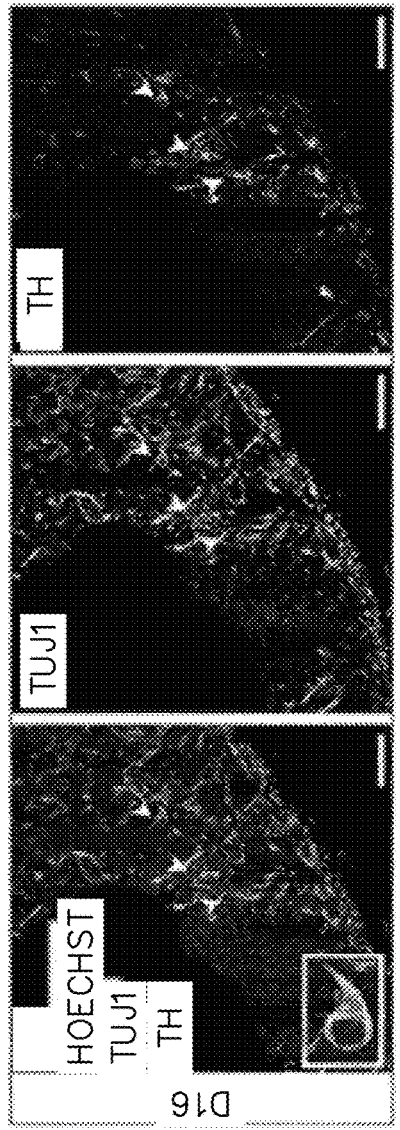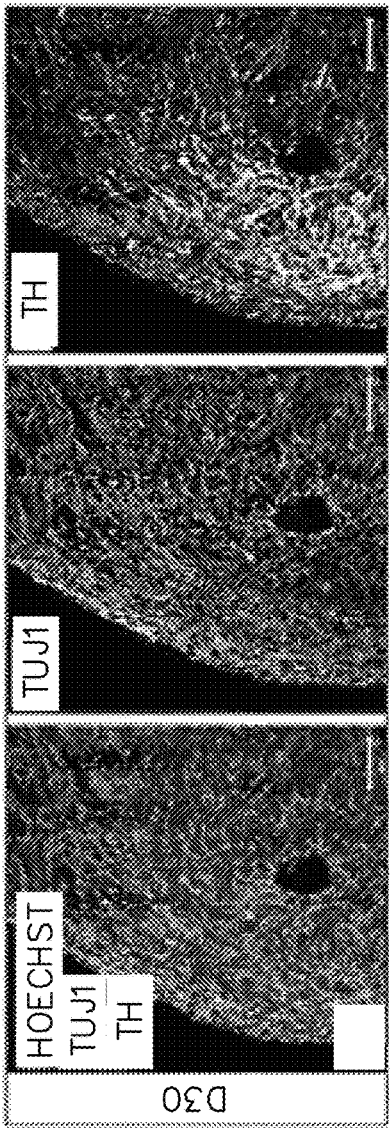

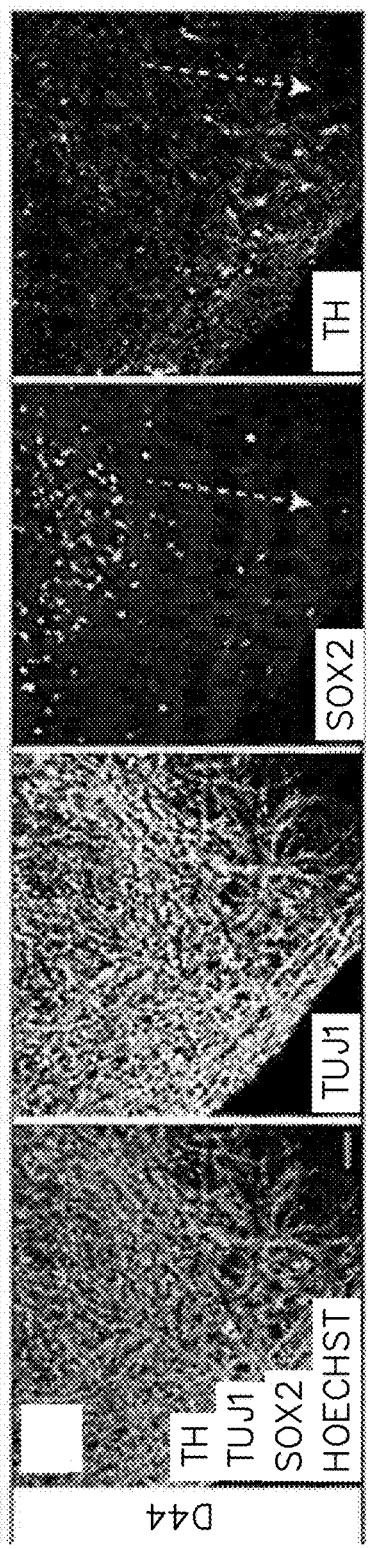

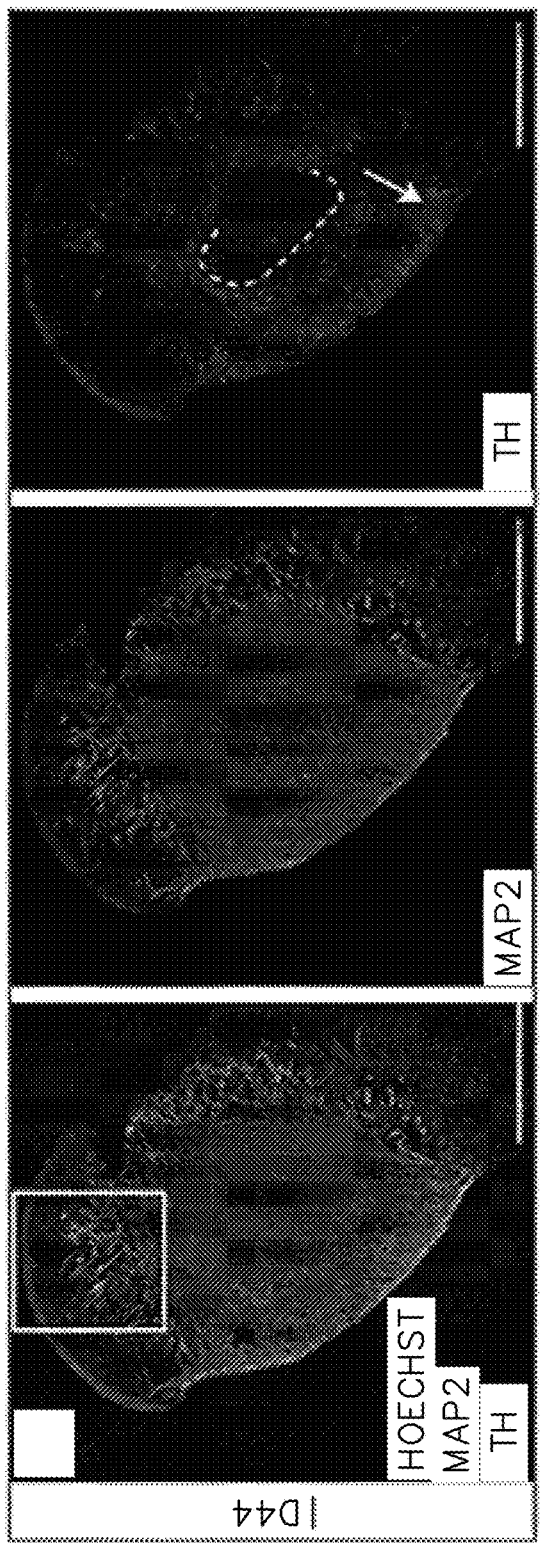
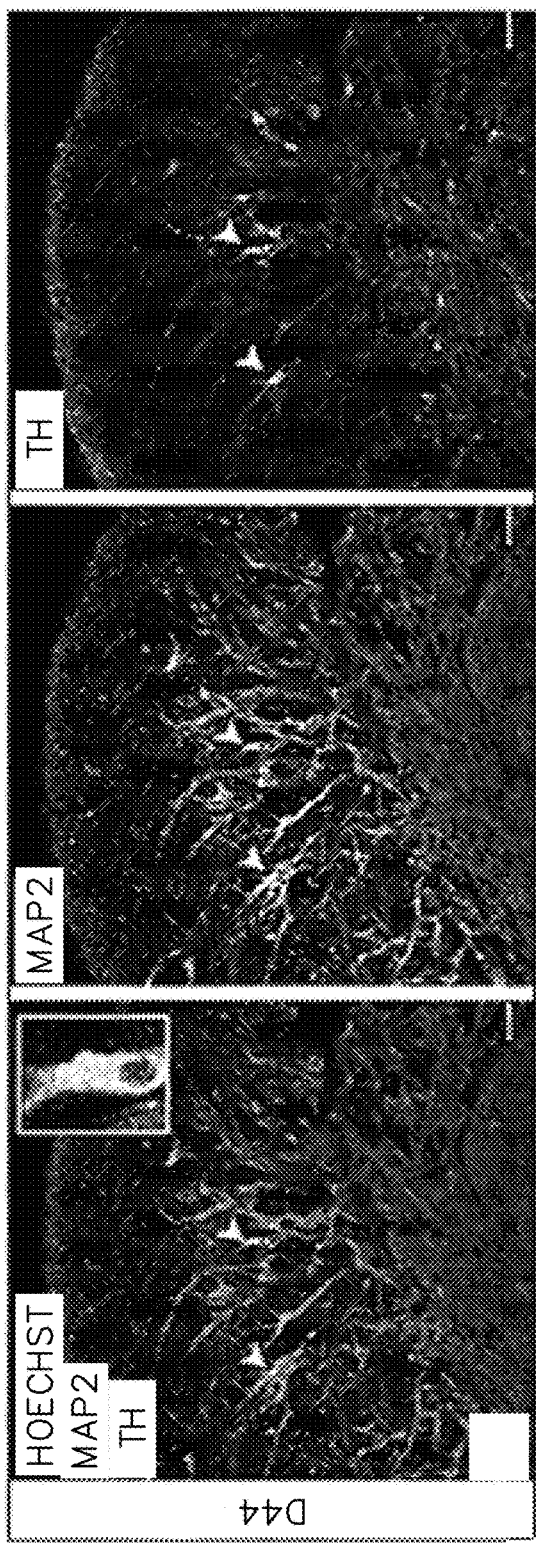
FIG. 7C
FIG. 7D

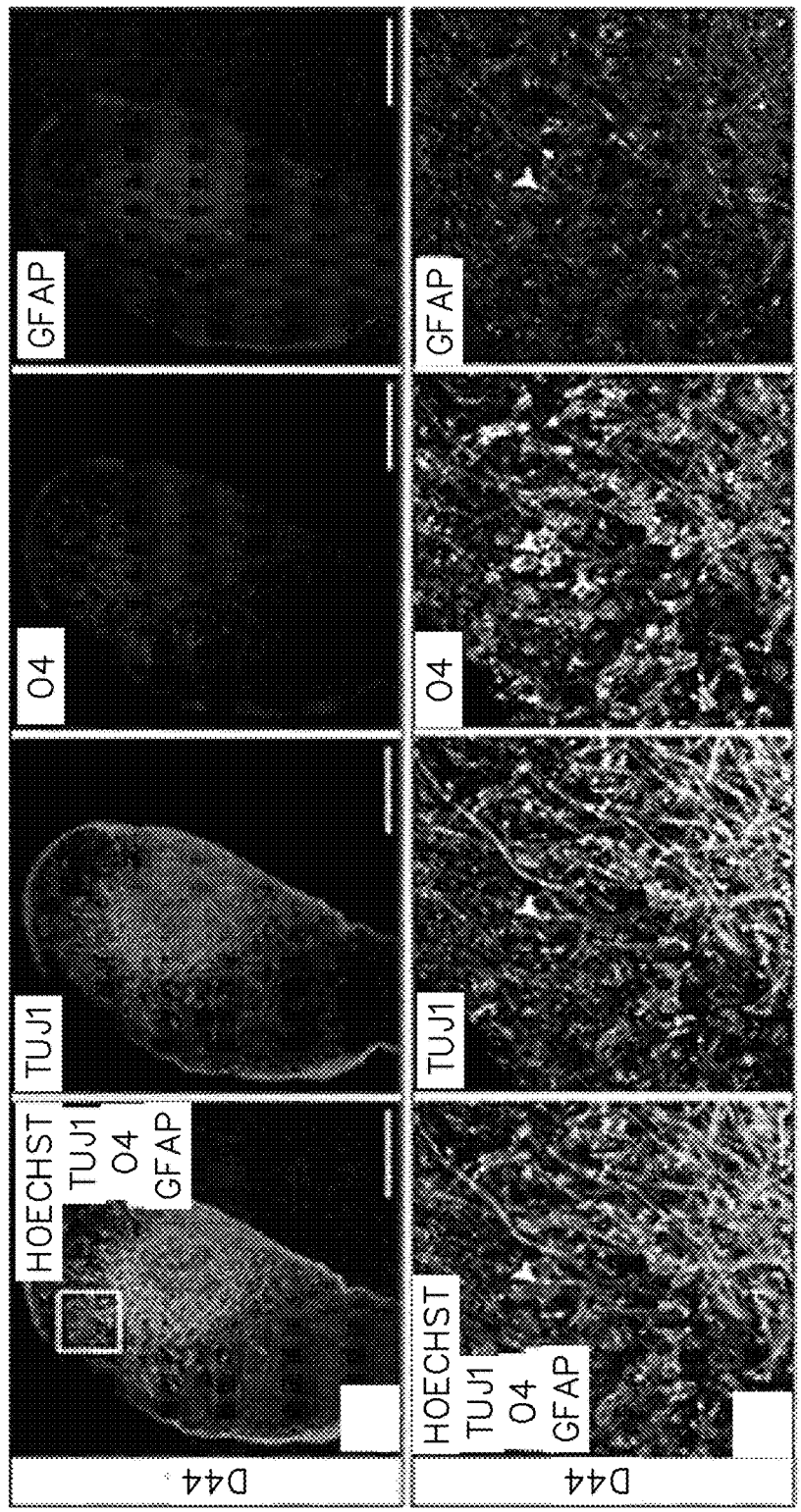

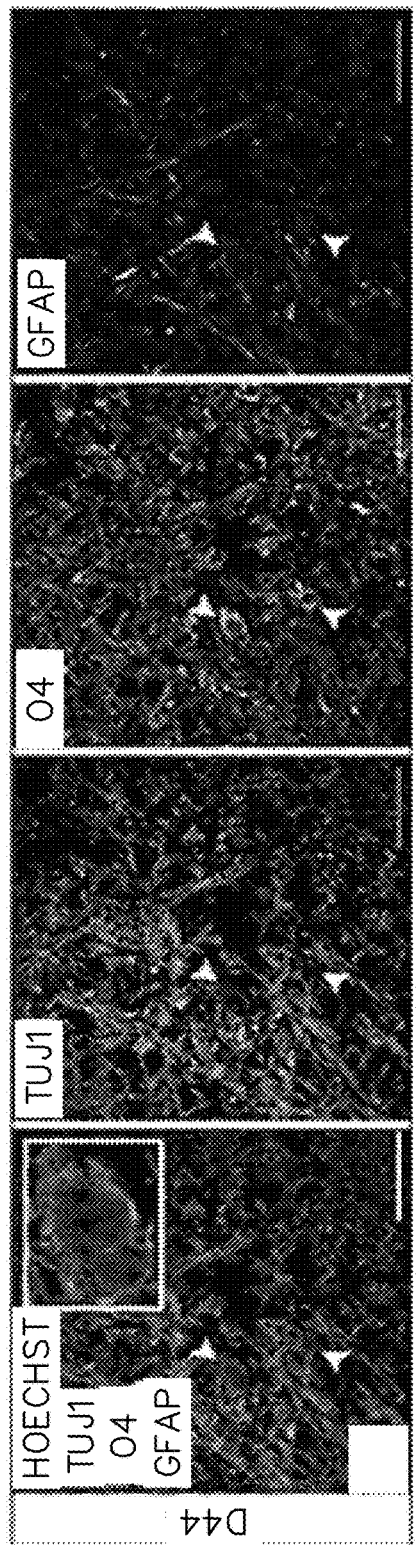
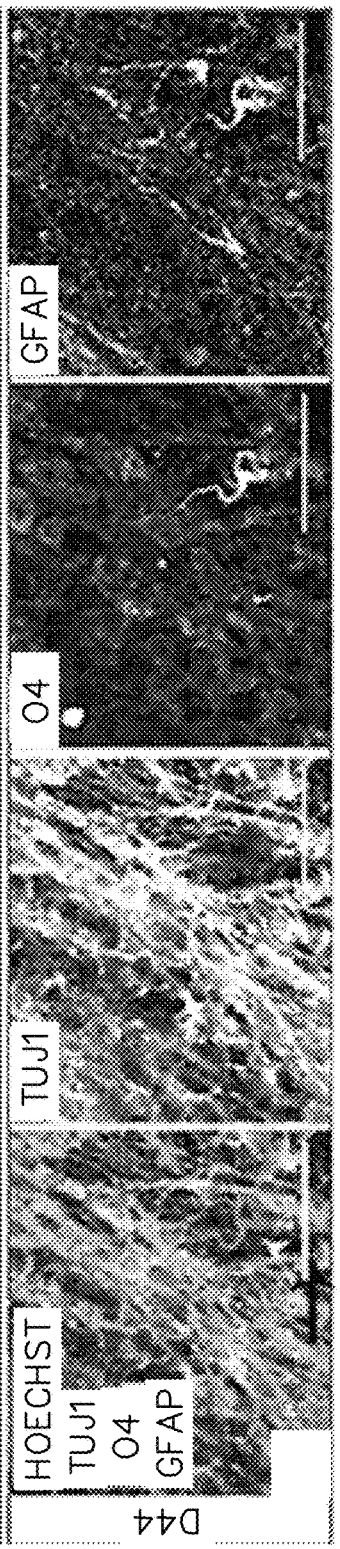
FIG. 8C
FIG. 8D

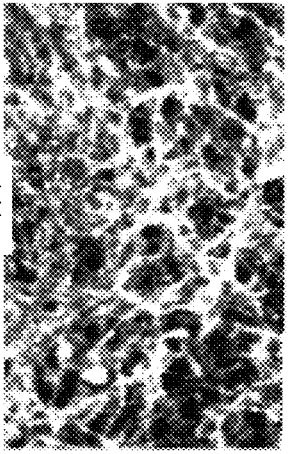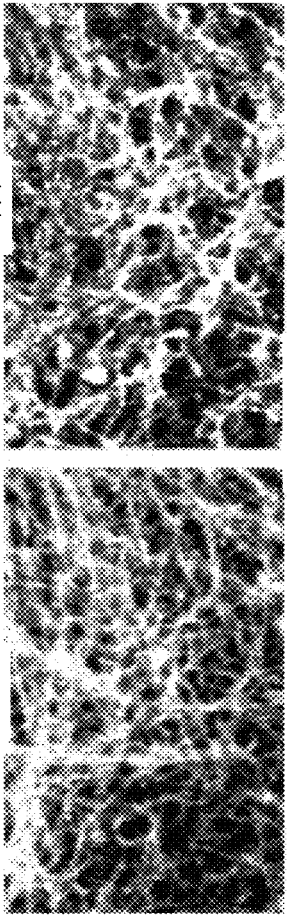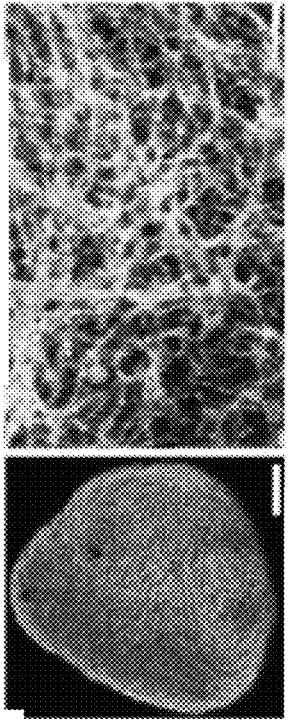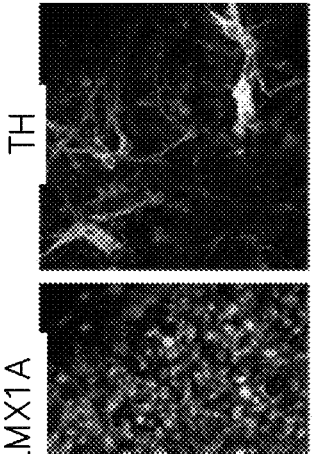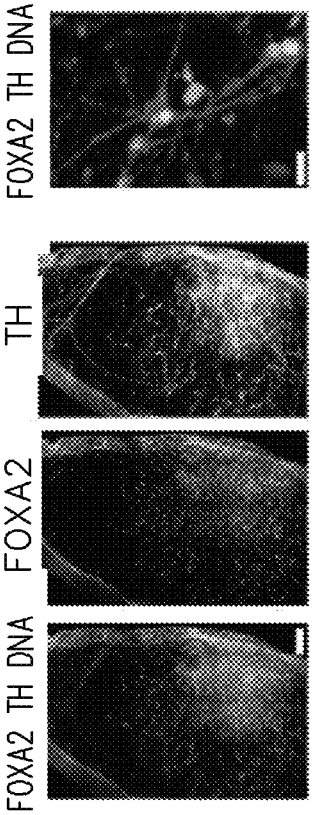
FIG. 10A FIG. 10B FIG. 10C FIG. 10D FIG. 10E

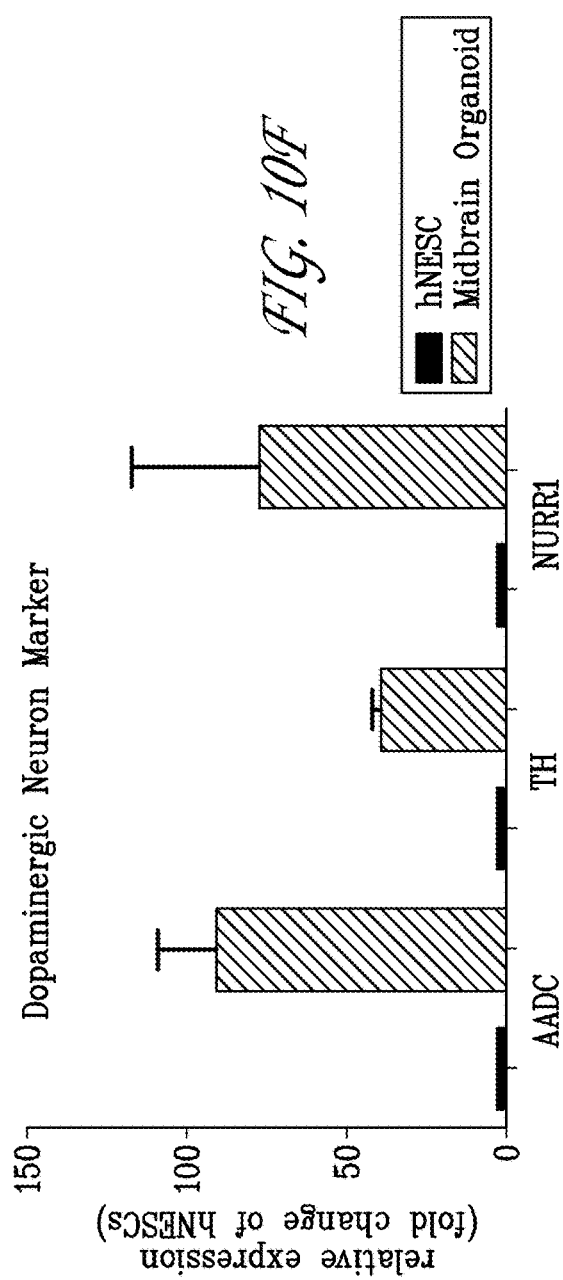
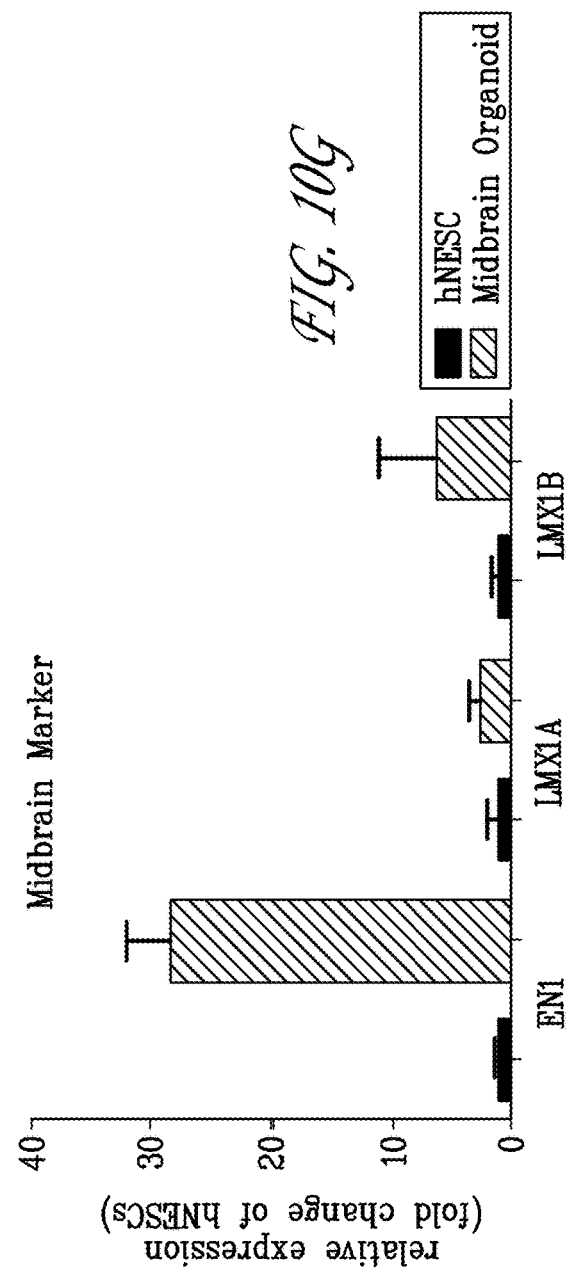
FIG. 10F
FIG. 10G

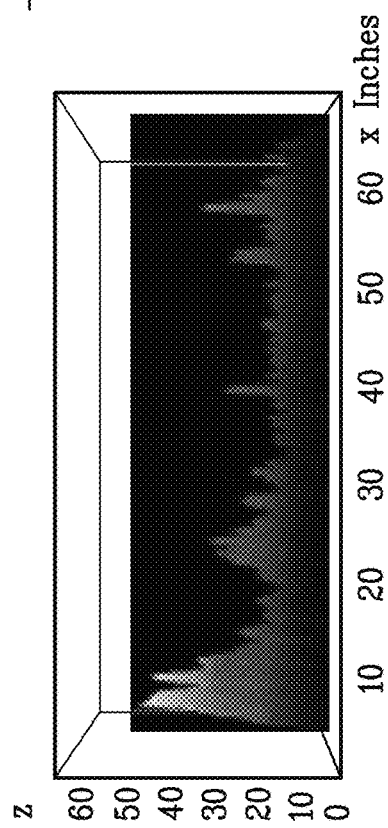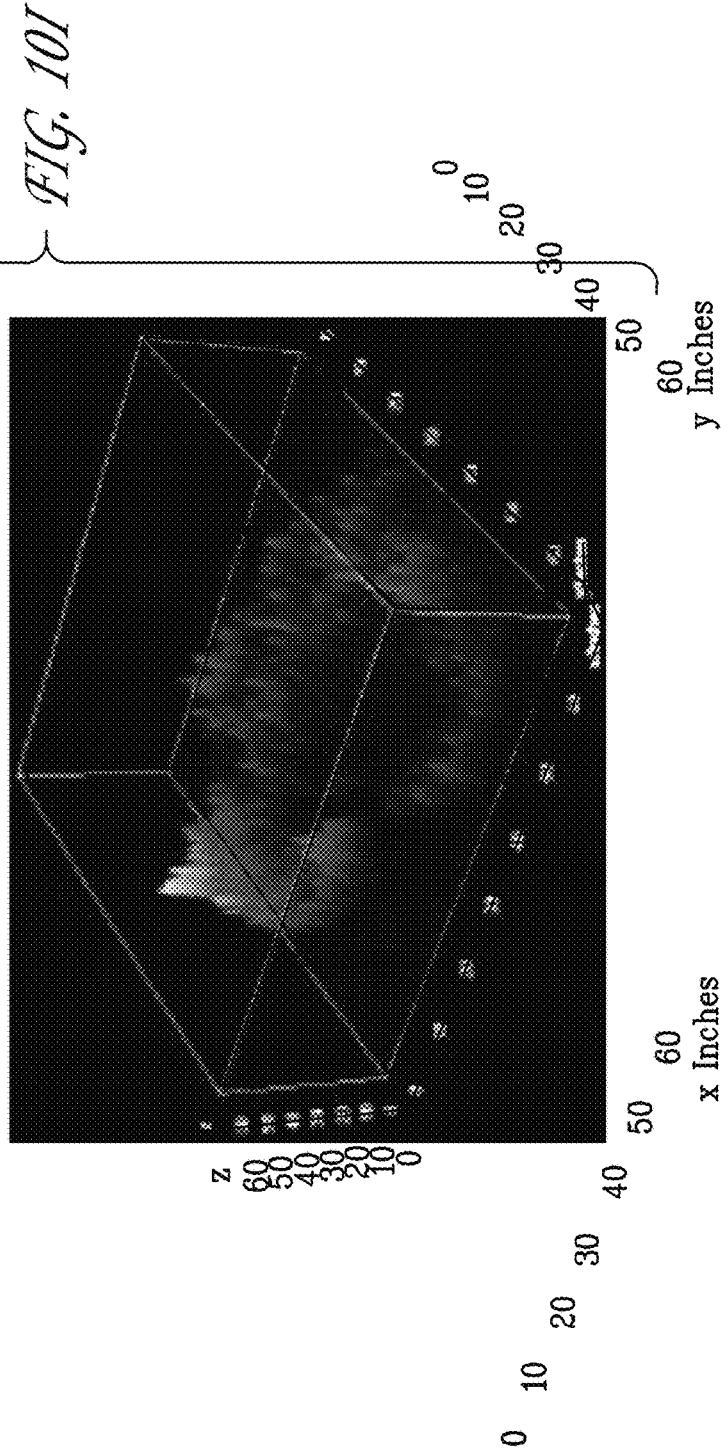
FIG. 10I

Figure 12B:
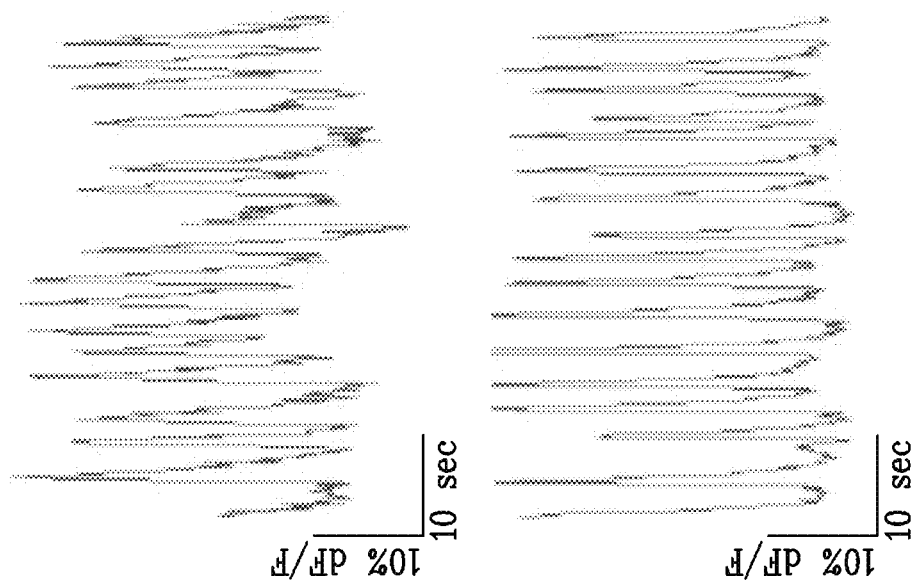

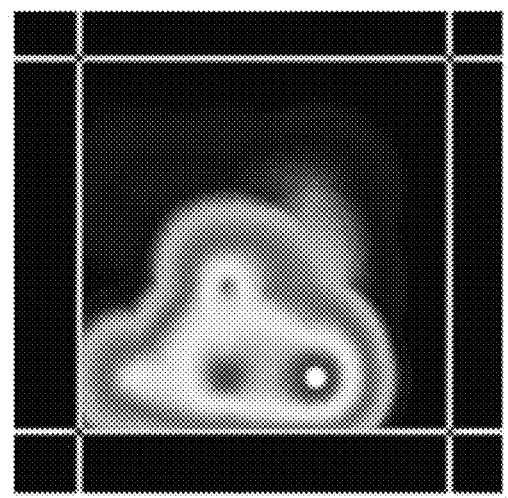
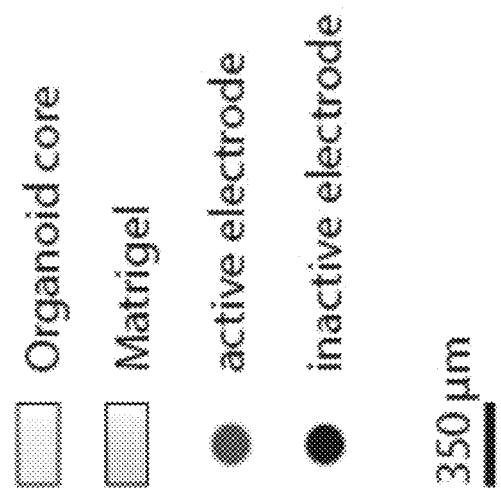
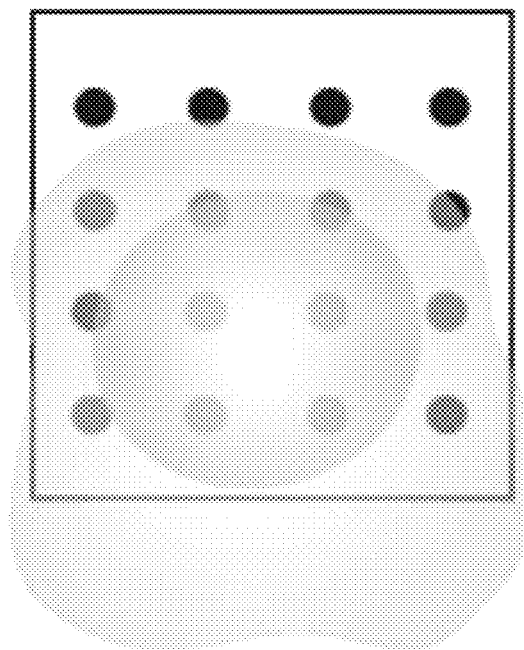
FIG. 12D
FIG. 12C

MEANS AND METHODS FOR GENERATING MIDBRAIN ORGANOIDS

The midbrain or mesencephalon is a portion of the central nervous system associated with vision, hearing, motor control, sleep/wake, arousal (alertness), and temperature regulation. During embryonic development, the midbrain arises from the second vesicle, also known as the mesencephalon, of the neural tube. Unlike the other two vesicles, the forebrain and hindbrain, the midbrain remains undivided for the remainder of neural development.

The midbrain is also that region of the brain, where the majority of the neurotransmitter dopamine (DA) is produced. Dopamine plays, inter alia, a major role in motivation and habituation of species from humans to the most elementary animals such as insects. The regions of DA producing neurons are derived from the tegmentum and are called the substantia nigra pars compacta (SNc, A9 group), and the ventral tegmental area (VTA, A10 group). Especially the mesencephalic dopaminergic (mDA) neurons of the SNc play an important role in the control of multiple brain functions. Their axons ascend rostrally into the dorsolateral striatum of the cortex, where they release the neurotransmitter dopamine (Abeliovich and Hammond, 2007; Gale and Li, 2008). The SNc is of particular interest since mDA neurons of this region selectively undergo degeneration in Parkinson's disease (PD), a progressive neurodegenerative disorder characterized by the progressive loss of dopaminergic neurons in the substantia nigra The loss of mDA neurons leads to a lack of DA in the striatum, which controls voluntary body movements under physiological conditions (Abeliovich and Hammond, 2007). In PD, the degeneration of DA neurons and the subsequent lack of DA in the striatum are associated to motor symptoms including tremor, bradykinesia, and rigidity. Mutation or deletions of several genes have been identified to predispose to the pathology.

Neuronal differentiation towards the dopaminergic lineage is a complex process, which highly relies on the sequential activation of specific transcription factors. In mammals, mDA progenitors start to develop at E7.5. LIM homeobox transcription factor 1a (LMX1A) and forkhead box protein A2 (FOXA2), both induced by SHH signaling, are important determination factors of mDA differentiation. Expression of LMX1A triggers dopaminergic differentiation and recruits MSX1/2, an inhibitor of negative regulators of neurogenesis. It further induces the expression of proneural factors such as Neurogenin 2 (NGN2), which are necessary for the proper development of mDA neurons (Gale and Li, 2008). Upon maturation, mDA progenitos migrate to exit the proliferative zone at E10.5-E11.5. At this stage, the phenotypic marker of mDA neuons, tyrosine hydroxylase (TH), the rate-limiting enzyme in dopamine synthesis is induced and mDA progenitors start to express the early neuronal marker βIII Tubulin (TUJ1) (Abeliovich and Hammond, 2007).

Many of the underlying studies of CNS development and specification have been carried out in mouse and chick embryos. Even though it is likely that many of the mechanisms are conserved between mammalian species, there are strong differences between murine and human neurodevelopment. For instance, the size of the cortex is remarkably increased in humans. Some regions, such as the outer subventricular zone or the inner fibre layer are completely absent in mice but present in humans. Notably, rodents are naturally not susceptible to neurodegenerative disorders such as PD and Alzheimer's disease (AD). In addition to differences in neurodevelopment, another obvious but striking difference is the ability to speak.

Parkinson's disease is characterized by the progressive loss of midbrain dopaminergic neurons in the substantia nigra pars compacta. The underlying mechanisms that lead to severe cell death remain poorly understood. Mouse models often cannot recapitulate the phenotype seen in vivo, especially in the case of complex pathologies such as neurodegenerative disorders, which do not affect animals. For this reason, given the divergences between humans and mice, which are most frequently used as in vivo model systems, as well as the shortcomings of 2D cell cultures, there is an obvious need for robust in vitro models of human brain development, especially in terms of studying neurodevelopmental and neurodegenerative diseases.

The technical problem underlying the present application is to comply with this need. The solution to said technical problem is the provision of means and methods for generating midbrain organoids as reflected in the claims, described herein, illustrated in the Figures and exemplified in the Examples of the present application.

Much to their surprise the present inventors observed that they were able to obtain midbrain organoids by contacting neuroepithelial stem cells with differentiation medium, when they cultured said neuroepithelial stem cells in a three-dimensional cell culture comprising a matrix under agitating conditions. Specifically, the present inventors used a human neural precursor cell line, called human neuroepithelial stem cells (hNESCs), which served as a starting population for the generation of midbrain organoids. A single colony was embedded into a matrix allowing three-dimensional cell culture, said matrix being e.g. a droplet of Matrigel. Matrigel droplets are described, for example, in Lancaster and Knoblich (2014a). A single colony was cultured under agitating conditions, such as continuous spinning. The medium used for differentiation contained, inter alia, signaling molecules for the induction of midbrain development as described herein. At several time points, midbrain organoids were characterized using immunohistochemical stainings in order to determine whether indeed a differentiation into midbrain-specific structures was detectable. After about 3 weeks of differentiation, midbrain organoids developed several neural cell types, including dopaminergic neurons, and an asymmetric organization, consistent with brain development in vivo. Such midbrain organoids may serve as 3D models which can, for example, be used to study neurodevelopmental and/or neurodegenerative diseases, such as Parkinson's disease (PD), Multiple sclerosis, Batten's disease or Alzheimer's disease.

During their studies, the present inventors observed that NESCs seeded on round-bottom plates with low attachment surfaces formed globular colonies that expanded quickly (FIG. 4). However, this involved increasing cell death in the centre of the colonies due to a limited nutrient exchange. Sectioning of early organoids between day 6 and 10 revealed that the majority of the cells in the core were dead. However, surprisingly, cell death significantly decreased when the 3D structures were kept under agitating conditions.

NESCs embedded in a matrix allowing three-dimensional cell culture such as MATRIGEL and kept under agitating conditions grew further and quickly started to develop long processes that migrated through the entire ECM (FIG. 4 d-f). These processes expressed the neuronal markers TUJ1 and partially MAP2, indicative of axon formation (FIG. 6 and FIG. 7). Upon neurogenesis, young neurons adopt bipolar morphology with leading and trailing processes, which eventually become axons between embryonic day 11 to 18

Figure 3:
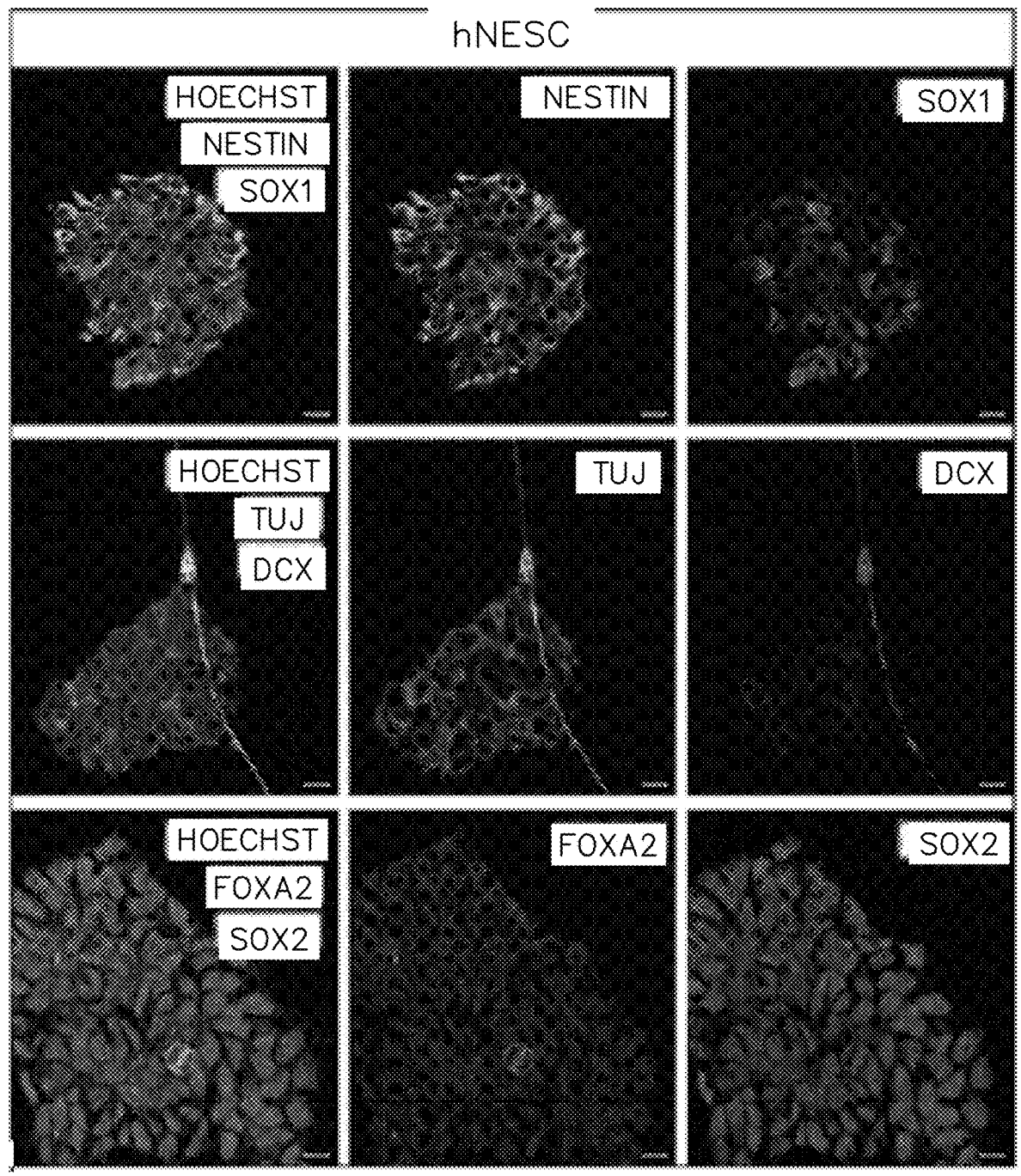
Figure 5A:
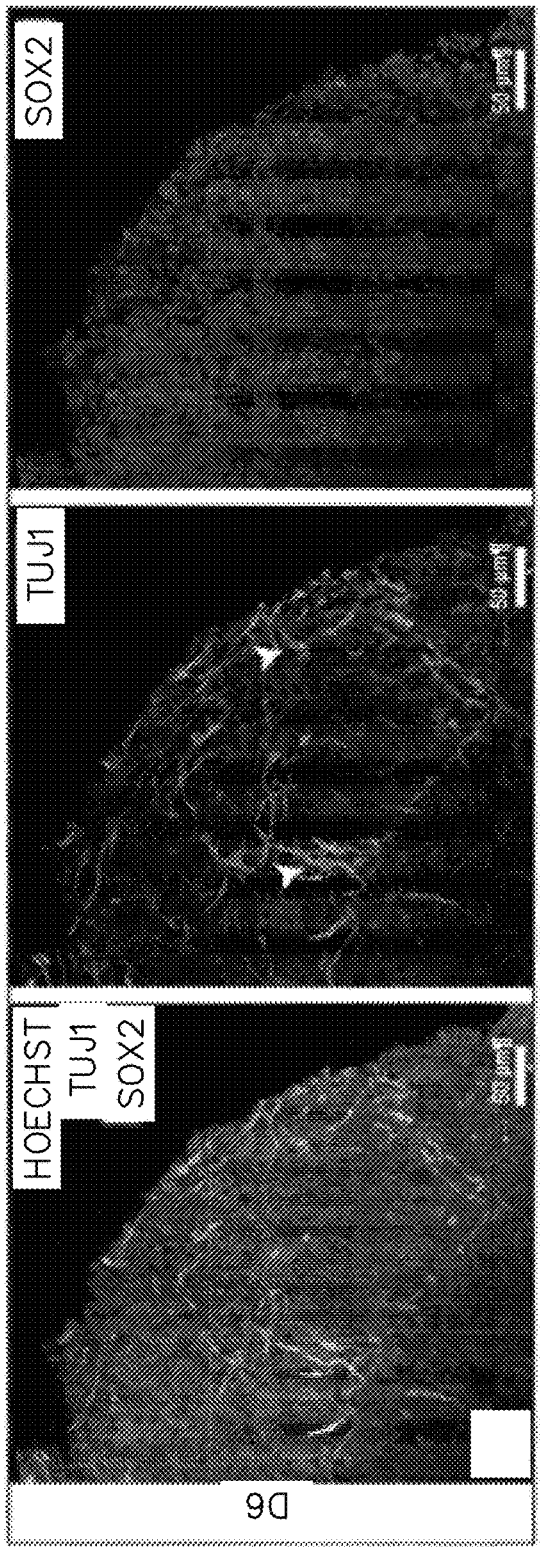
Figure 5B:
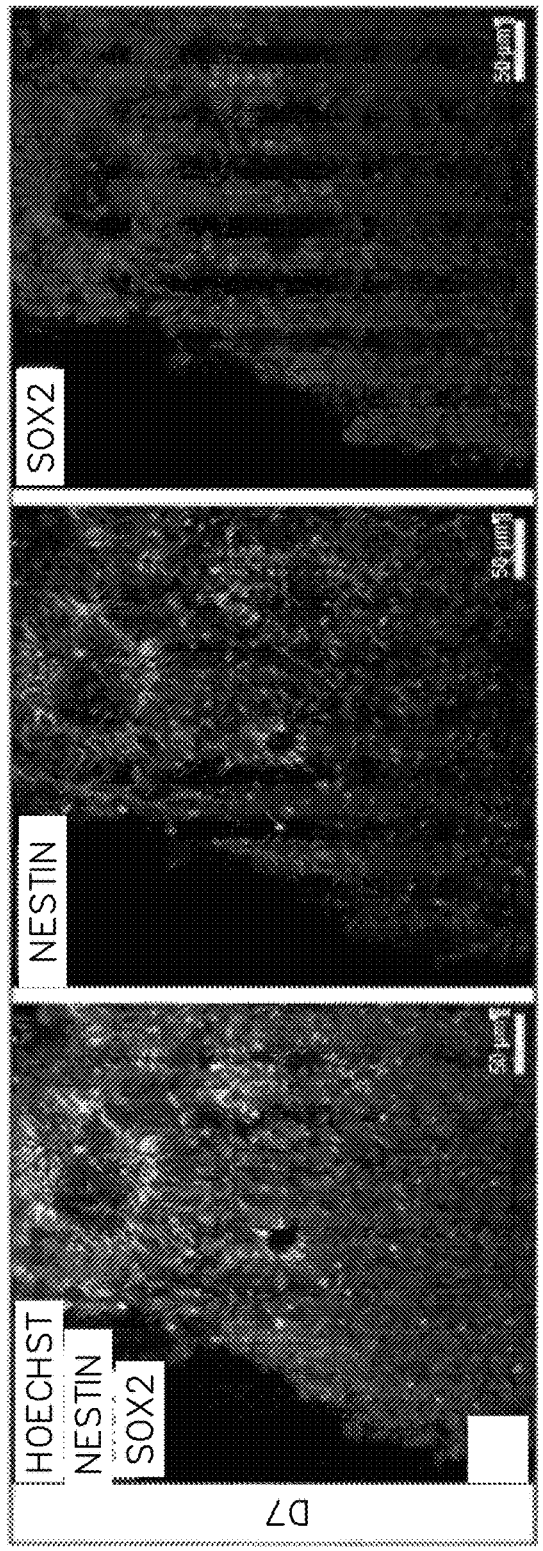

(Lewis et al., 2013). Cell bodies were mainly located adjacent to the core. Under maintenance conditions, hNESCs stably express the neural progenitor markers SOX1, SOX2, and NESTIN (FIG. 3). This expression pattern is retained in early midbrain organoids that were seeded on ultralow attachment plates (FIG. 5). Some SOX2 positive cells remained in the inner part of the organoid after 24 days of differentiation, abutting to TH positive DA neurons (FIG. 7). During the course of midbrain development in vivo, the neuroepithelium in the midbrain regions thickens and becomes layered. Some neural stem cells remain in the inner layer and retain their proliferative properties, while other cells migrate to an intermediate zone and start to differentiate into mDA neurons. Immature neurons continue to migrate to reach the marginal zone where they become mature neurons. The mDA neuron progenitors express LMX1, FOXA2, TH, and the neuronal marker TUJ1 (Ang, 2009; Gale and Li, 2008). In vitro, midbrain organoids seem to develop a similar layered organisation with neural stem cells remaining adjacent to the inner core and mDA neurons migrating basally. DA neurons started to develop after 6 days under differentiation conditions. Interestingly, DA neurons and neural precursors accumulated in a particular area and were not equally distributed across the tissue at day 30 and 44, suggesting self-patterning of midbrain organoids along the D-V axis (FIG. 6 and FIG. 7). However, not all TH positive cells are necessarily DA neurons. All catecholamines, including dopamine, noradrenaline, and adrenaline are synthesised from tyrosine. TH is the rate-limiting enzyme that produces L-DOPA from tyrosine (Sharples et al., 2014). To confirm that the TH$^+$ cells are indeed DA neurons, further markers such as DAT are to be considered. Importantly, midbrain organoids developed asymmetric polar structures, similar to brain development in vivo. To this end, the present inventors successfully generated midbrain organoids by using neuroepithelial stem cells as starting population for the generation said midbrain organoids by contacting them with differentiation medium under agitating conditions in three-dimensional cell culture comprising a matrix.

Accordingly, the present invention provides in one aspect a method of generating a midbrain organoid, comprising contacting neuroepithelial stem cells, which are cultured in a three-dimensional cell culture comprising a matrix, with differentiation medium, wherein the culturing is performed under agitating conditions, thereby obtaining a midbrain organoid.

The present invention also provides in another aspect midbrain organoid obtainable by the method of the present invention as well as in yet another aspect uses and methods applying the midbrain organoids of the present invention for testing compounds for their ability to elicit a cellular response on said midbrain organoid.

Furthermore, the present invention provides in a further aspect midbrain organoids as described herein for use in transplantation.

Having recognized that neuroepithelial stem cells can successfully be used for the generation of midbrain organoids as described herein, the present invention also provides in a yet further aspect the use of neuroepithelial stem cells, which are cultured in a three-dimensional cell culture comprising a matrix under agitating conditions, for generating a midbrain organoid unit.

The above aspects of present invention as well as preferred aspects thereof may also be summarized in the following items:

(1) A method of generating a midbrain organoid, comprising: contacting (only) neuroepithelial stem cells, which are cultured in a three-dimensional cell culture comprising a matrix, with differentiation medium, wherein the culturing is performed under agitating conditions, thereby obtaining a midbrain organoid.
(2) The method of item 1, wherein said neuroepithelial stem cells are human neuroepithelial stem cells, preferably said neuroepthelial cells express SOX1, SOX2, PAX6 and NESTIN.
(3) The method of item 2, wherein said neuroepithelial stem cells are hNESC-K7 or smNPCs.
(4) The method of any one of items 1-3, wherein said neuroepithelial stem cells are genetically modified or obtained from a patient suffering from a neurological disease.
(5) The method of item 4, wherein the genetic modification comprises a mutation, a knock-out or a knock-in.
(6) The method of item 4, wherein the neurological disease is a neurodegenerative disease such as Parkinson's disease, Multiple sclerosis, Batten's disease or Alzheimer's disease.
(7) The method of any one of items 1-6, wherein said neuroepithelial stem cells have been produced from induced pluripotent stem cells (iPSCs).
(8) The method of item 7, wherein the iPSCs are produced from fibroblasts or peripheral blood mononuclear cells (PBMCs), wherein the fibroblasts or PBMC have preferably been obtained from a patient.
(9) The method of any one of items 1-8, wherein the three-dimensional cell culture is performed in a gel, a bioreactor in ultra-low adhesion conditions or a microchip, preferably a hydrogel and/or a hydrogel droplet such as a Matrigel droplet.
(10) The method of any one of items 1-9, wherein the matrix is an extracellular matrix and/or wherein the matrix comprises one or more of natural molecules, synthetic polymers, biological-synthetic hybrids, metals, ceramics, bioactive glasses and/or carbon nanotubes.
(11) The method of any one of items 1-10, wherein the matrix comprises collagen, Matrigel, fibrin, hyaluronic acid, chitosan, alginate, silk fibrils, ethylene glycol such as PEG, poly(vinyl alcohol) and/or poly(2-hydroxy ethyl methacrylate), preferably the matrix comprises Matrigel.
(12) The method of any one of items 1-11, wherein said differentiation medium (differentiation medium I) comprises
(i) a SHH-pathway activator;
(ii) at least two different neurotrophins; and
(iii) an antioxidant.
(13) The method of any one of items 1-12, wherein said differentiation medium (differentiation medium II) comprises
(i) at least two different neurotrophins; and
(ii) an antioxidant.
(14) The method of item 12, wherein the SHH-pathway activator is selected from the group consisting of purmorphamine, SHH, smoothened agonist (SAG), Hh-Ag 1.5 and Gli-2, preferably the SHH-pathway activator is purmorphamine.
(15) The method of any one of items 12-14, wherein the at least two neurotrophins are selected form the group consisting of NGF, BDNF, NT-3, NT-4, CNTF and GDNF, preferably the at least two neurotrophins are GDNF and BDNF.

(16) The method of any one of items 12-15, wherein the antioxidant is selected from the group consisting of ascorbic acid, superoxide dismutase 1, superoxide dismutase 2, superoxide dismutase 3, glutathione, lipoic acid, epigallocatechin gallate, curcumine, melatonin, hydroxytyrosol, ubiquinone, catalase, vitamin E and uric acid, preferably the antioxidant is ascorbic acid.

(17) The method of any one of items 12-16, wherein the differentiation medium (differentiation medium I and/or II) further comprises an activator of activin/transforming growth factor-β (TGF-β) signaling pathway and/or wherein the differentiation medium II does not comprise a SHH-pathway activator.

(18) The method of item 17, wherein the activator of activin/TGF-β signaling pathway is selected from the group consisting of TGβ1, TGβ2, TGβ3, activin A, activin B, activin AB and nodal, preferably the activator of activin/TGF-β signaling pathway is TGFβ3.

(19) The method of any one of items 12-18, wherein the differentiation medium (differentiation medium I and/or II) further comprises a cAMP analogue.

(20) The method of item 19, wherein the cAMP analogue is selected from the group consisting of forskolin, 8-(4-chloro-phenylthio)-2'-O-methyladenosine-3',5'-cyclic monophosphate (8CPT-2Me-cAMP), 8-Chloro-cAMP (8-Cl-cAMP), Bucladesine, Rp-adenosine, 3', 5'-cyclic monophosphorothioate sodium salt (Rp-cAMPS), Sp-8-hydroxyadenosine, 3', 5'-cyclic monophosphorothioate sodium salt (Sp-80H-cAMPS) and Rp8-hydroxyadenosine, 3', 5'-cyclic monophosphorothioate sodium salt (Rp-80H-cAMPS) and dbcAMP, preferably the cAMP analogue is dbcAMP.

(21) The method of any one of items 12-20, wherein the differentiation medium (differentiation medium I and/or II) is a N2B27 medium.

(22) The method of item 21, wherein the N2B27 medium comprises equal amounts of Neurobasal medium and DMEM/F12 medium.

(23) The method of any one of items 12-22, wherein the differentiation medium (differentiation medium I and/or II) further comprises penicillin and streptomycin.

(24) The method of any one of items 12-23, wherein the differentiation medium (differentiation medium I and/or II) further comprises glutamine, preferably L-glutamine, more preferably L-glutamine at a concentration of 2 mM.

(25) The method of item 21, wherein the differentiation medium further comprises B27 supplement without vitamin A, preferably at a concentration of 1:100 (supplement:medium).

(26) The method of any one of items 12-25, wherein the differentiation medium ((differentiation medium I and/or II) further comprises N2 supplement, preferably at a concentration of 1:200 (supplement:medium).

(27) The method of any one of items 12-26, wherein the differentiation medium (differentiation medium I and/or differentiation medium II) does not comprise FGF8.

(28) The method of any one of items 12-27, wherein the cells are kept in the differentiation medium I for at least 1, 2, 3, 4, 5, 6, 7, 8, 9, 10, 11 or more days, preferably the cells are kept in the differentiation medium I for 6 days and/or wherein the cells are kept in differentiation medium II for at least 1, 2, 3, 4, 5, 6, 7, 8, 9, 10, 15, 20, 24, 38, 40, 50 or more days, preferably the cells are kept in the differentiation medium II for 1, 24 or 38 days.

(29) The method of item 28, wherein differentiation medium I is replaced by differentiation medium II after 6 days of differentiation by omitting the SHH-pathway activator from the differentiation medium.

(30) The method of any one of items 1-29, wherein FGF8 is added to the differentiation medium (differentiation medium I and/or II) after 8 days of differentiation.

(31) The method of any one of items 1-30, wherein the neuroepithelial stem cells are contacted by a maintenance medium before they are contacted with the differentiation medium.

(32) The method of item 31, wherein the maintenance medium comprises
   (i) a SHH-pathway activator;
   (ii) canonical WNT-signaling activator; and
   (iii) an antioxidant.

(33) The method of item 31 or 32, wherein the maintenance medium comprises N2B27 medium as defined in any one of items 21-27.

(34) The method of item 32 or 33, wherein the canonical WNT-signaling activator is selected from the group consisting of Norrin, R-spondin 2 or WNT protein.

(35) The method of any one of items 32-34, wherein canonical WNT-signaling activator blocks Axin or APC e.g. via siRNA.

(36) The method of any one of items 32-34, wherein canonical WNT-signaling activator is a GSK-3 inhibitor.

(37) The method of item 36, wherein the GSK-3 inhibitor is selected from the group consisting of CHIR 99021, SB-216763, 6-bromoindirubin-3'-oxime, Tideglusib, GSK-3 inhibitor 1, AZD1080, TDZD-8, TWS119, CHIR-99021 HCl, CHIR-98014, SB 415286, SB 216763, LY2090314, AR-A014418 and IM-12, preferably the GSK-3 inhibitor is CHIR 99021.

(38) The method of item 31-37, wherein the maintenance of the neuroepithelial stem cells takes place in a two-dimensional and/or three-dimensional cell culture.

(39) The method of item 38, wherein the maintenance of the neuroepithelial stem cells is performed in a three-dimensional cell culture for 1, 2, 3, 4, 5, 6 or more days, preferably wherein the maintenance of the neuroepithelial stem cells is performed in a three-dimensional cell culture for 2 days.

(40) The method of any one of items 1-39, wherein the neuroepithelial stem cells are present in a colony.

(41) The method of item 40, wherein the colony is a cluster of cell clones.

(42) The method of item 40 or 41, wherein said colony of neuroepithelial stem cells is obtainable by culturing said neuroepithelial stem cells for at least 1, 2, 3, 4, 5, 6, 7, 8, 9, 10, 11, 12, 13, 14, 15 or more days in the maintenance medium as defined in any one of items 31-39, preferably said neuroepithelial stem cells are cultured for 10 days in the maintenance medium as defined in any one of items 31-39.

(43) The method of item 42, wherein at least 50, 500, 1000, 2000, 3000, 4000, 5000, 6000, 7000, 8000, 9000, 10000, 11000, 12000, 13000, 14000, 15000, 16000 or more neuroepithelial stem cells, preferably about 9000 neuroepithelial stem cells are used as a starting cell population.

(44) The method of any one of items 40-43, wherein the colony of neuroepithelial stem cells is obtainable by culturing neuroepithelial cells in round bottom ultralow attachment 96-well plates and/or ultralow attachment 24-well-plates and/or in a three-dimensional cell culture.

(45) The method of any one of items 40-44, wherein the colony of neuroepithelial stem cells is cultured in a Matrigel droplet for at least 1 day.
(46) The method of any one of items 9-45, wherein said Matrigel droplet is cultured under agitating conditions after at least 1, 2, 3, 4, 5, 6, 7 or more days after initiation of differentiation, preferably the Matrigel droplet is cultured under agitating conditions after 2 or after 4 days after initiation of differentiation.
(47) The method of any one of items 1-46, wherein said agitating conditions comprise shaking, spinning, stirring, moving and/or mixing of the three-dimensional cell culture.
(48) The method of item 47, wherein the spinning is performed with a spinning bioreactor and/or the shaking is performed with an orbital shaker.
(49) The method of item 47 or 48, wherein said orbital shaker is shaking at least at 40 rpm, 50 rpm, 60 rpm, 70 rpm, 80 rpm, 90 rpm, 100 rpm, 110 rpm, or more, preferably said orbital shaker is shaking at 80 rpm.
(50) The method of any one of items 1-49, comprising:
  (i) contacting neuroepithelial stem cells with the maintenance medium as defined in any one of items 32-39;
  (ii) contacting neuroepithelial stem cells, which are cultured in a three-dimensional cell culture comprising a matrix, with the differentiation medium (I) as defined in any one of items 12, 14-30, wherein the culturing is performed under agitating conditions, wherein the agitating is started after 0, 1, 2, 3, 4, 5, 6, 7, 8 or more days, preferably 2 days or 4 days, after starting culturing of the neuroepithelial stem cells in the differentiation medium I;
  (iii) contacting neuroepithelial stem cells with the differentiation medium (II) as defined in any one of items 13-30 under agitating conditions.
thereby obtaining a midbrain organoid.
(51) The method of any one of items 1-50, comprising:
  (i) contacting neuroepithelial stem cells with the maintenance medium as defined in any one of items 32-39;
  (ii) culturing the neuroepithelial stem cells for 1, 2, 3, 4, 5, 6, 7, 8, 9, 10, 11, 12, 13 or more days in the maintenance medium;
  (iii) contacting neuroepithelial stem cells with the differentiation medium (I) as defined in any one of items 12, 14-30,
  (iv) culturing the cells of step (iii) for 1, 2, 3, 4, 5, 6, 7, 8, 9, 10, 11, 12, 13 or more days in the differentiation medium I, wherein the culturing is performed under agitating conditions, wherein the agitating is started after 0, 1, 2, 3, 4, 5, 6, 7, 8 or more days, preferably 2 days, after starting culturing of the neuroepithelial stem cells in the differentiation medium I;
  (v) contacting the cells obtained in step (iv) with the differentiation medium II as defined in any one of items 13-30; and
  (vi) culturing the cells of step (v) for 1, 2, 3, 4, 5, 6, 7, 8, 9, or more weeks in the differentiation medium II under agitating conditions;
thereby obtaining a midbrain organoid.

(52) The method of item 51, wherein the culturing of the neuroepithelial stem cells in step (ii) is performed for 9 or 10 days.
(53) The method of item 51 or 52, wherein the culturing of the cells of step (iv) is performed for 6 days.
(54) The method of any one of items 51-53, wherein the culturing the cells of step (vi) is performed for 1, 24 or 38 days.
(55) The method of any one of items 1-54, wherein the midbrain organoid is obtainable after 1, 2, 3, 4, 5, 6, 7, 8, 9, 10, 11, 12, 13 or more weeks of differentiation, preferably the differentiation is performed for 6, 7, 16, 30 or 44 days.
(56) The method of any one of items 1-55, wherein said midbrain organoid is an early midbrain organoid or a late midbrain organoid.
(57) The method of item 56, wherein the early midbrain organoid is a midbrain organoid, which has been differentiated for 1, 2, 3, 4, 6, 7, 8, 9, 10, 11, 12, 13, 14, 15, 16, 17, 18, 19 or 20 days, preferably the early midbrain organoid has been differentiated for 6, 7 or 16 days.
(58) The method of item 56, wherein the late midbrain organoid is a midbrain organoid, which has been differentiated for at least 25, 30, 35, 40, 50, 60 or more days, preferably the late midbrain organoid has been differentiated for 30, 44 or 51 days.
(59) The method of any one of items 1-58, wherein said midbrain organoid comprises
  (a) neural progenitor cells;
  (b) young neurons;
  (c) young dopaminergic neurons;
  (d) mature neurons;
  (e) mature dopaminergic neurons;
  (f) an asymmetric organization of the midbrain organoid;
  (g) oligodendrocytes;
  (h) oligodendrocyte progenitors;
  (i) astrocytes; and/or
  (j) processes that expand from the midbrain organoid through the matrix.
(60) The method of any one of items 56, 57 or 59, wherein the early midbrain organoid comprises
  (a) neural progenitor cells;
  (b) young neurons; and/or
  (c) Ki67-positive cells and/or
  (d) young dopaminergic neurons.
(61) The method of any one of items 56, 58 or 59, wherein the late midbrain organoid comprises
  (a) neural progenitor cells;
  (b) young neurons;
  (c) young dopaminergic neurons;
  (d) mature neurons;
  (e) mature dopaminergic neurons, preferably comprising or producing dopamine;
  (f) an asymmetric organization of the midbrain organoid;
  (g) oligodendrocytes, preferably expressing O4 and/or CNPase;
  (h) oligodendrocyte progenitors, preferably expressing NG2;
  (i) astrocytes, preferably expressing S100b and/or GFAP;
  (j) clustering of dopaminergic neurons within the organoid; and/or
  (k) processes that expand from the midbrain organoid through the matrix.

(62) The method of any one of items 59-61, wherein said neural progenitor cells are characterized by the expression of the markers SOX2 and/or nestin.

(63) The method of any one of items 59-62, wherein said young neurons are characterized by the expression of the marker TUJ1.

(64) The method of any one of items 59-63, wherein said young dopaminergic neurons are characterized by the expression of the markers TUJ1 and tyrosine hydroxylase (TH).

(65) The method of any one of items 59-64, wherein said mature neurons are characterized by the expression of the marker MAP2.

(66) The method of any one of items 59-65, wherein said mature dopaminergic neurons are characterized by the expression of the markers MAP2, TH, FOXA2 and/or the expression of the marker LMX1A and/or said mature dopaminergic neurons are characterized by the expression of the mRNA encoding for LMX1A, LMX1B, EN1, NURR1, AADC, and/or TH.

(67) The method of any one of items 59-66, wherein the asymmetric organization of the midbrain organoid is an asymmetric polar organization of dopaminergic neurons and/or an asymmetric organization of neuronal progenitor cells within the midbrain organoid.

(68) The method of any one of items 59-67, wherein said asymmetric polar organization of dopaminergic neurons within the midbrain organoid is characterized by the localization of
   (a) mature dopaminergic neurons in the outermost part of the midbrain organoid;
   (b) young dopaminergic neurons in the inner parts of the midbrain organoid.

(69) The method of item 68, wherein young dopaminergic neurons migrate towards the outermost part of the midbrain organoid upon maturation.

(70) The method of any one of items 59-69, wherein the asymmetric organization of neuronal progenitor cells within the midbrain organoid is characterized by the localization of neuronal progenitors in a ring-like structure surrounding the inner core of the midbrain organoid.

(71) The method of any one of items 59-70, wherein said oligodendrocytes are characterized by the expression of the marker O4 and/or expression of CNPase.

(72) The method of any one of items 59-71, wherein said oligodendrocyte progenitors are characterized by the expression of the marker NG2.

(73) The method of any one of items 59-72, wherein said astrocytes are characterized by the expression of the markers GFAP and/or S100b.

(74) The method of any one of items 59-73, wherein said clustering of dopaminergic neurons within the organoid is characterized by the accumulation of more than 2, 3, 4, 5, 6, 7, 8, 9, 10 or more dopaminergic neurons in a specific region of the midbrain organoid.

(75) The method of any one of items 59-74, wherein said processes that expand from the midbrain organoid through the matrix have a length of 0.1 mm, 0.2 mm, 0.3 mm, 0.4 mm, 0.5 mm, 0.6 mm, 0.7 mm, 0.8 mm, 0.9 mm, 1 mm, 1.1 mm, 1.2 mm or more.

(76) The method of any one of items 1-75, wherein the neuroepithelial stem cell is obtainable by a method comprising
   a) optionally obtaining/providing induced pluripotent stem cells (iPSCs);
   b) cultivating said iPSCs in a medium comprising
      (i) an activin/transforming growth factor-β (TGF-β) signaling inhibitor;
      (ii) a canonical WNT-signaling activator;
      (iii) a bone morphogenetic protein (BMP) signaling inhibitor; and
      (iv) a SHH-pathway activator; and
   c) cultivating the cells obtained in b) in a medium comprising
      (i) an activin/TGF-β signaling inhibitor;
      (ii) a canonical WNT-signaling activator;
      (iii) a BMP signaling inhibitor; and
      (iv) a SHH-pathway activator; and
   d) further cultivating the cells obtained in c) in a medium comprising
      (i) a canonical WNT-signaling activator;
      (ii) SHH-pathway activator; and
      (iii) an antioxidant; and
thereby obtaining a neuroepithelial stem cell.

(77) The method of item 76, wherein the method further comprises
   e) maintaining the cells obtained in d) in a medium comprising
      (i) a FGF signaling activator;
      (ii) an EGF signaling activator; and
      (iii) a LIF signaling activator.

(78) Midbrain organoid obtainable by the method of any one of items 1-77.

(79) Use of the midbrain organoid of item 78 for testing compounds for their ability to elicit a cellular response on said midbrain organoid.

(80) Use of item 79, wherein said compound is a drug, small molecule, hormone, growth factor, binding protein, nucleic acid molecule, peptide protein or (co-cultured) cell.

(81) Use of item 79 or 80, wherein said cellular response is the frequency or survival of a certain type of cell.

(82) Use of item 81, wherein said type of cell is a dopaminergic neuron.

(83) Method for testing a compound of interest for its ability to elicit a cellular response, comprising:
   (a) contacting the midbrain organoid of item 78 with said compound of interest; and
   (b) determining whether said compound of interest elicits a cellular response.

(84) The method of item 83, wherein said compound is a drug, small molecule, hormone, growth factor, binding protein, nucleic acid molecule, peptide protein or (co-cultured) cell.

(85) The method of item 83 or 84, wherein said cellular response is the frequency or survival of a certain type of cell.

(86) The method of item 85, wherein said type of cell is a dopaminergic neuron.

(87) The method for identifying molecules promoting or inhibiting dopaminergic neuronal differentiation and/or death of dopaminergic neurons in a midbrain organoid as defined in item 78, the method comprising contacting the midbrain organoid with a molecule of interest, wherein an increase of the differentiation into dopaminergic neurons compared to a control indicates that the molecule of interest promotes dopaminergic neuronal differentiation and/or inhibits death of dopaminergic neurons and wherein a decrease of the differentiation into dopaminergic neurons compared to a control indicates that the molecule of interest inhibits dopaminergic neuronal differentiation and/or induces death of dopaminergic neurons.

(88) The method of item 87, wherein the differentiation into dopaminergic neurons is measured by comparing neurite outgrowth.

(89) The method of item 87 or 88, wherein the differentiation into dopaminergic neurons is measured by comparing the expression of TH.

(90) The method of any one of items 87-89, wherein the control is a midbrain organoid which is not contacted with the molecule of interest.

(91) Composition comprising a midbrain organoid unit of item 78.

(92) The composition of item 91, which is a pharmaceutical composition.

(93) Use of neuroepithelial stem cells, which are cultured in a three-dimensional cell culture comprising a matrix under agitating conditions, for generating a midbrain organoid unit.

(94) Midbrain organoid of item 78 for use in transplantation.

Notably, the method as described herein can also comprise:

(i) contacting neuroepithelial stem cells with the maintenance medium as defined herein;

(ii) culturing the neuroepithelial stem cells for 1, 2, 3, 4, 5, 6, 7, 8, 9, 10, 11, 12, 13 or more days in the maintenance medium, preferably, the neuroepithelial stem cells are cultured for 10 days in the maintenance medium wherein optionally the neurepithelilal stem cells are transferred into a MATRIGEL droplet after 8 days;

(iii) contacting neuroepithelial stem cells with the differentiation medium (I) as described herein, (iv) culturing the cells of step (iii) for 1, 2, 3, 4, 5, 6, 7, 8, 9, 10, 11, 12, 13 or more days, preferably 6 days in the differentiation medium I, wherein the culturing is performed under agitating conditions, wherein the agitating is started after 0, 1, 2, 3, 4, 5, 6, 7, 8 or more days, preferably 4 days, after starting culturing of the neuroepithelial stem cells in the differentiation medium I;

(v) contacting the cells obtained in step (iv) with the differentiation medium II as described herein; and (vi) culturing the cells of step (v) for 1, 2, 3, 4, 5, 6, 7, 8, 9, or more weeks in the differentiation medium II under agitating conditions;

thereby obtaining a midbrain organoid.

An "organoid" resembles a whole organ. Organoids exhibit an intrinsic potential to self-organise, forming the cellular organisation of an organ. Organoids hold great promise for diagnostic and therapeutic applications. The organoid of the present invention is preferably a midbrain organoid. Accordingly, a midbrain organoid of the present invention resembles the midbrain. The midbrain is the region of the brain, where the majority of the neurotransmitter dopamine (DA) is produced. A midbrain organoid of the present invention is preferably from a single colony of a NESC, preferably a hNESC. A midbrain organoid of the present invention has preferably the phenotype of a midbrain. A midbrain organoid of the present invention is either an early midbrain organoid or a late midbrain organoid. A midbrain organoid of the present invention has preferably the phenotype of a midbrain. As such, it comprises typical cells/cell types of a midbrain. Accordingly, a midbrain organoid of the present invention comprises neural progenitor cells, young neurons, young dopaminergic neurons, mature neurons, mature dopaminergic neurons, an asymmetric organization, oligodendrocytes, oligodendrocyte progenitors, astrocytes, and/or processes that expand from the midbrain organoid through the matrix. These cell types are preferably characterized by the markers as described herein. Likewise, the asymmetric organization is preferably characterized as described herein and as well as the clustering of dopaminergic neurons and the processes that expand from the midbrain organoid through the matrix. Presence of the cells/cell types in a midbrain organoid of the present invention can be tested by means and methods known in the art and as described herein. Likewise, expression of the markers as described herein by said cells/cell types or the asymmetric organization can be tested as is known in the art and as described herein.

Organoids have the potential to model degenerative and developmental diseases and/or cancer, and represent a valuable tool to study genetic disorders and to identify subtle phenotypes. Somatic cells derived from patients can be reprogrammed into iPSCs and thereof-derived organoids can be used as a patient-specific model for drug tests or in regenerative medicine for organ replacement therapies. Insertion and correction of mutations in hiPSC-derived organoids might help to understand disease mechanisms. This is advantageously envisioned by the present invention, i.e. midbrain organoids of the present invention may serve as models which can, for example, be used to study neurodevelopmental and/or neurodegenerative diseases, such as Parkinson's disease (PD), Multiple sclerosis, Batten's disease or Alzheimer's disease.

The methods of the present invention can be carried out in any cell culture, while, however, three-dimensional cell culture is preferred. Culture conditions may vary, but the artificial environment in which the cells are cultured invariably consists of a suitable vessel comprising one or more of the following: a substrate or medium that supplies the essential nutrients (amino acids, carbohydrates, vitamins, minerals), growth factors, hormones, gases ($O_2$, $CO_2$) and/or regulated physico-chemical environment (pH, osmotic pressure, temperature). Cell culture as described herein refers to the maintenance and growth of cells in a controlled laboratory environment. Such in vitro cell culture models are well-known in experimental cell biological research. For example, cells can be cultured while attached to a solid or semi-solid substrate (adherent or monolayer culture). Cells can also be grown floating in the culture medium (suspension culture). However, it is preferred that cells of the present invention are cultured under agitating conditions.

Medium for cell culture, such as maintenance medium or differentiation medium is described herein elsewhere, e.g. in the items above.

Differentiation media as applied in the methods of the present invention comprise at least two different neurotrophins. The term "neurotrophins", as used herein, relates to a family of proteins that regulate the survival, development, and function of neurons. Exemplary neurotrophins include nerve growth factor (NGF), brain-derived neurotrophic factor (BDNF), neurotrophin-3 (NT-3), neurotrophin-4 (NT-4) as well as GDNF family of ligands and ciliary neurotrophic factor (CNTF). The GDNF family of ligands includes glial cell line-derived neurotrophic factor (GDNF), neurturin (NRTN), artemin (ARTN), and persephin (PSPN).

Accordingly, the term "at least two different neurotrophins" refers to two or more of the recited molecules. Preferably, the at least two different neurotrophins are BDNF and GDNF (Gene Symbols: BDNF and GDNF, respectively). BDNF can e.g. be the human BDNF protein of Uniprot/Swissprot accession no. P23560 (version 1 as of Oct. 31, 1991). GDNF can e.g. be the human GDNF protein of Uniprot/Swissprot accession no. P39905 (version 1 as of Jan. 31, 1995).

BDNF and GDNF can both independently from each other be employed in a concentration of between about 0.0001 and about 50 ng/µl each, more preferably between about 0.001 and about 25 ng/µl each, and most preferably the amount is about 0.001 ng/µl each. BDNF and GDNF may for example be obtained from Peprotech.

The differentiation medium as applied in the methods of the present invention may further comprise an antioxidant. An antioxidant is a molecule that inhibits the oxidation of other molecules. The terms "oxidation" and "antioxidant" are well known in the art and have been described, for example, in Nordberg J, Amer E S. (2001) "Reactive oxygen species, antioxidants, and the mammalian thioredoxin system." Free Radic Biol Med. 31(11):1287-312. In short, oxidation is a chemical reaction involving the loss of electrons or an increase in oxidation state. Oxidation reactions can produce free radicals. In turn, these radicals can start chain reactions. When the chain reaction occurs in a cell, it can cause damage or death to the cell. Antioxidants terminate these chain reactions by removing free radical intermediates, and inhibit other oxidation reactions. Accordingly, an antioxidant refers to an inhibitor of a molecule involved in cellular oxidative processes.

Exemplary antioxidants include ascorbic acid, superoxide dismutase 1, superoxide dismutase 2, superoxide dismutase 3, glutathione, lipoic acid, epigallocatechin gallate, curcumine, melatonin, hydroxytyrosol, ubiquinone, catalase, vitamin E or uric acid. Thus, the antioxidant can be ascorbic acid.

Any medium for cell culture as described herein may contain a ROCK inhibitor. A "ROCK inhibitor" as used herein is compound that acts as an inhibitor of Rho-associated protein kinase, i.e. reduces or even abolishes ROCK functionality. The capability of a compound to act as a ROCK inhibitor can be assessed by various means, e.g. by determining its ability to compete with ATP for binding to ROCK and/or by assessing its effects on cell morphology, G1-S Transition and cytokinesis as described in Ishizaki T Mol Pharmacol. 2000 May; 57(5):976-83. The inhibitor may be either unspecific or specific for either of the ROCK isoforms ROCK1 and/or ROCK2. ROCK inhibitors known in the art have been reviewed in Liao et al. J Cardiovasc Pharmacol. 2007 July; 50(1): 17-24 and include Fasudil, Y-27632, Thiazovivin, Y39983, Wf-536, SLx-2119, Azabenzimidazole-aminofurazans, DE-104, Olefins, Isoquinolines, Indazoles, pyridinealkene derivatives, H-1152P, ROKa inhibitor, XD-4000, 4-(1-aminoalkyl)-N-(4-pyridyl) cyclohexane-carboxamides, HMN-1152, Rhostatin, BA-210, BA-207, BA-215, BA-285, BA-1037, Ki-23095, VAS-012, with Y-27632 or Thiazovivin being particularly envisaged for use in the method of the invention.

Differentiation medium as applied in the methods of the present invention can further comprise an activator of activin/transforming growth factor-β (TGF-β) signaling pathway. The activin/TGF-β signaling pathway is known in the art and for example described in Heldin, Miyazono and ten Dijke (1997) "TGF-bold beta signaling from cell membrane to nucleus through SMAD proteins." Nature 390, 465-471. In short, Receptor ligands, including, for example, TGFB1, TGFB2, TGFB3, ACTIVIN A, ACTIVIN B, ACTIVIN AB, and/or NODAL, bind to a heterotetrameric receptor complex consisting of two type I receptor kinases, including, for example, TGFBR2, ACVR2A, and/or ACVR2B, and two type II receptor kinases, including, for example, TGFBR1, ACVR1 B, and/or ACVR1C. This binding triggers phosphorylation and activation of a heteromeric complex consisting of an R-smad, including, for example, SMAD2, and/or SMAD3, and a Co-smad, including, for example, SMAD4. Accordingly, the term "activator of the activin/TGF-β signaling pathway" refers to an activator of any one of the above recited molecules that form part of this signaling pathway.

Exemplary activators of the activin/TGF-β signaling pathway include TGβ1, TGβ2, TGFβ3, activin A, activin B, activin AB or nodal. Thus, the activator of activin/TGF-β signaling pathway can be TGFβ3. The activator of the activin/TGF-β signaling pathway such as TGFβ3 can be utilized in an amount of 0.0001 ng/µl to 0.1 ng/µl such as e.g. in an amount of 0.001 ng/µl.

Differentiation medium as applied in the methods of the present invention can further comprise a cAMP analogue. Such cAMP analogs are compounds that have similar physical, chemical, biochemical, or pharmacological properties as the cyclic adenosine monophosphate (cAMP). cAMP is known to the skilled artesian and described in e.g. Fimia G M, Sassone-Corsi P. (2001) "Cyclic AMP signalling." J Cell Sci; 114 (Pt 11):1971-2.

Differentiation medium as applied in the methods of the present invention can further be a N2B27 medium (into which the different compounds are diluted). This means that the medium comprises a N2 supplement and a B27 supplement. Both supplements are well known to the person skilled in the art and freely available. The B27 supplement can be a B27 supplement without vitamin A. This B27 can be used at a concentration of 1:10-1:1000, such as 1:100 (supplement:medium). The B27 supplement can for example be obtained from Life technologies. Likewise, also the N2 supplement can for example be obtained from Life technologies. The N2 supplement may be used at a concentration of 1:20 to 1:2000, such as 1:200 (supplement:medium).

Differentiation medium may also be a Neurobasal medium and/or a DMEM-F12 medium. Both media can for example be obtained from Life technologies. The N2B27 medium can for example comprise equal amounts of Neurobasal medium and DMEM/F12 medium.

Differentiation medium as applied in the methods of the present invention can further comprise an antibiotic.

Differentiation medium as applied in the methods of the present invention can further comprise glutamine.

Differentiation medium as applied in the methods of the present invention can comprise N2B27 medium comprising about 50% DMEM-F12 (e.g. from Life technologies)/about 50% Neurobasal (e.g. from Life technologies), about 1:200 N2 supplement (e.g. from Life technologies), about 1:100 B27 supplement lacking vitamin A (e.g. from Life technologies), 1% Penicillin/Streptomycin (e.g. from Life technologies) and 2 mM L-glutamine (e.g. from Life technologies).

In addition, cells may be cultured in a two-dimensional cell culture. This type of cell culture is well-known to the person skilled in the art. In two-dimensional (2D) cell culture cells are grown on flat plastic dishes such as Petri dish, flasks and multi-well plates. However, biologically derived matrices (e.g. fibrin, collagen and as further described herein) and synthetic hydrogels (e.g. PAA, PEG and as further described herein) can be used to elicit specific cellular phenotypes that are not expressed on rigid surfaces.

The methods of the present invention are, however, preferably be carried out in a three dimensional cell culture. A "three-dimensional cell culture" or "3D cell culture" as used herein means that cells are grown in an artificially-created environment in which cells are permitted to grow or interact with its surroundings in all three dimensions. For example, in order to achieve the three dimensional property of the cell culture, cells are grown or differentiated in matrices or scaffolds. In principle, suitable matrices or scaffolds, which can be used in three dimensional cell cultures are known to the skilled artesian. Such matrices or scaffolds can therefore be any matrix or scaffold. For example, the matrix or scaffold can be an extracellular matrix comprising either natural molecules or synthetic polymers, a biological and synthetic hybrid, metals, ceramic and bioactive glass or carbon nanotubes.

Exemplary natural extracellular matrix molecules include collagen, basement membranes such as laminin or fibrin, alginates, chitosan, hyaluronic acid, silk fibroin, cellulose actetate, casein, chitin, fibrinogen, gelatine, elastin or poly-(hydroxyalkanoate). Synthetic extracellular matrix polymers include Hyaluronic acid (HA) modified forms, Poly-ethylen glycol (PEG) modified forms, Self-assembling protein hydrogels, Poly(lactic-co-glycolic acid) (PLGA), Poly-caprolactone (PCL), Polyurethane or PGS. Biological and synthetic hybrids can for example include Polycaprolactone-chitosan, PLLA-Hydroxyapatite, Hydroxyapatite-bioglass-ceramic, Poly-(hydroxylalkanoate)-bioglass, Hydroxyapatite-collagen, PCL-gelatin or PCL-collagen. Exemplary metals include Tantalam, Magnesium and its alloys, Titanium and its alloys or Nitinol (nickel and titanium alloys). Examples of Ceramics and bioactive glass matrices/scaffolds include Titanium and tri calcium phosphate, Hydroxyapatite and Tricalcium phosphate, Bioactive silicate glass ($SiO_2$-$Na_2O$—$CaO$—$P_2O_5$), Hydroxyapatite and bioglass, Calcium phosphate glass or Phosphate glass. Carbon nanotubes can be constructed using graphite ranging from 0.4 to 2 nm. Carbon nanotubes can comprise CNT-polycaprolactone, CNT-ceramic matrix, 45S5 bioglass-CNT, CNT studded with gelatine hydrogel, CNT-TiO2, CNT-laminin, CNT grafted with polyacrylic acid or CNT-TGF-β.

The matrix or scaffold can also be a hydrogel such as Matrigel, fibrin gel or alginate gel. Matrigels can be a reconstituted basement membrane preparation extracted from Engelbreth-Holm-Swarm mouse sarcoma, a tumor rich in extracellular matrix proteins. Matrigel can be constituted of 60% laminin, 30% type IV collagen and 8% entactin. Optionally growth factors and other molecules can be added to the Matrigel. The Matrigel can also be BD Matrigel™ (obtainable from BD Biosciences).

Neuroepithelial stem cells (NESCs) when referred to herein can be derived from actual stem cells in several different stages of neural development. Neuroepithelial cells are a class of stem cell and have similar characteristics as stem cells. For example, these cells are able to self-renew. Self-renewal is the ability to go through numerous cell cycles of cell division while maintaining the undifferentiated state. In addition, neuroepithelial stem cell cells have the capacity to differentiate further into multiple types of cells, such as neurons, astrocytes and other glial cells. Thus, these cells are also multipotent. They are restricted to the neural lineage and can differentiate into neurons, astrocytes, and oligodendrocytes (Gage, 2000). Methods for testing if a cell has the capacity to self-renew and if a cell is multipotent are known to the skilled artesian. Self-renewal may be tested by passaging the cells over more than 10, 11, 12, 13, 14, 15, 16, 17, 18, 19, 20, 21, 22, 23, 24, 25, 26, 27, 28, 29, 30 or more passages. Passaging includes splitting of the cells before re-plaiting them as a single cell suspension. Multipotency can be tested by differentiating said cells into different lineages such as astrocytes, oligodendroctyes and neurons.

Furthermore, a neuroepithelial stem cell can express markers such as PAX6, Notch 1, Nestin, PCNA, Hes5 and Sox1. In particular, the neuroepithelial stem cells used in the methods of the present invention can be mammalian neural plate border stem cells (NPBSC) as described in WO2013104752. Furthermore, the neuroepithelial stem cells used in the methods of the present invention can also be NPBSCs as described in WO2013104752, which are also obtained by the method as described in WO2013104752. These NPBSC can be characterized by the expression of at least three markers selected from the group consisting of FORSE1, MSX1, PHOX2B, PAX3, PAX6, SOX1, SOX2, NESTIN, IRX3, HOXA2, HOXB2, HESS, DACH1, PLZF, LM03, EVI1 and ASCL1. Furthermore, these cells can be characterized by a lack of expression of at least one of the markers OCT4, NANOG, AFP, T, SOX17, EOMES, GSH2, OLIG2, CK8, CK18, NKX2.2, NKX6.1, HOXB8, HOXAS, FOXA2 and VCAM-1.

It is further envisioned that the neuroepithelial stem cells (N ESC) used in the present invention express the markers SOX1, SOX2, PAX6 and/or NESTIN. Additionally or alternatively, the NESCs used in the present invention have been passaged for more than 5, 6, 7, 8, 9, 10, 11, 12, 13, 14, 15, 16, 17, 18, 19 20 or more times. It is also envisioned that the NESCs used in the present invention have been passaged less than 20, 19, 18, 17, 16, 15, 14, 13, 12, 11, 10, 9, 8, 7, 6, 5, 4, 3, or 2 times. It is also envisioned that the NESCs used in the present invention have been passaged less than 20 and more than 2 times.

Notably, NESCs differ from cells of the embryoid bodies, which are three-dimensional aggregates of pluripotent stem cells. These embryoid bodies can be neurally induced. However, such induced cells may not be patterned well towards midbrain/hindbrain identity. In particular, compared to iPSCs as a starting population, NESCs are already patterned towards midbrain/hindbrain identity. This makes NESCs particularly suitable for use in the present invention. It is also envisioned that FGF8 is firstly added after 8 days of differentiation to the mediums (e.g. differentiation medium I and/or differentiation medium II) as described herein. The reason for this is that in this way the efficiency of the generation of dopaminergic neurons can be increased.

The neuroepithelial stem cell can be a mammalian NESC. It is also encompassed by the present invention that the NESC is a human NESC (hNESC), such as hNESC-K7. A neuroepithelial stem cell may be obtained by different means and methods known to the skilled artesian. For example, a neuroepithelial stem cell may be derived or obtained from pluripotent cells. NESC of the present invention may be genetically modified or be obtained from a patient suffering from a neurological disease, such as PD. Also, NESC may be produced from iPSCs, fibroblasts or PBMCs as described herein.

Totipotent stem cells (lat. "capable of everything") can give rise to all cell types of the body, including the germ line of the trophectoderm (Weissman, 2000).

A "pluripotent stem cell" when referred to herein relates to a cell type having the capacity for self-renewal, and the potential of differentiation into different cell types. Pluripotent stem cells can differentiate into nearly all cells, i.e. cells derived from any of the three primary germ layers: ectoderm, endoderm, and mesoderm. The term pluripotent stem cells also encompasses stem cells derived from the inner cell mass of an early stage embryo known as a blastocyst.

Multipotent stem cells are already restricted to a tissue or an organ and can give rise to all the tissue-specific cells.

Notably, recent advances in embryonic stem cell research have led to the possibility of creating new embryonic stem cell lines without destroying embryos, for example by using a blastomere biopsy-based technique, which does not interfere with the embryo's developmental potential (Klimanskaya (2006) "Embryonic stem cells from blastomeres maintaining embryo viability." Semin Reprod Med. 2013 January; 31(1):49-55). Furthermore, a large number of established embryonic stem cell lines are available in the art. Thus, it is possible to work with embryonic stem cells without the necessity to destroy an embryo. Takahashi and Yamanaka addressed these concerns and published a method to generate induced pluripotent stem cells (iPSCs) from somatic cells (Takahashi and Yamanaka, 2006). Skin fibroblasts were induced with four defined factors to reprogram the cells back to the pluripotency state. Those stem cells have the same essential characteristics as ESCs (FIG. 1) (Takahashi et al., 2007; Takahashi and Yamanaka, 2006; Yu et al., 2007). In one embodiment, the pluripotent stem cells are embryonic stem cells, which have not been obtained via the destruction of a human embryo. Thus, the pluripotent stem cells are embryonic stem cells obtained from an embryo, without the destruction of the embryo.

A neuroepithelial stem cell can also be derived or obtained from another pluripotent cell, namely an induced pluripotent stem cell (iPSC). "Induced pluripotent stem cells", as used herein, refers to adult somatic cells that have been genetically reprogrammed to an embryonic stem cell-like state by being forced to express genes and factors important for maintaining the defining properties of embryonic stem cells. Thus, induced pluripotent stem cells derived from a non-pluripotent cell.

Induced pluripotent stem cells are an important advancement in stem cell research, as they allow obtaining pluripotent stem cells without the use of embryos. Mouse iPSCs were first reported in 2006 (Takahashi, K; Yamanaka, S (2006). "Induction of pluripotent stem cells from mouse embryonic and adult fibroblast cultures by defined factors". Cell 126 (4): 663-76), and human iPSCs were first reported in 2007 (Takahashi et al. (2007) "Induction of pluripotent stem cells from adult human fibroblasts by defined factors." Cell; 131(5):861-72). Mouse iPSCs demonstrate important characteristics of pluripotent stem cells, including expression of stem cell markers, forming tumors containing cells from all three germ layers, and being able to contribute to many different tissues when injected into mouse embryos at a very early stage in development. Human iPSCs also express stem cell markers and are capable of generating cells characteristic of all three germ layers. Such stem cell markers can include Oct3/4, Sox2, Nanog, alkaline phosphatase (ALP) as well as stem cell-specific antigen 3 and 4 (SSEA3/4). Also the chromatin methylation patterns of iPSC are also similar to that of embryonic stem cells (Tanabe, Takahashi, Yamanaka (2014) "Induction of pluripotency by defined factors." Proc. Jpn. Acad., 2014, Ser. B 90).

In addition, iPSCs are able to self-renew in vitro and differentiate into cells of all three germ layers. The pluripotency or the potential to differentiate into different cell types of iPSC can tested, e.g., by in vitro differentiation into neural or glia cells or the production of germline chimaeric animals through blastocyst injection.

Methods for the generation of human induced pluripotent stem cells are well known to the skilled person. Usually forced expression of Oct3/4, Sox2 and Klf4 (as well as OCT3/4, SOX2 and KLF4) is sufficient to generate an induced pluripotent stem cell out of an adult somatic cell, such as a fibroblast. However, also the combination of Oct3/4, Sox2, c-Myc and Klf4 (as well as OCT3/4, SOX2, C-MYC) and KLF4 is sufficient for the generation of an iPSC from an adult somatic cell. In addition, also the combination of OCT3/4, SOX2, NANOG and LIN28 was efficient for reprogramming (Tanabe, Takahashi, Yamanaka (2014) "Induction of pluripotency by defined factors." Proc. Jpn. Acad., 2014, Ser. B 90). For this, these genes are usually cloned into a retroviral vector and transgene-expressing viral particles or vectors, with which the somatic cell is co-transduced. However, also other techniques known to the skilled artesian can be used for that purpose. Human skin fibroblasts can also be co-transduced with all four vectors e.g. via protein transduction or naked DNA.

Further methods for obtaining iPSCs are also known to the skilled artesian and for example described in WO2009115295, WO2009144008 or EP2218778. Thus, the skilled artesian can obtain an iPSC by any method.

In principle, induced pluripotent stem cells may be obtained from any adult somatic cell (of a subject). Exemplary somatic cells include peripheral blood Mononuclear Cells (PBMCs) from blood or fibroblasts, such as for example fibroblasts obtained from skin tissue biopsies.

Therefore, it is envisioned by the present invention that the NESC is produced or derived or obtained from an induced pluripotent stem cell (iPSC). Different ways how to differentiate iPCSs into neuroepithelial stem cells are known to the skilled artesian and for example described in WO2013/104752. In addition, it is envisioned by the present invention that the iPSCs can be produced from somatic cells such as fibroblasts. Furthermore, the iPSC can be a human iPSC (hiPSC).

It is further encompassed by the present invention that the somatic cells such as fibroblasts have been obtained from a subject. The term "subject" can also mean human or an animal. The subject can also be a subject suffering from a neurodegenerative disease such as Parkinson's disease. In particular, the subject may be a subject comprising the LRRK2-G2019S mutation, which is associated with familial Parkinson's disease. The subject can also be a subject not suffering from a neurodegenerative disease such as Parkinson's disease. Also encompassed by the present invention is that the subject is a healthy subject. The subject can be a vertebrate, more preferably a mammal. Mammals include, but are not limited to, farm animals, sport animals, pets, primates, dogs, horses, mice and rats. A mammal can be a human, dog, cat, cow, pig, mouse, rat etc. Thus, in one embodiment, the subject is a vertebrate. The subject can also be a human subject.

"Agitation" or "agitating" when used herein encompasses any technique that keeps cells in motion, i.e. cells are essentially not allowed to adhere to surfaces. Agitation can be achieved in a number of ways, including shaking, spinning, stirring, moving and/or mixing. Spinning can, for example, be achieved by the use of spinner flasks containing a magnetic paddle or impeller. Alternatively, the methods of the invention can be carried out in a bioreactor. A number of types of bioreactor are available, including bioreactors in which agitation of the medium is achieved using a paddle or impeller and rotary wall bioreactors. Rotary wall bioreactors can additionally be used to simulate conditions of reduced gravity (microgravity). It is also desirable to monitor and/or control the shear forces experienced by cells in operation of the methods of the present invention. For example, optimal conditions in cultures subjected to agitation require balancing the requirement for even distribution of oxygen and nutrients throughout the culture against the need to avoid cell damage due to excessive shear forces.

The term "activator", as used herein, is defined as a compound/molecule enhancing or achieving the activity of a target molecule or pathway. The activator may achieve this effect by enhancing or inducing the transcription of the gene encoding the protein to be activated and/or enhancing the translation of the mRNA encoding the protein to be activated. It can also be that the protein to be activated performs its biochemical function with enhanced efficiency in the presence of the activator or that the protein to be activated performs its cellular function with enhanced efficiency in the presence of the activator. Accordingly, the term "activator" encompasses both molecules/compounds that have a directly activating effect on the specific pathway but also molecules that are indirectly activating, e.g. by interacting for example with molecules that negatively regulate (e.g. suppress) said pathway. The activator can also be an agonist of the pathway to be activated. Methods for testing if a compound/molecule is capable to induce or enhance the activity of a target molecule or pathway are known to the skilled artesian. For example, an activator of a SHH, WNT or other activator as described herein can be tested by performing Western Blot analysis of the amount of e.g. pathway effector proteins such as Gli proteins, LEF1 or TCF1 protein, respectively.

The compound/molecule that can be used as an activator can be any compound/molecule, which can activate the respective pathway or which inhibits a suppressor of the pathway to be activated. Exemplary activators can include suitable binding proteins directed e.g. against suppressors of a certain pathway.

An activator may enhance or increase the pathway to be activated by 10%, 20%, 30%, 40%, 50%, 60%, 70%, 80%, 90%, 100% or more when compared to the activity of the pathway without or before the addition of the activator.

The "Hedgehog signaling pathway" or "SHH pathway" is well known in the art and has been described, for example, in et al. (2014) "Sonic hedgehog signalling pathway: a complex network." Ann Neurosci. 21(1):28-31. Hedgehog ligands, including, for example, Sonic hedgehog, Indian hedgehog, and/or Desert hedgehog, bind to the receptor, including, for example, Patched or the patched-smoothened receptor complex, which induces a downstream signaling cascade. Downstream target genes of SHH signaling include GLI1, GLI2 and/or GLI3. Accordingly, the term "activator of the Hedgehog signaling pathway" also refers to an activator of any one of the above recited molecules that form part of this signaling pathway.

Exemplary activators of the Hedgehog signaling (SHH) include purmorphamine (PMA; 2-(1-Naphthoxy)-6-(4-morpholinoanilino)-9-cyclohexylpurine 9-Cyclohexyl-N-[4-(4-morpholinyl)phenyl]-2-(1-naphthalenyloxy); CAS No.: 483367-10-8), SHH, smoothened agonist (SAG; 3-chloro-N-[trans-4-(methylamino)cyclohexyl]-N-[[3-(4-pyridinyl)phenyl]methyl]-benzo[b]thiophene-2-carboxamide; CAS No.: 912545-86-9) and Hh-Ag 1.5 (3-chloro-4,7-difluoro-N-(4-(methylamino)cyclohexyl)-N-(3-(pyridin-4-yl)benzyl)benzo[b]thiophene-2-carboxamide; CAS No.: 612542-14-0) as well as Gli-2. The SHH-pathway activator can also be selected from the group consisting of purmorphamine, SHH, SAG Analog and Gli-2. The SHH-pathway activator can therefore be purmorphamine. The SHH pathway activator can also be a recombinant or truncated form of SHH, which retains SHH pathway activating functions such as e.g. SHH 02411.

The SHH signaling pathway activator such as purmorphamine can be employed in a concentration of between about 0.25 µM and about 1 M, more preferably between about 0.4 µM and about 0.5 µM, and most preferably the amount is about 0.5 µM.

The SHH signaling pathway activator such as SHH can also be employed between about 50 and about 1000 ng/ml. The SHH signaling pathway activator such as SHH 02411 can also be employed in a concentration of about 10 and about 500 ng/ml. The SHH signaling pathway activator such as SAG can be employed in a concentration of about 1 and about 100 nM. The SHH signaling pathway activator such as Hh-Ag1.5 can also be employed in a concentration of about 1 and about 50 nM.

The media as used in the methods of the present invention can additionally or alternatively comprise a canonical WNT-signaling activator. The canonical Wnt signaling pathway is known to the skilled artesian and for example described in Logan and Nusse (Annu. Rev. Cell Dev. Biol. (2004) 20:781-810). In short, a Wnt ligand binds to Frizzled receptors, which triggers displacement of the multifunctional kinase GSK-3β from a regulatory APC/Axin/GSK-3β-complex. In the absence of Wnt-signal (Off-state), β-catenin, is targeted by coordinated phosphorylation by CK1 and the APC/Axin/GSK-3β-complex leading to its ubiquitination and proteasomal degradation through the β-TrCP/SKP pathway. In the presence of Wnt ligand (On-state), the co-receptor LRP5/6 is brought in complex with Wnt-bound Frizzled. This leads to activation of Dishevelled (Dvl), which displaces GSK-3β from APC/Axin. The transcriptional effects of Wnt ligand is mediated via Rac1-dependent nuclear translocation of β-catenin and the subsequent recruitment of LEF/TCF DNA-binding factors as co-activators for transcription. Exemplary Wnt ligands include for example Wnt1, Wnt3, Wnt3a, Wnt4, Wnt5a, Wnt7a, Wnt7b, and/or Wnt11.

Accordingly, the term "canonical WNT-signaling activator" as described herein refers to an activator of any one of the above recited molecules that form part of this signaling pathway.

Exemplary canonical WNT-signaling activators include Norrin, R-spondin 2 or WNT protein. However, the canonical WNT-signaling activator can also block Axin or APC. This can be achieved for example via siRNA or miRNA technology.

Exemplary canonical WNT-signaling activators can thus include Norrin, R-spondin 2 or WNT protein. However, the canonical WNT-signaling activator can also block Axin or APC. This can be achieved for example via siRNA or miRNA technology. It is also encompassed by the present invention that the canonical WNT-signaling activator is a GSK-3 inhibitor. Exemplary GSK-3 inhibitors include CHIR 99021 (6-[[2-[[4-(2,4-Dichlorophenyl)-5-(5-methyl-1H-imidazol-2-yl)-2-pyrimidinyl]amino]ethyl]amino]-3-pyridinecarbonitrile; CAS No.: 252917-06-9), SB-216763 (3-(2,4-Dichlorophenyl)-4-(1-methyl-1H-indol-3-yl)-1H-pyrrole-2,5-dione; CAS No.: 280744-09-4), 6-bromoindirubin-3'-oxime (CAS No.: CAS 667463-62-9), Tideglusib (4-Benzyl-2-(naphthalen-1-yl)-1,2,4-thiadiazolidine-3,5-dione), GSK-3 inhibitor 1 (CAS No.: 603272-51-1), AZD1080 (CAS No.: 612487-72-6), TDZD-8 (4-Benzyl-2-methyl-1,2,4-thiadiazolidine-3,5-dione; CAS No.: 327036-89-5), TWS119 (3-[[6-(3-aminophenyl)-7H-pyrrolo[2,3-d]pyrimidin-4-yl]oxy]-phenol; CAS No.: 601514-19-6), CHIR- 99021 (CAS No.: 252917-06-9), CHIR-98014 (N6-[2-[[4-(2,4-dichlorophenyl)-5-(1H-imidazol-1-yl)-2-pyrimidinyl]amino]ethyl]-3-nitro-2,6-Pyridinediamine; CAS No.: 252935-94-7), SB 415286 (3-[(3-Chloro-4-hydroxyphenyl)amino]-4-(2-nitrophenyl)-1H-pyrrol-2,5-dione; CAS No.: 264218-23-7), LY2090314 (3-(9-fluoro-2-(piperidine-1-carbonyl)-1,2,3,4-tetrahydro-[1,4]diazepino[6,7,1-hi]indol-7-yl)-4-(imidazo[1,2-a]pyridin-3-yl)-1H-pyrrole-2,5-dione; CAS No.: 603288-22-8), AR-A014418 (N-(4-Methoxybenzyl)-N'-(5-nitro-1,3-thiazol-2-Aurea; CAS No.: 487021-52-3 and/or IM-12 (3-(4-Fluorophenylethylamino)-1-methyl-4-(2-methyl-1H-indol-3-yl)-1H-pyrrole-2,5-dione; CAS No.: 1129669-05-1). Thus, the GSK-3 inhibitor can also be CHIR 99021.

The canonical WNT-signaling activator such as CHIR 99021 can be employed in a concentration of between about 0.01 μM and about 1 M, more preferably between about 0.1 μM and about 5 μM, and most preferably the amount is about 3 μM. CHIR 99021 can for example be obtained from Axon Medchem.

The media as used in the methods of the present invention can for example comprise an activin/TGF-β inhibitor.

The activin/TGF-β signaling pathway is known in the art and for example described in Heldin, Miyazono and ten Dijke (1997) "TGF-bold beta signaling from cell membrane to nucleus through SMAD proteins." Nature 390, 465-471. In short, receptor ligands, including, for example, TGFB1, TGFB2, TGFB3, ACTIVIN A, ACTIVIN B, ACTIVIN AB and/or NODAL, bind to a heterotetrameric receptor complex comprising two type I receptor kinases, including, for example, TGFBR2, ACVR2A, and/or ACVR2B, and two type II receptor kinases, including, for example, TGFBR1 (ALK5), ACVR1B (ALK4) and/or ACVR1C (ALK7). This binding triggers phosphorylation and activation of a heteromeric complex consisting of an R-smad, including, for example, SMAD2, and/or SMAD3, and a Co-smad, including, for example, SMAD4. Accordingly, the term "activator of the activin/TGF-β signaling pathway" refers to an activator of any one of the above recited molecules that form part of this signaling pathway, while the term "inhibitor of the activin/TGF-β signaling pathway" refers to inhibitors of any one of the above recited molecules that form part of this signaling pathway. In addition, such an activator can be an agonist of the ACVR2A and/or ACVR1B (ALK4) receptor or an agonist of the TGFβR11 receptor and/or ALK5 receptor. Such an inhibitor can be an antagonist of the ACVR2A and/or ACVR1B (ALK4) receptor or an antagonist of the TGFβR11 receptor and/or ALK5 receptor. In principle such inhibitors/activators of the activin/TGF-β signaling pathway are known to the skilled artesian and are commercially available.

The invention contemplates that the activin/TGF-β inhibitor is an inhibitor of the TGF-β type I receptor activin receptor-like kinase(s). Further envisioned by the present invention is that the activin/TGF-β inhibitor inhibits ALK5, ALK4 and/or ALK7. Exemplary but non-limiting examples of an activin/TGF-β inhibitor are A-83-01 (3-(6-Methyl-2-pyridinyl)-N-phenyl-4-(4-quinolinyl)-1H-pyrazole-1-carbothioamide; CAS No.: 909910-43-6), D4476 (44442,3-Dihydro-1,4-benzodioxin-6-yl)-5-(2-pyridinyl)-1H-imidazol-2-yl]benzamide; CAS No.: 301836-43-1), GW788388 (4-[4-[3-(2-Pyridinyl)-1H-pyrazol-4-yl]-2-pyridinyl]-N-(tetrahydro-2H-pyran-4-yl)-benzamide; CAS No.: 452342-67-5), LY364947 (4-[3-(2-pyridinyl)-1H-pyrazol-4-yl]-quinoline; CAS No.: 396129-53-6), R268712 (4-[2-Fluoro-5-[3-(6-methyl-2-pyridinyl)-1H-pyrazol-4-yl]phenyl]-1H-pyrazole-1-ethanol; CAS No.: 879487-87-3), SB-431542 (4-(5-Benzol[1,3]dioxol-5-yl-4-pyrldin-2-yl-1H-imidazol-2-yl)-benzamide hydrate; CAS No.: CAS Number 301836-41-9), SB-505124 (2-(5-Benzo[1,3]dioxol-5-yl-2-tert-butyl-3H-imidazol-4-yl)-6-methylpyridine hydrochloride hydrate; CAS No.: 694433-59-5), SD208 (2-(5-Chloro-2-fluorophenyl)-4-[(4-pyridyl)amino]pteridine; CAS No.: 627536-09-8), SB-525334 (6-[2-tert-Butyl-5-(6-methyl-pyridin-2-yl)-1H-imidazol-4-yl]-quinoxaline; CAS No.: 356559-20-1) and ALK5 Inhibitor II (CAS: 446859-33-2). The activin/TGF-β inhibitor can thus be SB-431542.

The activin/TGF-β inhibitor such as SB-431542 can be employed in a concentration of between about 0.01 μM and about 1 M, more preferably between about 5 μM and about 15 μM, and most preferably the amount is about 10 μM. For example, SB-431542 can be obtained from Ascent Scientific.

The media as used in the methods of the present invention can additionally or alternatively comprise a BMP signaling inhibitor. The BMP signaling pathway is known to the skilled artesian and for example described in Jiwang Zhanga, Linheng Lia (2005) BMP signaling and stem cell regulation Developmental Biology Volume 284, Issue 1, 1 Aug. 2005, Pages 1-11.

In short, BMP functions through receptor-mediated intracellular signaling and subsequently influences target gene transcription. Two types of receptors are required in this process, which are referred to as type I and type II. While there is only one type II BMP receptor (BmprII), there are three type I receptors: Alk2, Alk3 (Bmprla), and Alk6 (Bmprlb). BMP signal transduction can take place over at least two signaling pathways. The canonical BMP pathway is mediated by receptor I mediated phosphorylation of Smad1, Smad5, or Smad8 (R-Smad). Two phosphorylated R-Smads form a heterotrimeric complex coaggregate with a common Smad4 (co-Smad). The Smad heterotrimeric complex can translocate into the nucleus and can cooperate with other transcription factors to modulate target gene expression. A parallel pathway for the BMP signal is mediated by TGFβ1 activated tyrosine kinase 1 (TAK1, a MAPKKK) and through mitogen activated protein kinase (MAPK), which also involves cross-talk between the BMP and Wnt pathways.

It is envisioned by the present invention that the inhibitors of BMP signaling can only block/reduce the canonical BMP pathway. Thus, the BMP signaling inhibitor can be a cancoical BMP signaling inhibitor. One such inhibitor selective for canocial BMP signaling pathway is dorsomorphin. Exemplary, but non-limiting, examples of BMP signaling inhibitors include chordin, noggin, DMH1 (CAS 1206711-16-1), K 02288 (3-[(6-Amino-5-(3,4,5-trimethoxyphenyl)-3-pyridinyl]phenol; CAS No.: 1431985-92-0), dorsomorphin (6-[4-(2-Piperidin-1-ylethoxy)phenyl]-3-pyridin-4-yl pyrazolo[1,5-a]pyrimidine; CAS No.: 866405-64-3) and LDN 193189 (4-[6-[4-(1-Piperazinyl)phenyl]pyrazolo[1,5-a]pyrimidin-3-yl]-quinoline hydrochloride, CAS No.: 1062368-24-4). The BMP signaling inhibitor can also be dorsomorphin.

The BMP signaling inhibitor such as dorsomorphin can be employed in a concentration of between about 0.01 μM and about 1 M, more preferably between about 0.1 μM and about 5 μM, and most preferably the amount is about 0.1 μM. Dorsomorphin can for example be obtained from Tocris.

In accordance with the present invention, "Map2" refers to Microtubule-associated protein 2, a protein that in humans is encoded by the MAP2 gene. Map2 belongs to the microtubule-associated protein family. The proteins of this family are thought to be involved in microtubule assembly, which is an essential step in neuritogenesis. Human MAP2 mRNA can comprise sequence as shown in the NCBI reference NM_001039538 (SEQ ID NO: 1) and/or the protein can comprise the sequence as obtained from Uniprot No. P11137 (SEQ ID NO: 2). The term Map2 embraces any Map2 nucleic acid molecule or polypeptide and can also comprise fragments or variants thereof. The skilled person knows how to detect Map2. Such methods are also described in the Examples.

In accordance with the present invention, "TH" refers to Tyrosine hydroxylase/tyrosine 3-monooxygenase/tyrosinase, a protein that in humans is encoded by the TH gene. TH is the enzyme responsible for catalyzing the conversion of the amino acid L-tyrosine to L-3,4-dihydroxyphenylalanine (L-DOPA). Human TH mRNA can e.g. comprise a sequence as shown in NCBI reference NM_000360 (SEQ ID NO: 3) and/or the protein sequence of Uniprot No. P07101 (SEQ ID NO: 4). The term TH embraces any TH nucleic acid molecule or polypeptide and can also comprise fragments or variants thereof. The skilled person knows how to detect TH. Such methods are also described in the Examples.

In accordance with the present invention, "Tuj1" also known as "13111 Tubulin" is a protein that in humans is encoded by the TUBB3 gene. The protein 13111 Tubulin (TuJ1) is present in newly generated immature postmitotic neurons and differentiated neurons and in some mitotically active neuronal percursors. Human Tuj mRNA can comprise sequence as shown in the NCBI reference NM_006086.3 (SEQ ID NO: 5) and/or the protein can comprise sequence as shown in the Uniprot No. Q13509 (SEQ ID NO: 6). The term Tuj1 embraces any Tuj1 nucleic acid molecule or polypeptide and can also comprise fragments or variants thereof. The skilled person knows how to detect Tuj1. Such methods are also described in the Examples.

In accordance with the present invention, "GFAP" also known as Glial fibrillary acidic protein is a protein that in humans is encoded by the GFAP gene. Glial fibrillary acidic protein is an intermediate filament (IF) protein that is expressed by numerous cell types of the central nervous system (CNS) including astrocytes. Human GFAP mRNA can comprise sequence as shown in the the NCBI reference NM_001131019 (SEQ ID NO: 7) and/or the protein can comprise sequence as shown in the Uniprot No. P14136 (SEQ ID NO: 8). The term GFAP embraces any GFAP nucleic acid molecule or polypeptide and can also comprise fragments or variants thereof. The skilled person knows how to detect GFAP. Such methods are also described in the Examples.

In accordance with the present invention, "S100b" or "S10013" also known as S100 calcium-binding protein B is a protein that in humans is encoded by the S100 gene. S100 proteins are localized in the cytoplasm and nucleus of a wide range of cells, and involved in the regulation of a number of cellular processes such as cell cycle progression and differentiation. Human S100b mRNA can comprise sequence as shown in the NCBI reference NM 006272 (SEQ ID NO: 9) and/or the protein can comprise sequence as shown in the Uniprot No. P04271 (SEQ ID NO: 10). The term S100b embraces any S100b nucleic acid molecule or polypeptide and can also comprise fragments or variants thereof. The skilled person knows how to detect S100b. Such methods are also described in the Examples.

In accordance with the present invention, "PAX6" also referred to as Paired box protein Pax-6 also known as aniridia type II protein (AN2) or oculorhombin is a protein that in humans is encoded by the PAX6 gene. Pax6 is a transcription factor present during embryonic development. The encoded protein contains two different binding sites that are known to bind DNA and function as regulators of gene transcription. It is a key regulatory gene of eye and brain development. Human PAX6 mRNA can comprise any sequence encoding for SEQ ID NO: 11. Human PAX6 can also comprise the protein sequence as shown by Uniprot No. P26367 (SEQ ID NO: 11). The term PAX6 embraces any PAX6 nucleic acid molecule or polypeptide and can also comprise fragments or variants thereof. The skilled person knows how to detect PAX6. Such methods are also described in the Examples.

In accordance with the present invention, "SOX1" also referred to as "SOX1 Sex determining region Y-box 1" is a protein that in humans is encoded by the SOX1 gene. SOX1 (for Sex determining region Y-box 1) is a transcription factor in the Sox protein family. Human SOX1 mRNA can comprise any sequence encoding for SEQ ID NO:12. SOX1 can also comprise the protein sequence of Uniprot No. 000570 (SEQ ID NO: 12). The term SOX1 embraces any SOX1 nucleic acid molecule or polypeptide and can also comprise fragments or variants thereof. The skilled person knows how to detect SOX1. Such methods are also described in the Examples.

In accordance with the present invention, "SOX2" also known as sex determining region Y-box 2, is a protein that in humans is encoded by the SOX2 gene. SOX2 is a transcription factor that is essential for maintaining self-renewal, or pluripotency, of undifferentiated embryonic stem cells. Sox2 has a critical role in maintenance of embryonic and neural stem cells. Human SOX2 mRNA can comprise any sequence encoding for SEQ ID NO: 13. SOX2 can also comprise the protein sequence of Uniprot No. P48431 (SEQ ID NO: 13). The term SOX2 embraces any SOX2 nucleic acid molecule or polypeptide and can also comprise fragments or variants thereof. The skilled person knows how to detect SOX2. Such methods are also described in the Examples.

In accordance with the present invention, "nestin" is a protein that in humans is encoded by the NES gene. Nestin is a type VI intermediate filament (IF) protein. Human nestin mRNA can comprise any sequence encoding for SEQ ID NO: 14. Nestin can also comprise a protein sequence such as depicted by Uniprot No. P48681 (SEQ ID NO: 14). The term nestin embraces any nestin nucleic acid molecule or polypeptide and can also comprise fragments or variants thereof. The skilled person knows how to detect nestin. Such methods are also described in the Examples.

In accordance with the present invention, "LMX1A" (LIM homeobox transcription factor 1, alpha) is a protein that in humans is encoded by the LMX1A gene. LMX1 is a LIM homeobox transcription factor that binds an A/T-rich sequence in the insulin promoter and stimulates transcription of insulin. Human LMX1A mRNA can comprise any sequence encoding for SEQ ID NO: 15. LMX1A can also comprise a protein sequence such as depicted by Uniprot No. Q8TE12 (SEQ ID NO: 15). The term LMX1A embraces any LMX1A nucleic acid molecule or polypeptide and can also comprise fragments or variants thereof. The skilled person knows how to detect LMX1A. Such methods are also described in the Examples.

In accordance with the present invention, "FOXA2" is a protein that in humans is encoded by the FOXA2 gene. Forkhead box protein A2 is a member of the forkhead class of DNA-binding proteins. Human FOXA2 mRNA can comprise any sequence encoding for SEQ ID NO: 16. FOXA2 can also comprise a protein sequence such as depicted by Uniprot No. Q9Y261 (SEQ ID NO: 16). The term FOXA2 embraces any FOXA2 nucleic acid molecule or polypeptide and can also comprise fragments or variants thereof. The skilled person knows how to detect FOXA2. Such methods are also described in the Examples.

In accordance with the present invention, "LMX1B" is a protein that in humans is encoded by the LMX1B gene. LMX1B is a LIM homeobox transcription factor which plays a central role in dorso-ventral patterning of the vertebrate limb. Human FOXA2 mRNA can comprise any sequence encoding for SEQ ID NO: 17. LMX1B can also comprise a protein sequence such as depicted by Uniprot No. O60663 (SEQ ID NO: 17). The term LMX1B embraces any LMX1B nucleic acid molecule or polypeptide and can also comprise fragments or variants thereof. The skilled person knows how to detect LMX1B. Such methods are also described in the Examples.

In accordance with the present invention, "NURR1" is a protein that in humans is encoded by the NR4A2 gene. NURR1 is a member of the nuclear receptor family of intracellular transcription factors. NURR1 plays a key role in the maintenance of the dopaminergic system of the brain. Human NURR1 mRNA can comprise any sequence encoding for SEQ ID NO: 18. NURR1 can also comprise a protein sequence such as depicted by Uniprot No. P43354 (SEQ ID NO: 18). The term NURR1 embraces any NURR1 nucleic acid molecule or polypeptide and can also comprise fragments or variants thereof. The skilled person knows how to detect NURR1. Such methods are also described in the Examples.

In accordance with the present invention, "AADC" is an Aromatic L-amino acid decarboxylase. Human AADC mRNA can comprise any sequence encoding for SEQ ID NO: 19. AADC can also comprise a protein sequence such as depicted by Uniprot No. P20711 (SEQ ID NO: 19). The term AADC embraces any AADC nucleic acid molecule or polypeptide and can also comprise fragments or variants thereof. The skilled person knows how to detect AADC. Such methods are also described in the Examples.

In accordance with the present invention, "EN1" is a protein that in humans is encoded by the EN1 gene. Engrailed (EN) is a homeodomain transcription factor involved in many aspects of multicellular development. Human EN1 mRNA can comprise any sequence encoding for SEQ ID NO: 20. EN1 can also comprise a protein sequence such as depicted by Uniprot No. Q05925 (SEQ ID NO: 20). The term EN1 embraces any EN1 nucleic acid molecule or polypeptide and can also comprise fragments or variants thereof. The skilled person knows how to detect EN1. Such methods are also described in the Examples.

Unless otherwise indicated, all numbers expressing quantities of ingredients, properties such as molecular weight, reaction conditions, and so forth used in the specification and claims are to be understood as being modified in all instances by the term "about." As used herein the terms "about" and "approximately" means within 10 to 15%, preferably within 5 to 10%. Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

| SEQ ID No. | Description of Sequence (marker) | Sequence |
|---|---|---|
| 1 | Map2 mRNA | AGTCTGGGGCGGGCGCTCGGGCTGCGCGGGCTCTGGGCAGCAGCAGCAGCAGCAGCAT
CCTCTCTTCCTTTACTTCCCTTCCGCTTCTTTCTCTTCCTTCTCCTTCTTTTTCCCCCCCC
TCCCCTTCTTCCCCTAACCCTTCTACCCCTCTCCTTTTTCTCCGGAGGGCGCTAAGTCCGT
GAGCGGTGGCAGTCGCGACCGCGGGTGCATCCAGTTTCTGCGCCCAGATTTTATTGATCTA
ATCCAAAGTATCTTATAACTTCTGGCTGGAATTAAGATTCTTCAGCTTGTCTCTAACCGAG
GAAGCATTGATTGGGAGCTACTCATTCAGAAAATTAAAAGAAAGAAGCCAGAAAATATTAT
CAACCCTTTGAGAACACGACACAACGAACTTTATATTTTACCACTTCCTTGAATAGTTGCA
GGAGAAATAACAAGGCATTGAAGAATGGCAGATGAACGGAAAGATGAAGCAAAGGCACCTC
ACTGGACCTCAGCACCGCTAACAGAGGCATCTGCACACTCACATCCACCTGAGATTAAGGA
TCAAGGCGGAGCAGGGGAAGGACTTGTCCGAAGCGCCAATGGATTCCCATACAGGGAGGAT
GAAGAGGGTGCCTTTGGAGAGCATGGGTCACAGGGCACCTATTCAAATACCAAAGAGAATG
GGATCAACGGAGAGCTGACCTCAGCTGACAGAGAAACAGCAGAGGAGGTGTCTGCAAGGAT
AGTTCAAGTAGTCACTGCTGAGGCTGTAGCAGTCCTGAAAGGTGAACAAGAGAAAGAAGCT
CAACATAAAGACCAGACTGCAGCTCTGCCTTTAGCAGCTGAAGAAACAGCTAATCTGCCTC
CTTCTCCACCCCCATCACCTGCCTCAGAACAGACTGTCACAGTGGAGGAAGCAGCAGGTGG
GGAATCAGCTCTGGCTCCCAGTGTATTTAAACAGGCAAAGGACAAAGTCTCTAATTCTACC
TTGTCAAAGATTCCTGCTTTACAGGGTAGCACAAAGTCCCAAGATACAGCTCAGCCTGCC
CTAGCACGACTAAAAGGGCTACATTTTCTGACAGTTTATTAATACAGCCCACCTCAGCAGG
CTCCACAGACCGTTTGCCATACTCAAAATCAGGGAACAAGGACGGAGTAACAAGAGCCCA
GAAAAGCGCTCTTCTCTCCCAAGACCTTCCTCCATTCTCCCTCCTCGGCGAGGTGTGTCAG
GAGACAGAGATGAGAATTCCTTCTCTCAACAGTTCTATCTCTTCTTCAGCACGGCGGAC
CACCAGGTCAGAGCCAATTCGCAGAGCAGGGAAGAGTGGTACCTCAACACCCACTACCCCT
GGGTCTACTGCCATCACTCCTGGCACCCCACCAAGTTATTCTTCACGCACACCAGGCACTC
CTGGAACCCCTAGCTATCCCAGGACCCCTCACACACCAGGAACCCCCAAGTCTGCCATCTT
GGTGCCGAGTGAGAAGAAGGTCGCCATCATACGTACTCCTCCAAAATCTCCTGCGACTCCC
AAGCAGCTTCGGCTTATTAACCAACCACTGCCAGACCTGAAGAATGTCAAATCCAAAATCG
GATCAACAGACAACATCAAATACCAGCCTAAAGGGGGGCAGGTTAGGATTTTAAACAAGAA
GATCGATTTTAGCAAAGTTCAGTCCAGATGTGGTTCCAAGGATAACATCAAACATTCGGCT
GGGGGCGGAAATGTACAAATTGTTACCAAGAAAATAGACCTAAGCCATGTGACATCCAAAT
GTGGCTCTCTGAAGAACATCCGCCACAGGCCAGGTGGCGGACGTGTGAAAATTGAGAGTGT
AAAACTAGATTTCAAAGAAAAGGCCCAAGCTAAAGTTGGTTCTCTTGATAATGCTCATCAT
GTACCTGGAGGTGGTAATGTCAAGATTGACAGCCAAAAGTTGAACTTCAGAGAGCATGCTA
AGCCCGTGTGGACCATGGGCTGAGATCATTACACAGTCCCAGGCAGATCCAGCGTGGC
ATCACCCCGACGACTCAGCAATGTCTCCTCGTCTGGAAGCATCAACCTGCTCGAATCTCCT
CAGCTTGCCACTTTGGCTGAGGATGTCACTGCTGCACTCGCTAAGCAGGGCTTGTGAATAT
TTCTCATTTAGCATTGAAATAATAATATTTAGGCATGAGCTCTTGGCAGGAGTGGGCTCTG
AGCAGTTGTTATATTCATTCTTTATAAACCATAAAATAAATAATCTCATCCCCAAACTGTA
GTAATTGTTACAATTTTCTATTTAAAAAATGAATAGTACATGCAGAAATTGACCTGATTTC
CATTTGCAACAGGAAGACACTGGCTTTACATGGGTTCAATTGGACAATTATTTTTGCTCTG
CTCTGTTTTGCATGGAGTATTATTATTTTAAAAATTGCATTTTTACCTTTCATGTGCCTGA
AGGCTATCCACTACATTCTGAAGGCCTTGTTAAAATCCAAGCTGCTCATTTCACTATTCTG
TTTCTGAGTGAGAAGATAAAAACTGCCCATTGTAACTTATTTCAGGTTAAATTAAACCAAG
GAGTCTGATTGCAGGAAGGGAAGAGCATGTAAGAAATAAGTTTTTTTAAAGTGTTATTTTG
TATAAATGGGAAGAAAGATTCAATTAAGTTATTAACATTTGGGACCTGGATAATTATATCA
GAGTATGTCAGTCCAATAAATTATTTAACTAATTAAAAAATAGTTGCAAAGCATTTGAGCT
GTGGTTGAGGAAGTGGTGTAAAAGTGCATCCATTAGGAATGATGCACTTTCATTAGGATGG
ACTCGTGTCTGATTAGAATGTCAGTTGATCAGCTAGATTTGTGTCCACACTACCAGTTTCA
CACCCCCTTTCCATCTGTTTGATACAGTATTATAGATATAAATATATATATATTTCTCTGT
GGCCATTTGTGACATTCCTCATATACTTGAATATTATACTTCTTTATTCACAGTATCTGT
GTCTCCTGCACCCTTTGGTGTTGCAATTTTAGATATGTGAAAGTAGATGTTAGCAGGGTTC
TCTCCCTATTTAAAAAAAATACATTAAAAAAGACAAAAAATTTTAGCATGAAGTTGCTTTC
TGTAACAACTCAAAGCCGTAACCCTGTTTTAGTGCCAGATACAAGTCTCTCCCGTGATGCT
AGACAAAAAATTATTTTCTTTGCTTTCACCAACATGGAGTTTGTGGGGGTGGGTCCAGTT
ATACATGAAAGGGTTTACAGATTGTTGGTTTAAGATTATGGATTTATCTCATTTTTAATCA
CAGGATAGTTTGGGGTTTATTCCTATTATTATTCATGAAACCGACTTAAGATTTTTTCTTT
ATTTTTCTTTTTTTTCCATTTGCTAAAGTTGAAAGTTGAAACTAACTATAATAGTTTGAA
ACATGTTTTCTCATTTTTCCAAATAGTATCTGTTTATTAAATTCTCTAATAGAAGATGTTT
GTCTTTCTTACCCAAAGTAAAGATCCCCTGATCAGAAAGAAAAAATACAATACTTTGGGAA
GCTATAGCTATAAAACACTTGAGACACAGATATCTAAATCAGTTTTTTTCCAAGACTCCAA
CATTGCACTCTGTAAAGTAACACACTGTGATCTAGTATTATTTATCAGTAGATAATACTGT
TCTGACTGTATATACAGTCTAGAACTCACAAATCAATTAGTTCCTCTCACAAATCATTCAT
CTTAGACTTACAAATAAGGAATGAAATAGTCAATGGCCTGATTAAGGCAAAGAGCTACCAG
GCTAGATGGACACTTTTTAAAAATTTTATCTGTTCTTTTTCTTGCTCAGGGCTGGTAGGTT
GGATCTGAACCATTAAAATCAAATGGTCCACTAGGCGTATGATCTCTTTGAGCCAAATCAG
TTCCTGAATATAAAGGAGGAAATGATGAGGATGTACTGAGGCAACGGGGAAGTATAGAAAC
ATCCAAGACAAAAGCCAAGGGATGCAAAGGCAGAGACACAGGTGCTTTTTGGTGACCCAGT
GGATATGGCAACCAGTGTAACTGCCATACAAGAAACCTAGGAGCAAACCCACACCACTCA
TTCTCAGCTAAGAGATTTTACACAGGCAAACGTGTCTTAAACCATCTATAAATCAGTTATT
TTATATGACAGTCAAAACCTTAGAAACCTTAGGATCATTATATTTTCTGCCTATTAA
TTGCTGTGAGGTTTGATTTGACCAATCTGGGCAATTTATTCATCAGCTTCCCTTGAAGTGC
ACCAGAAAATAGAAGAAAGGTGTGTGGAGACTTAGGGTATTTTATTACATGTTTTCATAGT
CTTAAATAGTGATTAAATTTCTCTAGAAAGAAGTTAACAGCTCATTAGAAAAGTTTTAACC
TGTGAAATAAGTATTTTTCTCAACATTCTTTAAAGTTTTTATATAAGTTAACACTAGGTAA
ACATTCTGCATACTAGAAGTCAGTTTATTACAAATACATGTCAAAAATAAAGATTATACAA |

| SEQ ID No. | Description of Sequence (marker) | Sequence |
|---|---|---|
| | | GGCACCAAACTACTAGATTTGGCATTAAAACAAATGTTTATTTCTAATCACAACAAAATTA<br>TAATGAATAAATGTTCTTGCTTTGTATGGAAATACAATTCTTTATTAAAGTTAACAGAAAG<br>GAACTGATCGTTTGTACCAGTAAAAGAGAGAAACACACAGGTTAAATATCTTCTTGTGGGG<br>TTAAGGGGTAGAACCTATCTTGCCTTCACTCTCAAGATAACGACTCAAATTAAGCTTTTTG<br>AGCACCACTCTTGTGGGGACACACATACGCTGATCTAGGAATGAAATCTTCGTGGTCTCAA<br>TTCTAGATCTACTATGCCAGTTTCTCTCTGGCTTTAGCCTTTGAGAACCTGTATAAGAATA<br>CGTAAGTAATCCAGAGCTGTGAAGAGTTTAAAGGCCAACTTCTCCAGTGAACTCAACCTCT<br>GGGTCACTTGCAACCAGAAATTGGATACCTCATAATGATGCAGGAAAAGACCCGAGTTCATG<br>ATGAGTTTCAAAGGCCACGTTCATTTAGGAACCAACTCTCTCTGGATTTACCTGCTGAGTT<br>CCAGCAGCGTGATGGGCTGACATCCCACCTACAAGTATGACACCTGTGTAACACCAGCTAG<br>GTACGGCTGGAGAAGGCTGAAGAGAGAATGCCATTAAATGGAAGAATGTACTGATTGTAGT<br>GACCTTCTCCACACACACACACACACACACACACACACACCTACAGTAATACAGCAAGC<br>GTGGAATAATCAGCCAATATATAACATTCCATCAGTATTTTATTAAGGAAATAACCTGAAT<br>GTGGTTGATTTTGACATAGCTGCAATTACAGTTTTCTTCTATTTTTCAAGCCACAATAAGG<br>AAAATAAACTACTCATGGTCTAAATACTAGAGATAAAGTAGATTCATGGCTTGGTAAGGAA<br>ATTTTAAGCATTCCTTCAAAGATTGACGTGCTAAAATAAGCATTGATGTTTTGAGTTTTTT<br>TACACCTAGGATTTTTAGCTTGGGTGTGTAGGTGAAGGCCAAGACTCTCTGCAGGAAAAAG<br>CTTATTTTCAAACTCAGAAAATAAAATGTCAATCATAAAAATCTACTTCAACTTTAGCAAA<br>AAGAAAAAAAATCAACAAAAGTATACTCTGTATGCTGGGATTCCGAGGTTCCAACACAC<br>TGTTACAAATCTGTGGGGGTTTCTTTCTTCTGATAATTCTAGAGCCTGTTACCATAGAAA<br>GGCATTTCTTCAATGGCTGGTTGTAGTTAGTTCATGTTTTTCAATCAAATTTGCAAATGTA<br>TTTGTTGCTGTATAGTGATTGTTTTGCAAAATAAAATTGCTTGTCACCT |
| 2 | Map2 protein | MADERKDEAKAPHWTSAPLTEASAHSHPPEIKDQGGAGEGLVRSANGFPYREDEEGAFGEH<br>GSQGTYSNTKENGINGELTSADRETAEEVSARIVQVVTAEAVAVLKGEQEKEAQHKDQTAA<br>LPLAAEETANLPPSPPPSPASEQTVTVEEDLLTASKMEFHDQQELTPSTAEPSDQKEKESE<br>KQSKPGEDLKHAALVSQPETTKTYPDKKDMQGTEEEKAPLALFGHTLVASLEDMKQKTEPS<br>LVVPGIDLPKEPPTPKEQKDWFIEMPTEAKKDEWGLVAPISPGPLTPMREKDVFDDIPKWE<br>GKQFDSPMPSPFQGGSFTLPLDVMKNEIVTETSPFAPAFLQPDDKKSLQQTSGPATAKDSF<br>KIEEPHEAKPDKMAEAPPSEAMTLPKDAHIPVVEEHVMGKVLEEEKEAINQETVQQRDTFT<br>PSGQEPILTEKETELKLEEKTTISDKEAVPKESKPPKPADEEIGIIQTSTEHTFSEQKDQE<br>PTTDMLKQDSFPVSLEQAVTDSAMTSKTLEKAMTEPSALIEKSSIQELFEMRVDDKDKIEG<br>VGAATSAELDMPFYEDKSGMSKYFETSALKEEATKSIEPGSDYYELSDTRESVHESIDTMS<br>PMHKNGDKEFQTGKESQPSPPAQEAGYSTLAQSYPSDLPEEPSSPQERMFTIDPKVYGEKR<br>DLHSKNKDDLTLSRSLGLGGRSAIEQRSMSINLPMSCLDSIALGENFGRGHDLSPLASDIL<br>TNTSGSMDEGDDYLPATTPALEKAPCFPVESKEEEQIEKVKATGEESTQAEISCESPFLAK<br>DFYKNGTVMAPDLPEMLDLAGTRSRLASVSADAEVARRKSVPSETVVEDSRTGLPPVTDEN<br>HVIVKTDSQLEDLGYCVFNKYTVPLPSPVQDSENLSGESGTFYEGTDDKVRRDLATDLSLI<br>EVKLAAAGRVKDEFSVDKEASAHISGDKSGLSKEFDQEKKANDRLDTVLEKSEEHADSKEH<br>AKKTEEAGDEIETFGLGVTYEQALAKDLSIPTDASSEKAEKGLSSVPEIAEVEPSKKVEQG<br>LDFAVQGQLDVKISDFGQMASGLNIDDRRATELKLEATQDMTPSSKAPQEADAFMGVESGH<br>MKEGTKVSETEVKEKVAKPDLVHQEAVDKEESYESSGEHESLTMESLKADEGKKETSPESS<br>LIQDEIAVKLSVEIPCPPAVSEADLATDERADVQMEFIQGPKEESKETPDISITPSDVAEP<br>LHETIVSEPAEIQSEEEEIEAQGEYDKLLFRSDTLQITDLGVSGAREEFVETCPSEHKGVI<br>ESVVTIEDDFITVVQTTTDEGESGSHSVRFAALEQPEVERRPSPHDEEEFEVEEAAEAQAE<br>PKDGSPEAPASPEREEVALSEYKTETYDDYKDETTIDDSIMDADSLWVDTQDDDRSIMTEQ<br>LETIPKEEKAEKEARRSSLEKHRKEKPFKTGRGRISTPERKVAKKEPSTVSRDEVRRKKAV<br>YKKAELAKKTEVQAHSPSRKFILKPAIKYTRPTHLSCVRKTTAAGGESALAPSVFKQAKD<br>KVSDGVTKSPEKRSSLPRPSSILPPRRGVSGDRDENSFSLNSSISSSARRTTRSEPIRRAG<br>KSGTSTPTTPGSTAITPGTPPSYSSRTPGTPGTPSYPRTPHTPGTPKSAILVPSEKKVAII<br>RTPPKSPATPKQLRLINQPLPDLKNVSKIGSTDNIKYQPKGGQVQIVTKKIDLSHVTSKC<br>GSLKNIRHRPGGGRVKIESVKLDFKEKAQAKVGSLDNAHHVPGGGNVKIDSQKLNFREHAK<br>ARVDHGAEIITQSPGRSSVASPRRLSNVSSSGSINLLESPQLATLAEDVTAALAKQGL |
| 3 | TH mRNA | CGGACCTCCACACTGAGCCATGCCCACCCCCGACGCCACCACGCCACAGGCCAAGGGCTTC<br>CGCAGGGCCGTGTCTGAGCTGGACGCCAAGCAGGCAGAGGCCATCATGTCCCCGCGGTTCA<br>TTGGGCGCAGGCAGAGCCTCATCGAGGACGCCCGCAAGGAGCGGGAGGCGGCGGTGGCAGC<br>AGCGGCCGCTGCAGTCCCCTCGGAGCCCGGGGACCCCCTGGAGGCTGTGGCCTTTGAGGAG<br>AAGGAGGGGAAGGCCGTGCTAAACCTGCTCTTCTCCCCGAGGGCCACCAAGCCCTCGGCGC<br>TGTCCCGAGCTGTGAAGGTGTTTGAGACGTTTGAAGCCAAAATCCACCATCTAGAGACCCG<br>GCCCGCCCAGAGGCCGCGAGCTGGGGCCCCCACCTGGAGTACTTCGTGCGCCTCGAGGTG<br>CGCCGAGGGGACCTGGCCGCCCTGCTCAGTGGTGTGCGCCAGGTGTCAGAGGACGTGCGCA<br>GCCCCGCGGGGCCCAAGGTCCCCTGGTTCCCAAGAAAAGTGTCAGAGCTGGACAAGTGTCA<br>TCACCTGGTCACCAAGTTCGACCCTGACCTGGACTTGGACCACCCGGGCTTCTCGGACCAG<br>GTGTACCGCCAGCGCAGGAAGCTGATTGCTGAGATCGCCTTCCAGTACAGGCACGGCGACC<br>CGATTCCCCGTGTGGAGTACACCGCCGAGGAGATTGCCACCTGGAAGGAGGTCTACACCAC<br>GCTGAAGGGCCTCTACGCCACGCACGCCTGCGGGGAGCACCTGGAGGCCTTTGCTTTGCTG<br>GAGCGCTTCAGCGGCTACCGGGAAGACAATATCCCCCAGCTGGAGGACGTCTCCCGCTTCC<br>TGAAGGAGCGCACGGGCTTCCAGCTGCGGCCTGTGGCCGGCCTGCTGTCCGCCCGGGACTT<br>CCTGGCCAGCCTGGCCTTCCGCGTGTTCCAGTGCACCCAGTATATCCGCCACGCGTCCTCG<br>CCCATGCACTCCCCTGAGCCGGACTGCTGCCACGAGCTGCTGGGGCACGTGCCCATGCTGG<br>CCGACCGCACCTTCGCGCAGTTCTCGCAGGACATTGGCCTGGCGTCCCTGGGGGCCTCGGA<br>TGAGGAAATTGAGAAGCTGTCCACGCTGTACTGGTTCACGGTGGAGTTCGGGCTGTGTAAG<br>CAGAACGGGGAGGTGAAGGCCTATGGTGCCGGGCTGCTGTCCTCCTACGGGGAGCTCCTGC |

| SEQ ID No. | Description of Sequence (marker) | Sequence |
|---|---|---|
| | | ACTGCCTGTCTGAGGAGCCTGAGATTCGGGCCTTCGACCCTGAGGCTGCGGCCGTGCAGCC<br>CTACCAAGACCAGACGTACCAGTCAGTCTACTTCGTGTCTGAGAGCTTCAGTGACGCCAAG<br>GACAAGCTCAGGAGCTATGCCTCACGCATCCAGCGCCCCTTCTCCGTGAAGTTCGACCCGT<br>ACACGCTGGCCATCGACGTGCTGGACAGCCCCCAGGCCGTGCGGCGCTCCCTGGAGGGTGT<br>CCAGGATGAGCTGGACACCCTTGCCCATGCGCTGAGTGCCATTGGCTAGGTGCACGGCGTC<br>CCTGAGGGCCCTTCCCAACCTCCCCTGGTCCTGCACTGTCCCGGAGCTCAGGCCCTGGTGA<br>GGGGCTGGGTCCCGGGTGCCCCCATGCCCTCCCTGCTGCCAGGCTCCCACTGCCCCTGCA<br>CCTGCTTCTCAGCGCAACAGCTGTGTGTGCCCGTGGTGAGGTTGTGCTGCCTGTGGTGAGG<br>TCCTGTCCTGGCTCCCAGGGTCCTGGGGGCTGCTGCACTGCCCTCCGCCCTTCCCTGACAC<br>TGTCTGCTGCCCAATCACCGTCACAATAAAAGAAACTGTGGTCTCTA |
| 4 | TH protein | MPTPDATTPQAKGFRRAVSELDAKQAEAIMVRGQGAPGPSLTGSPWPGTAAPAASYTPTPR<br>SPRFIGRRQSLIEDARKEREAAVAAAAAAVPSEPGDPLEAVAFEEKEGKAVLNLLFSPRAT<br>KPSALSRAVKVFETFEAKIHHLETRPAQRPRAGGPHLEYFVRLEVRRGDLAALLSGVRQVS<br>EDVRSPAGPKVPWFPRKVSELDKCHHLVTKFDPDLDLDHPGFSDQVYRQRRKLIAEIAFQY<br>RHGDPIPRVEYTAEEIATWKEVYTTLKGLYATHACGEHLEAFALLERFSGYREDNIPQLED<br>VSRFLKERTGFQLRPVAGLLSARDFLASLAFRVFQCTQYIRHASSPMHSPEPDCCHELLGH<br>VPMLADRTFAQFSQDIGLASLGASDEEIEKLSTLYWFTVEFGLCKQNGEVKAYGAGLLSSY<br>GELLHCLSEEPEIRAFDPEAAAVQPYQDQTYQSVYFVSESFSDAKDKLRSYASRIQRPFSV<br>KFDPYTLAIDVLDSPQAVRRSLEGVQDELDTLAHALSAIG |
| 5 | Tuj1 mRNA | GACATCAGCCGATGCGAAGGGCGGGGCCGCGGCTATAAGAGCGCGCGGCCGCGGTCCCCGA<br>CCCTCAGCAGCCAGCCCGGCCCGCCCGCGCCCGTCCGCAGCCGCCCGCCAGACGCGCCCAG<br>TATGAGGGAGATCGTGCACATCCAGGCCGGCCAGTGCGGCAACCAGATCGGGGCCAAGTTC<br>TGGGAAGTCATCAGTGATGAGCATGGCATCGACCCCAGCGGCAACTACGTGGGCGACTCGG<br>ACTTGCAGCTGGAGCGGATCAGCGTCTACTACAACGAGGCCTCTTCTCACAAGTACGTGCC<br>TCGAGCCATTCTGGTGGACCTGGAACCCGGAACCATGGACAGTGTCCGCTCAGGGGCCTTT<br>GGACATCTCTTCAGGCCTGACAATTTCATCTTTGGTCAGAGTGGGGCCGGCAACAACTGGG<br>CCAAGGGTCACTACACGAGGGGGCGGAGCTGGTGGATTCGGTCCTGGATGTGGTGCGGAA<br>GGAGTGTGAAAACTGCGACTGCCTGCAGGGCTTCCAGCTGACCCACTCGCTGGGGGGCGGC<br>ACGGGCTCCGGCATGGGCACGTTGCTCATCAGCAAGGTGCGTGAGGAGTATCCCGACCGCA<br>TCATGAACACCTTCAGCGTCGTGCCCTCACCCAAGGTGTCAGACACGGTGGTGGAGCCCTA<br>CAACGCCACGCTGTCCATCCACCAGCTGGTGGAGAACACGGATGAGACCTACTGCATCGAC<br>AACGAGGCGCTCTACGACATCTGCTTCCGCACCCTCAAGCTGGCCACGCCCACCTACGGGG<br>ACCTCAACCACCTGGTATCGGCCACCATGAGCGGAGTCACCACCTCCTTGCGCTTCCCGGG<br>CCAGCTCAACGCTGACCTGCGCAAGCTGGCCGTCAACATGGTGCCCTTCCCGCGCCTGCAC<br>TTCTTCATGCCCGGCTTCGCCCCCCTCACAGCCCGGGGCAGCCAGCAGTACCGGGCCCTGA<br>CCGTGCCCGAGCTCACCCAGCAGATGTTCGATGCCAAGAACATGATGGCCGCCTGCGACCC<br>GCGCCACGGCCGCTACCTGACGGTGGCCACCGTGTTCCGGGGCCGCATGTCCATGAAGGAG<br>GTGGACGAGCAGATGCTGGCCATCCAGAGCAAGAACAGCAGCTACTTCGTGGAGTGGATCC<br>CCAACAACGTGAAGGTGGCCGTGTGTGACATCCCGCCCCGCGGCCTCAAGATGTCCTCCAC<br>CTTCATCGGGAACAGCACGGCCATCCAGGAGCTGTTCAAGCGCATCTCCGAGCAGTTCACG<br>GCCATGTTCCGGCGCAAGGCCTTCCTGCACTGGTACACGGGCGAGGGCATGGACGAGATGG<br>AGTTCACCGAGGCCGAGAGCAACATGAACGACCTGGTGTCCGAGTACCAGCAGTACCAGGA<br>CGCCACGGCCGAGGAAGAGGGCGAGATGTACGAAGACGACGAGGAGGAGTCGGAGGCCCAG<br>GGCCCCAAGTGAAGCTGCTCGCAGCTGGAGTGAGAGGCAGGTGGCGGCCGGGGCCGAAGCC<br>AGCAGTGTCTAAACCCCCGGAGCCATCTTGCTGCCGACACCCTGCTTTCCCCTCGCCCTAG<br>GGCTCCCTTGCCGCCCTCCTGCAGTATTTATGGCCTCGTCCTCCCCACCTAGGCCACGTGT<br>GAGCTGCTCCTGTCTCTGTCTTATTGCAGCTCCAGGCCTGACGTTTTACGGTTTTGTTTTT<br>TACTGGTTTGTGTTTATATTTTCGGGGATACTTAATAAATCTATTGCTGTCAGATACCCTT<br>AAAAAAAAAAAAAAAAAAAAAAAAA |
| 6 | Tuj1 protein | MREIVHIQAGQCGNQIGAKFWEVISDEHGIDPSGNYVGDSDLQLERISVYYNEASSHKYVP<br>RAILVDLEPGTMDSVRSGAFGHLFRPDNFIFGQSGAGNNWAKGHYTEGAELVDSVLDVVRK<br>ECENCDCLQGFQLTHSLGGGTGSGMGTLLISKVREEYPDRIMNTFSVVPSPKVSDTVVEPY<br>NATLSIHQLVENTDETYCIDNEALYDICFRTLKLATPTYGDLNHLVSATMSGVTTSLRFPG<br>QLNADLRKLAVNMVPFPRLHFFMPGFAPLTARGSQQYRALTVPELTQQMFDAKNMMAACDP<br>RHGRYLTVATVFRGRMSMKEVDEQMLAIQSKNSSYFVEWIPNNVKVAVCDIPPRGLKMSST<br>FIGNSTAIQELFKRISEQFTAMFRRKAFLHWYTGEGMDEMEFTEAESNMNDLVSEYQQYQD<br>ATAEEEGEMYEDDEEESEAQGPK |
| 7 | GFAP mRNA | ATCGCCAGTCTAGCCCACTCCTTCATAAAGCCCTCGCATCCCAGGAGCGAGCAGAGCCAGA<br>GCAGGATGGAGAGGAGACGCATCACCTCCGCTGCTCGCCGCTCCTACGTCTCCTCAGGGGA<br>GATGATGGTGGGGGGCCTGGCTCCTGGCCGCCGTCTGGGTCCTGGCACCCGCCTCTCCCTG<br>GCTCGAATGCCCCCTCCACTCCCGACCCGGGTGGATTTCTCCCTGGCTGGGGCACTCAATG<br>CTGGCTTCAAGGAGACCCGGGCCAGTGAGCGGGCAGAGATGATGGAGCTCAATGACCGCTT<br>TGCCAGCTACATCGAGAAGGTTCGCTTCCTGGAACAGCAAAACAAGGCGCTGGCTGCTGAG<br>CTGAACCAGCTGCGGGCCAAGGAGCCCACCAAGCTGGCAGACGTCTACCAGGCTGAGCTGC<br>GAGAGCTGCGGCTGCGGCTCGATCAACTCACCGCCAACAGCGCCCGGCTGGAGGTTGAGAG<br>GGACAATCTGGCACAGGACCTGGCCACTGTGAGGCAGAAGCTCCAGGATGAAACCAACCTG<br>AGGCTGGAAGCCGAGAACAACCTGGCTGCCATATAGACAGGAAGCAGATGAAGCCACCCTGG<br>CCCGTCTGGATCTGGAGAGGAAGATTGAGTCGCTGGAGGAGGAGATCCGGTTCTTGAGGAA<br>GATCCACGAGGAGGAGGTTCGGGAACTCCAGGAGCAGCTGGCCCGACAGCAGGTCCATGTG<br>GAGCTTGACGTGGCCAAGCCAGACCTCACCGCAGCCCTGAAAGAGATCCGCACGCAGTATG |

| SEQ ID No. | Description of Sequence (marker) | Sequence |
|---|---|---|
|  |  | AGGCAATGGCGTCCAGCAACATGCATGAAGCCGAAGAGTGGTACCGCTCCAAGTTTGCAGA<br>CCTGACAGACGCTGCTGCCCGCAACGCGGAGCTGCTCCGCCAGGCCAAGCACGAAGCCAAC<br>GACTACCGGCGCCAGTTGCAGTCCTTGACCTGCGACCTGGAGTCTCTGCGCGGCACGAACG<br>AGTCCCTGGAGAGGCAGATGCGCGAGCAGGAGGAGCGGCACGTGCGGGAGGCGGCCAGTTA<br>TCAGGAGGCGCTGGCGCGGCTGGAGGAAGAGGGGCAGAGCCTCAAGGACGAGATGGCCCGC<br>CACTTGCAGGAGTACCAGGACCTGCTCAATGTCAAGCTGGCCCTGGACATCGAGATCGCCA<br>CCTACAGGAAGCTGCTAGAGGGCGAGGAGAACCGGATCACCATTCCCGTGCAGACCTTCTC<br>CAACCTGCAGATTCGAGGGGGCAAAAGCACCAAAGACGGGGAAAATCACAAGGTCACAAGA<br>TATCTCAAAAGCCTCACAATACGAGTTATACCAATACAGGCTCACCAGATTGTAAATGGAA<br>CGCCGCCGGCTCGCGGTTAGCTGCCTGCCTCTCAGACACGGCGCTTTGCCCAGCTTGACAG<br>GGAGTGAGCCTCACCCACCCCATCCTCCCAATCCCCCTGAGTTCCCTCTTCCCAGGCTTCC<br>CCTAAAGGGCCTGGACTGCGTCATTTTCCCAGGAACTGCAGTGCCCAGCCCAGGACGTGGT<br>ACAGAGTAACTGTACATTAAACTGGCAGAGCTTGTTAGTGGTAAAGGTGGTGAGTCCTTGG<br>GTGCGCAGTGGAGCTGCTCTGGGGCCTCTGAGCAAGCAGCAGCCTCTGTCTCACCTCTTCC<br>TGTCACTGGGAGGGCCCCTTGGGTCTCGCTGTGCCTGGACGCCAGGCTCTCTGCTTTATTC<br>TTTCATCCCTGAGGCTCCATCGCTCAGCTCAGTGCTGACTCAGTTCAGAGGATTCTTCCCT<br>CAGGACCGCAGCTCTTGCAGTGAATAAAGTTTTATGTTCCCTGCTCTTAATGTTAAATATT<br>AAAAAAAAA |
| 8 | GFAP protein | MERRRITSAARRSYVSSGEMMVGGLAPGRRLGPGTRLSLARMPPPLPTRVDFSLAGALNA<br>GFKETRASERAEMMELNDRFASYIEKVRFPLEQQNKALAAELNQLRAKEPTKLADVYQAEL<br>RELRLRLDQLTANSARLEVERDNLAQDLATVRQKLQDETNLRLEAENNLAAYRQEADEAT<br>LARLDLERKIESLEEEIRFLRKIHEEEVRELQEQLARQQVHVELDVAKPDLTAALKEIRT<br>QYEAMASSNMHEAEEWYRSKFADLTDAAARNAELLRQAKHEANDYRRQLQSLTCDLESLR<br>GTNESLERQMREQEERHVREAASYQEALARLEEEGQSLKDEMARHLQEYQDLLNVKLALD<br>IEIATYRKLLEGEENRITIPVQTFSNLQIRETSLDTKSVSEGHLKRNIVVKTVEMRDGEV<br>IKESKQEHKDVM |
| 9 | S100b mRNA | GGGCAGAGGGAATAAGAGGCTGCCTCTGCCCACCAGTCCTGCCGCCCAGGACCCGCAGCAG<br>AGACGACGCCTGCAGCAAGGAGACCAGGAAGGGGTGAGACAAGGAAGAGGATGTCTGAGCT<br>GGAGAAGGCCATGGTGGCCCTCATCGACGTTTTCCACCAATATTCTGGAAGGGAGGGAGAC<br>AAGCACAAGCTGAAGAAATCCGAACTGAAGGAGCTCATCAACAATGAGCTTTCCCATTTCT<br>TAGAGGAAATCAAAGAGCAGGAGGTTGTGGACAAAGTCATGGAAACACTGGACAATGATGG<br>AGACGGCGAATGTGACTTCCAGGAATTCATGGCCTTTGTTGCCATGGTTACTACTGCCTGC<br>CACGAGTTCTTTGAACATGAGTGAGATTAGAAAGCAGCCAAACCTTTCCTGTAACAGAGAC<br>GGTCATGCAAGAAAGCAGACAGCAAGGGCTTGCAGCCTAGTAGGAGCTGAGCTTTCCAGCC<br>GTGTTGTAGCTAATTAGGAAGCTTGATTTGCTTTGTGATTGAAAAATTGAAAACCTCTTTC<br>CAAAGGCTGTTTTAACGGCCTGCATCATTCTTTCTGCTATATTAGGCCTGTGTGTAAGCTG<br>ACTGGCCCCAGGGACTCTTGTTAACAGTAACTTAGGAGTCAGGTCTCAGTGATAAAGCGTG<br>CACCGTGCAGCCCGCCATGGCCGTGTAGACCCTAACCCGGAGGGAACCCTGACTACAGAAA<br>TTACCCCGGGGCACCCTTAAAACTTCCACTACCTTTAAAAAACAAAGCCTTATCCAGCATT<br>ATTTGAAAACACTGCTGTTCTTTAAATGCGTTCCTCATCCATCAGATAACAGCTGGTTGG<br>CCGGTGTGGCCCTGCAAGGGCGTGGTGGCTTCGGCCTGCTTCCCGGGATGCGCCTGATCAC<br>CAGGTGAACGCTCAGCGCTGGCAGCGCTCCTGGAAAAAGCAACTCCATCAGAACTCGCAAT<br>CCGAGCCAGCTCTGGGGGCTCCAGCGTGGCCTCCGTGACCCATGCGATTCAAGTCGCGGCT<br>GCAGGATCCTTGCCTCCAACGTGCCTCCAGCACATGCGGCTTCCGAGGGCACTACCGGGGG<br>CTCTGAGCCACCGCGAGGGCCTGCGTTCAATAAAAAG |
| 10 | S100b protein | MSELEKAMVALIDVFHQYSGREGDKHKLKKSELKELINNELSHFLEEIKEQEVVDKVMETL<br>DNDGDGECDFQEFMAFVAMVTTACHEFFEHE |
| 11 | PAX6 protein | MQNSHSGVNQLGGVFVNGRPLPDSTRQKIVELAHSGARPCDISRILQVSNGCVSKILGRY<br>YETGSIRPRAIGGSKPRVATPEVVSKIAQYKRECPSIFAWEIRDRLLSEGVCTNDNIPSV<br>SSINRVLRNLASEKQQMGADGMYDKLRMLNGQTGSWGTRPGWYPGTSVPGQPTQDGCQQQ<br>EGGGENTNSISSNGEDSDEAQMRLQLKRKLQRNRTSFTQEQIEALEKEFERTHYPDVFAR<br>ERLAAKIDLPEARIQVWFSNRRAKWRREEKLRNQRRQASNTPSHIPISSSFSTSVYQPIP<br>QPTTPVSSFTSGSMLGRTDTALTNTYSALPPMPSFTMANNLPMQPPVPSQTSSYSCMLPT<br>SPSVNGRSYDTYTPPHMQTHMNSQPMGTSGTTSTGLISPGVSVPVQVPGSEPDMSQYWPR<br>LQ |
| 12 | SOX1 protein | MYSMMMETDLHSPGGAQAPTNLSGPAGAGGGGGGGGGGGGGAKANQDRVKRPMNAFMV<br>WSRGQRRKMAQENPKMHNSEISKRLGAEWKVMSEAEKRPFIDEAKRLALHMKEHPDYKY<br>RPRRKTKTLLKKDKYSLAGGLLAAGAGGGGAAVAMGVGVGVGAAAVGQRLESPGGAAGGG<br>YAHVNGWANGAYPGSVAAAAAAAAMMQEAQLAYGQHPGAGGAHPAHPAHPHHHPAHP<br>HNPQPMHRYDMGALQYSPISNSQGYMSASPSGYGGLPYGAAAAAAAAAGGAHQNSAVAA<br>AAAAAASSGALGALGSLVKSEPSGSPPAPAHSRAPCPGDLREMISMYLPAGEGGDPAAAA<br>AAAAQSRLHSLPQHYQGAGAGVNGTVPLTHI |
| 13 | SOX2 protein | MYNMMETELKPPGPQQTSGGGGNSTAAAAGGNQKNSPDRVKRPMNAFMVWSRGQRRKMA<br>QENPKMHNSEISKRLGAEWKLLSETEKRPFIDEAKRLALHMKEHPDYKYRPRRKTKTLM<br>KKDKYTLPGGLLAPGGNSMASGVGVGAGLGAGVNQRMDSYAHMNGWSNGSYSMMQDQLGY<br>PQHPGLNAHGAAQMQPMHRYDVSALQYNSMTSSQTYMNGSPTYSMSYSQQGTPGMALGSM<br>GSVVKSEASSSPPVVTSSSHSRAPCQAGDLRDMISMYLPGAEVPEPAAPSRLHMSQHYQS<br>GPVPGTAINGTLPLSHM |

| SEQ ID No. | Description of Sequence (marker) | Sequence |
|---|---|---|
| 14 | Nestin protein | MEGCMGEESFQMWELNRRLEAYLARVKALEEQNELLSAELGGLRAQSADTSWRAHADDEL AALRALVDQRWREKHAAEVARDNLAEELEGVAGRCQQLRLARERTTEEVARNRRAVEAEK CARAWLSSQVAELERELEALRVAHEEERVGLNAQAACAPRCPAPPRGPPAPAPEVEELAR RLGEAWRGAVRGYQERVAHMETSLGQARERLGRAVQGAREGRLELQQLQAERGGLLERRA ALEQRLEGRWQERLRATEKFQLAVEALEQEKQGLQSQIAQVLEGRQQLAHLKMSLSLEVA TYRTLLEAENSRLQTPGGGSKTSLSFQDPKLELQFPRTPEGRRLGSLLPVLSPTSLPSPL PATLETPVPAFLKNQEFLQARTPTLASTPIPPTPQAPSPAVDAEIRAQDAPLSLLQTQGG RKQAPEPLRAEARVAIPASVLPGPEEPGGQRQEASTGQSPEDHASLAPPLSPDHSSLEAK DGESGGSRVFSICRGEGEGQIWGLVEKETAIEGKVVSSLQQEIWEEEDLNRKEIQDSQVP LEKETLKSLGEEIQESLKTLENQSHETLERENQECPRSLEEDLETLKSLEKENKELLKDV EVVRPLEKEAVGQLKPTGKEDTQTLQSLQKENQELMKSLEGNLETFLFPGTENQELVSSL QENLESLTALEKENQEPLRSPEVGDEEALRPLTKENQEPLRSLEDENKEAFRSLEKENQE PLKTLEEEDQSIVRPLETENHKSLRSLEEQDQETLRTLEKETQQRRRSLGEQDQMTLRPP EKVDLEPLKSLDQEIARPLENENQEFLKSLKEESVEAVKSLETEILESLKSAGQENLETL KSPETQAPLWTPEEINQGAMNPLEKEIQEPLESVEVNQETFRLLEEENQESLRSLGAWNL ENLRSPEEVDKESQRNLEEEENLGKGEYQESLRSLEEEGQELPQSADVQRWEDTVEKDQE LAQESPPGMAGVENEDEAELNLREQDGFTGKEEVVEQGELNATEEVWIPGEGHPESPEPK EQRGLVEGASVKGGAEGLQDPEGQSQQVGAPGLQAPQGLPEATEPLVEDDVAPGGDQASP EVMLGSEPAMGESAAGAEPGPGQGVGGLGDPGHLTREEVMEPPLEEESLEAKRVQGLEGP RKDLEEAGGLGTEFSELPGKSRDPWEPPREGREESEAEAPRGAEEEAFPAETLGHTGSDAP SPWPLGSEEAEEDVPPVLVSPSPTYTPILEDAPGPQPQAEGSQEASWGVQGRAEALGKVE SEQEELGSGEIPEGPQEEGEESREESEEDELGETLPDSTPLGFYLRSPTSPRWDPTGEQR PPPQGETGKEGWDPAVLASEGLEAPPSEKEEGEEGEEECGRDSDLSEEFEDLGTEAPFLP GVPGEVAEPLGQVPQLLLDPAAWDRDGESDGFADEEESGEEGEEDQEEGREPGAGRWGPG SSVGSLQALSSSQRGEFLESDSVSVSVPWDDSLRGAVAGAPKTALETESQDSAEPSGSEE ESDPVSLEREDKVPGPLEIPSGMEDAGPGADIIGVNGQGPNLEGKSQHVNGGVMNGLEQS EEVGQGMPLVSEGDRGSPFQEEEGSALKTSWAGAPVHLGQGQFLKFTQREGDRESWSSGE D |
| 15 | LMXA1 protein | MLDGLKMEENFQSAIDTSASFSSLLGRAVSPKSVCEGCQRVILDRFLLRLNDSFWHEQCV QCASCKEPLETTCFYRDKKLYCKYDYEKLFAVKCGGCFEAIAPNEFVMRAQKSVYHLSCF CCCVCERQLQKGDEFVLKEGQLLCKGDYEKERELLSLVSPAASDSGKSDDEESLCKSAHG AGKGTAEEGKDHKRPKPRTILTTQQRRAFKASFEVSSKPCRKVRETLAAETGLSVRVVQ VWFQNQRAKMKKLARRQQQQQDQQNTQRLSSAQTNGGGSAGMEGIMNPYTALPTPQQLL AIEQSVYSSDPFRQGLTPPQMPGDHMHPYGAEPLFHDLDSDDTSLSNLGDCFLATSEAGP LQSRVGNPIDHLYSMQNSYFTS |
| 16 | FOXA2 protein | MLGAVKMEGHEPSDWSSYYAEPEGYSSVSNMNAGLGMNGMNTYMSMSAAAMGSGSGNMSA GSMNMSSYVGAGMSPSLAGMSPGAGAMAGMGGSAGAAGVAGMGPHLSPSLSPLGGQAAGA MGGLAPYANMNSMSPMYGQAGLSRARDPKTYRRSYTHAKPPYSYISLITMAIQQSPNKML TLSEIYQWIMDLFPFYRQNQQRWQNSIRHSLSFNDCFLKVPRSPDKPGKGSFWTLHPDSG NMFENGCYLRRQKRFKCEKQLALKEAAGAAGSGKKAAAGAQASQAQLGEAAGPASETPAG TESPHSSASPCQEHKRGGLGELKGTPAAALSPPEPAPSPGQQQQAAAHLLGPPHHPGLPP EAHLKPEHHYAFNHPFSINNLMSSEQQHHSHHHHQPHKMDLKAYEQVMHYPGYGSPMPG SLAMGPVTNKTGLDASPLAADTSYYQGVYSRPIMNSS |
| 17 | LMX1B protein | MDIATGPESLERCFPRGQTDCAKMLDGIKMEEHALRPGPATLGVLLGSDCPHPAVCEGCQ RPISDRFLMRVNESSWHEECLQCAACQQALTTSCYFRDKLYCKQDYQQLFAAKCSGCME KIAPTEFVMRALECVYHLGCFCCCVCERQLRKGDEFVLKEGQLLCKGDYEKEKDLLSSVS PDESDSVKSEDEDGDMKPAKGQGSQSKGSGDDGKDPRRPKRPRTILTTQQRRAFKASFEV SSKPCRKVRETLAAETGLSVRVVQVWFQNQRAKMKKLARRHQQQEQQNSQRLGQEVLSS RMEGMMASYTPLAPPQQQIVAMEQSPYGSSDPFQQGLTPPQMPGDHMNPYGNDSIFHDID SDTSLTSLSDCFLGSSDVGSLQARVGNPIDRLYSMQSSYFAS |
| 18 | NURR1 protein | MPCVQAQYGSSPQGASPASQSYSYHSSGEYSSDFLTPEFVKFSMDLTNTEITATTSLPSF STFMDNYSTGYDVKPPCLYQMPLSGQQSSIKVEDIQMHNYQQHSLPPQSEEMMPHSGSV YYKPSSPPTPTTPGFQVQHSPMMWDDPGSLHNFHQNYVATTHMIEQRKTPVSRLSLFSFKQ SPPGTPVSSCQMRFDGPLHVPMNPEPAGSHHVVDGQTFAVPNPIRKPASMGFPGLQIGHA SQLLDTQVPSPPRGSPSNEGLCAVCGDNAACQHYGVRTCEGCKGFFKRTVQKNAKYVCL ANKNCPVDKRRRNRCQYCRFQKCLAVGMVKEVVRTDSLKGRRGRLPSKPKSPQEPSPPSP PVSLISALVRAHVDSNPAMTSLDYSRFQANPDYQMSGDDTQHIQQFYDLLTGSMEIIRGW AEKIPGFADLPKADQDLLFESAFLELFVLRLAYRSNPVEGKLIFCNGVVLHRLQCVRGFG EWIDSIVEFSSNLQNMNIDISAFSCIAALAMVTERHGLKEPKRVEELQNKIVNCLKDHVT FNNGGLNRPNYLSKLLGKLPELRTLCTQGLQRIFYLKLEDLVPPPAIIDKLFLDTLPF |
| 19 | AADC protein | MNASEFRRRGKEMVDYMANYMEGIEGRQVYPDVEPGYLRPLIPAAAPQEPDTFEDIINDV EKIIMPGVTHWHSPYFFAYFPTASSYPAMLADMLCGAIGCIGFSWAASPACTELETVMMD WLGKMLELPKAFLNEKAGEGGGVIQGSASEATLVALLAARTKVIHRLQAASPELTQAAIM EKLVAYSSDQAHSSVERAGLIGGVKLKAIPSDGNFAMRASALQEALERDKAAGLIPFFMV ATLGTTTCCSFDNLLEVGPICNKEDIWLHVDAAYAGSAFICPEFRHLLNGVEFADSFNFN PHKWLLVNFDCSAMWVKKRTDLTGAFRLDPTYLKHSHQDSGLITDYRHWQIPLGRRFRSL KMWFVFRMYGVKGLQAYIRKHVQLSHEFESLVRQDPRFEICVEVILGLVCFRLKGSNKVN EALLQRINSAKKIHLVPCHLRDKFVLRFAICSRTVESAHVQRAWEHIKELAADVLRAERE |

-continued

| SEQ ID No. | Description of Sequence (marker) | Sequence |
|---|---|---|
| 20 | EN1 protein | MEEQQPEPKSQRDSALGAAAAATPGGLSLSLSPGASGSSGSGSDGDSVPVSPQPAPPSPP AAPCLPPLAHHPHLPPHPPPPPPQHLAAPAHQPQPAAQLHRTTNFFIDNILRPDFGCKKE QPPPQLLVAAAARGGAGGGGRVERDRGQTAAGRDPVHPLGTRAPGAASLLCAPDANCGPP DGSQPAAAGAGASKAGNPAAAAAAAAAVAAAAAAAAAKPSDTGGGGSGGGAGSPGAQGT KYPEHGNPAILLMGSANGGPVVKTDSQQPLVWPAWVYCTRYSDRPSSGPRTRKLKKKKNE KEDKRPRTAFTAEQLQRLKAEFQANRYITEQRRQTLAQELSLNESQIKIWFQNKRAKIKK ATGIKNGLALHLMAQGLYNHSTTTVQDKDESE |

THE FIGURES SHOW

FIG. 1: Generation and application of hiPSCs. Somatic cells, taken from a patient, are cultured. By adding the four pluripotency factors OCT4, SOX2, C-MYC & KLF4, the somatic cells are reprogrammed into pluripotent stem cells. These hiPSCs could be used in patient-specific cell replacement therapies, drug screening tests or serve as human disease model. (Yamanaka and Blau, 2010).

Figure 2:
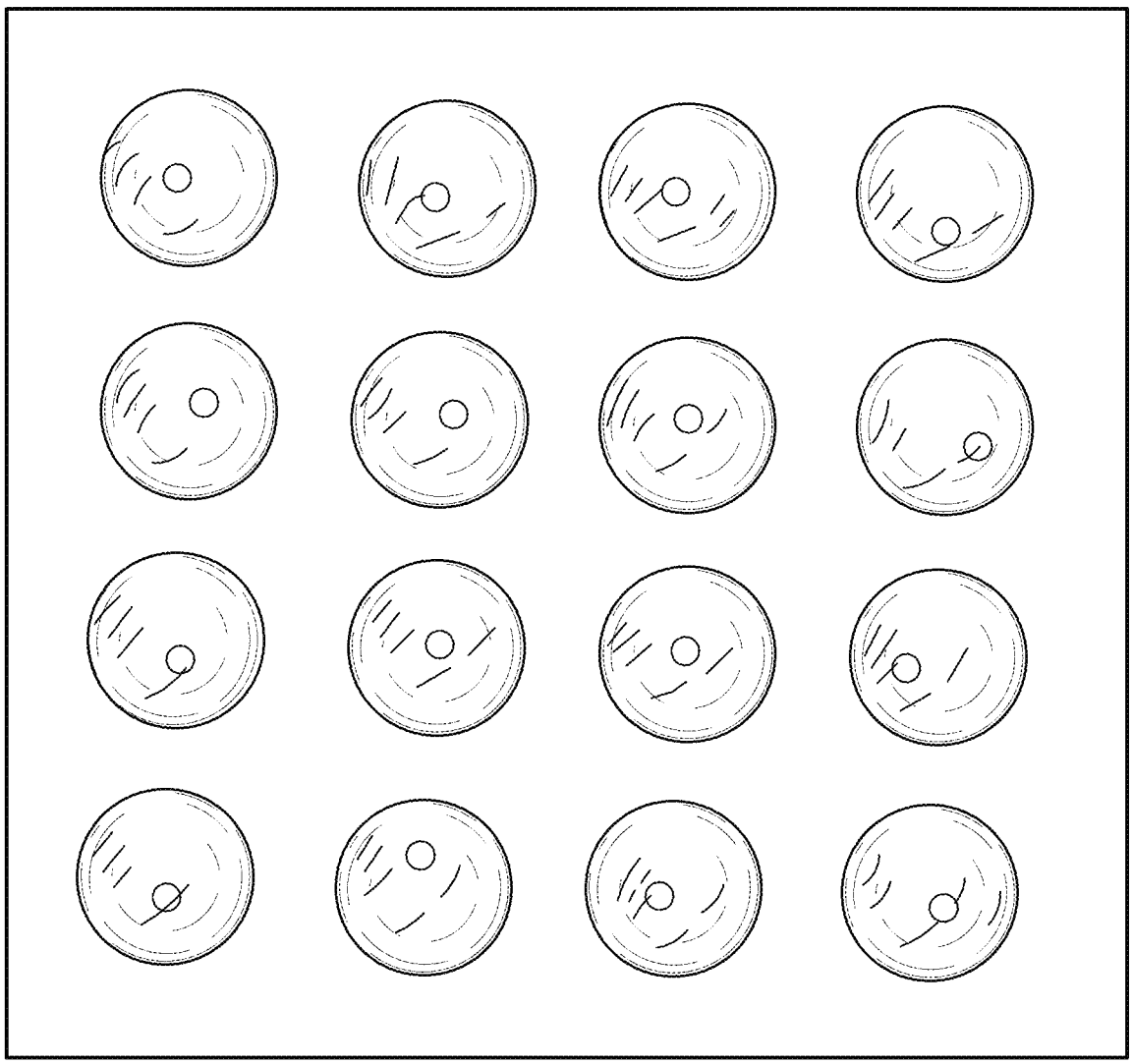

FIG. 2: A Square of Parafilm containing MATRIGEL droplets. Neuroepithelial tissue was placed in the centre of a Parafilm dimple and covered with liquid MATRIGEL.

FIG. 3: Confocal image of hNESCs cultured under two-dimensional conditions. hNESCs expressed the neural progenitor markers SOX1, SOX2, and NESTIN. The ability of hNESCs to spontaneous differentiation is demonstrated by ICC with antibodies raised against neuronal markers TUJ1 and DCX. FOXA2 staining reveals a low expression level of ventral neural tube marker. Nuclei are counterstained with Hoechst. Scale bars, 20 µm.

FIG. 4: Progression of midbrain organoid development from human NESCs. (a) A colony of human NESCs seeded on round-bottom ultralow attachment plates after six days. Colonies are globular and have bright and smooth edges. (b) An organoid at day 9, after embedding in MATRIGEL, shows darker tissue in the centre and bright tissue at the edge. The arrow indicates MATRIGEL surrounding the organoid. (c) Image of an organoid at day 13, two days under differentiation conditions. Small processes start to develop across the whole surface. Scale bars, 500 µm. (d) 5× magnification of a midbrain organoid at day 35 showing long processes that expand from the tissue. (e) 10× magnification of the same organoid. Arrowheads indicate cell bodies outside the colony. (f) An organoid without MATRIGEL (left, arrow) and an organoid embedded in MATRIGEL (right, arrowhead), showing long processes that expand through the whole MATRIGEL matrix. Bright field images were acquired with an inverted microscope. Scale bar, 500 µm (a-d).

FIG. 5: Immunofluorescence staining of early midbrain organoids. (a) Image of an early organoids at day 6 with markers for neural progenitor cells (SOX2) and young neurons (TUJ1). Arrowheads indicate early differentiated neurons. (b) An early organoid at day 7, expressing the neural progenitor markers NESTIN and SOX2. Nuclei are counterstained with Hoechst. Scale bars, 50 µm.

FIG. 6: Dopaminergic neurons in midbrain organoids. (a) Immunofluorescence staining of an early organoid at day 16 with antibodies against DA neurons (TH/TUJ1, arrowheads). (b) Tile scan of an organoid at day 30 expressing DA neuron markers. (c) Higher magnification of the tile scan in b. Nuclei are counterstained with Hoechst. Scale bars, 50 µm (a,c), 500 µm (b).

FIGS. 7A and B: Young and mature dopaminergic neurons in midbrain organoids. (a) Tile scan of an organoid expressing the neural progenitor marker SOX2, as well as the young DA neuronal markers TUJ1/TH. (b) Higher magnification of the tile scan in a. Arrows indicate the assumed migration direction of maturing DA neurons basally away from the proliferative zone. (c) Tile scan of an organoid expressing mature DA neuronal markers MAP2/TH. The dashed line marks the apical surface containing mostly neural progenitor cells. Arrow: Assumed direction of DA neuron migration upon maturation (d) Higher magnification of the tile scan in c. Arrowheads mark mature DA neurons. Nuclei are counterstained with Hoechst. Scale bar, 500 µm (a,c), 500 µm (b,d).

FIGS. 8A and B: Presence of glial cells in midbrain organoids. (a) Tile scan of a midbrain organoid stained for markers of young neurons (TUJ1), oligodendrocytes (O4), and astrocytes (GFAP). (b) Higher magnification of a. Arrowheads mark O4 positive and TUJ1 negative cells, indicating oligodendrocytes. (c) 63× image of another organoid showing a staining of O4 positive and TUJ1 negative cells (arrowheads). (d) GFAP and O4 positive and TUJ1 negative cell reveals differentiation of glia. Nuclei are counterstained with Hoechst. Scale bars, 500 µm (a), 50 µm (b-d).

FIG. 9. Derivation of midbrain-specific organoids from human neuroepithelial stem cells. (a) Procedure of midbrain organoid culture system. Details are described in the methods section (item 2.1 of the Examples). hNESC, human neuroepithelial stem cell; AA, ascorbic acid, PMA, purmorphamine. (b) Immunohistological staining for the cell proliferation marker Ki67 at day 27 and day 44 of the organoid culture reveals a decrease in the amount of proliferative cells in the midbrain organoids. (c) Immunohistological staining at day 27 and day 44 for the neural stem cell marker SOX2. SOX2 expression becomes more regionally restricted at the later stages. Scale bars, 200 µm (b, c); 150 µm section (c, lower panel). Dashed lines indicate the perimeter of the organoid.

FIG. 10. Neuronal differentiation and self-organization in midbrain organoids. (a) Whole-mount immunohistological staining of an organoid at day 27 for the DN markers TUJ1 and TH. (b) Higher magnification of (a). (c) Immunohistological staining for the mDA neuron markers FOXA2 and TH at day 61 reveals the midbrain identity of hNESC-derived organoids. (d) Higher magnification of (c). (e) High magnification of LMX1A/TH-positive mDA neurons in midbrain-specific organoids. (f-g) qRT-PCR analysis for the mDN markers AADC, TH, NURR1 (f) and EN1, LMX1A, LMX1B (g) at day 48. Error bars indicate the standard deviation from 3 independent cultures. (h-i) Asymmetry analysis of DNs. Immunostaining of DA neurons for TUJ1 and TH (h) was analyzed based on fluorescence intensities using a 3D surface plot (i). (j) Immunohistological staining for dopamine, MAP2 and TH reveals the presence of dopamine producing neurons. 150 μm sections (c, h). Scale bars, 200 μm (a, c, h), 20 μm (b, d, e, j).

FIG. 11. Differentiation into glia cells and formation of synaptic connections. (a) Immunohistological staining for the astrocytic markers S100I3 and GFAP in early-(day 27) and late-stage (day 61) organoids. Dashed lines indicate the perimeter of the organoid. (b) Higher magnification of (a) at day 61 showing astrocytes expressing S100I3 and GFAP. (c) Immunohistological staining of an organoid at day 61 revealing robust differentiation into CNPase-positive oligodendrocytes. Three-dimensional surface reconstructions of confocal z-stacks visualized the formation of myelin sheaths that enwrap TUJ1-positive neurites (arrowheads) as well as the formation of nodes of Ranvier that are suggested by the presence of gaps of CNPase-positive ensheathment. (d) Immunohistological staining of the presynaptic marker synaptophysin and the postsynaptic marker PSD95 at day 61. Arrowheads indicate a direct contact between a pre- and a postsynapse. Dashed box indicates the region of magnification. Images show the 3D view of a confocal z-stack. (e) Three-dimensional surface reconstructions of confocal z-stacks demonstrate the formation of synaptic connections between different neurites of an organoid as indicated by several direct contacts (arrowheads) between the pre- and postsynaptic markers synaptophysin and PSD95, respectively. Lower panels show high magnifications of a 3D view of a confocal z-stack and the corresponding 3D surface reconstruction of several synaptic connections. Scale bars, 200 μm (a), 20 μm (b, c upper panel, c lower panel left, d upper/middle panel left/middle), 2 μm (c lower panel right, d upper/middle panel right, d lower panel).

FIG. 12. Midbrain organoids reveal electrophysiological activity. a)-b) Monitoring of the spontaneous electrophysiological activity in an organoid using Fluo-4AM based calcium imaging. (a) Mean fluorescence frame of a calcium imaging dataset of a midbrain organoid with two segmented neurons expressing spontaneous activity. Scale bar, 20 μm. (b) Fluorescence traces corresponding to the segmented cell bodies in (a) showing firing patterns with pacemaking-like shape. (c)-(f) Evaluation of the spontaneous activity in midbrain organoids after 60-70 days using a multielectrode array (MEA) system. (c) Representative scheme of positioned midbrain organoid on a 16-electrode array in a 48-well tissue culture plate. (d) Representative image of the activity map. (e) Examples of mono- and biphasic spikes detected by individual electrodes. (f) Representative image of a spike raster plot showing neuronal network activity in time and space. Spikes occurring on multiple electrodes, closely in time, represent network synchrony, indicated by red lines.

EXAMPLES

I. Material and Methods
1. Cell Culture

Cell culture work was performed under sterile conditions using a laminar flow hood. All cells were cultured in an incubator at constant 37° C. and 5% $CO_2$. For cells that were grown under 2D conditions, cell culture plates (NUNC™, THERMO SCIENTIFIC™) were coated with MATRIGEL® (CORNING) resuspended in cold Knockout DMEM (LIFE TECHNOLOGIES). 1.5 ml of diluted MATRIGEL was added to each well of a 6-well-plate. The plates were kept at room temperature (RT) overnight. Coated plates were stored at 4° C. for up to one month.

2. Generation of Cerebral Organoids

Cerebral organoids were generated according to the established protocol by Lancaster et al. (Lancaster and Knoblich, 2014a; Lancaster et al., 2013) with slight modifications. Feeder-independent human iPS cells were used as a starting population instead of feeder-dependent iPSCs. As an initial step, embryoid bodies (EBs) were generated. These 3D aggregates undergo cell specification through differentiation into the three germ lineages endoderm, mesoderm, and ectoderm, similar to the embryonic development described in Section 1.1 of the Introduction. Next, the formation of neuroepithelial tissue was initiated, restricting the cell fate to the neural lineage. Once the neuroepithelial tissue developed, the 3D structures were transferred to droplets of MATRIGEL, which gives structural support and helps the tissue to maintain its 3D shape. This matrix, derived from the Engelbroth-Holm-Swarm mouse sarcoma, is composed of laminin, collagen IV, nidogen/enactin, and proteoglycan, thus resembling the extracellular matrix (ECM). The MATRIGEL-embedded tissue was cultured in medium that favoured neuronal differentiation by using Neurobasal medium supplemented with N2 and B27 containing vitamin A. Non-essential amino acids and GlutaMax™ were added in order to increase cell growth and viability. The reducing agent 2-Mercaptoethanol prevented the formation of toxic oxygen radical levels. The tissue was kept under dynamic conditions to prevent the tissue from attaching to the bottom. It further increases the nutrient exchange and controls waste product exchange. For this purpose, Lancaster et al. used a spinning bioreactor. In this project, the tissue was kept in a non-treated 10 cm cell culture petri dish (GREINER) on an orbital shaker (IKA®), spinning at around 80 rpm.

2.1 Maintenance of Human Induced Pluripotent Stem Cells

A wild type human induced pluripotent stem cell line from CORIELL was seeded on a cell culture 6-well-plate and cultured in Essential8™-medium (LIFE TECHNOLOGIES). At 70-80% confluence and within one week after the last seeding, cells were passaged. To detach the cells from the surface, the medium was aspirated and 0.5 mM EDTA (INVITROGEN) was added. After an incubation time of 4 min at 37° C. and 5% $CO_2$, EDTA was aspirated. Cells were washed with PBS, and resuspended in Essential8™-medium. Cells were seeded into a new coated 6-well-plate in a ratio of 1:3-1:6. Medium was changed every day.

2.2 Immunocytochemical Characterisation of hiPSCs

Human iPS cells were seeded on cover slips in a 24-well-plate and cultured under the conditions described in section 2.1. After three days, cells were fixed with 4% paraformaldehyde (PFA) for 40 min at 4° C. and washed three times with PBS for 5 min. The cell membrane was permeabilised with 0.2% Triton-X-100 at RT for 10 min. After three washing steps with 0.05% Triton-X-100 in PBS, cells were blocked with 2% NGS+2% BSA in 0.05% Triton-X-100 in PBS at RT for 60 min. Primary antibodies were diluted in the blocking buffer (see Table 1). 35 μl drops of primary antibody solution were prepared on Parafilm in a wet chamber. Cover slips were placed upside down on the drops and incubated at 4° C. overnight.

TABLE 1

Primary antibodies used for hiPSC ICC

| Antibody | Host | Company | Dilution |
|---|---|---|---|
| Anti-OCT4 | Rabbit | ABCAM | 1:400 |
| Anti-SSEA-4 | Mouse | MILLIPORE | 1:75 |
| Anti-NANOG | Rabbit | MILLIPORE | 1:200 |
| Anti-TRA-1-81 | Mouse | COVANCE | 1:50 |
| Anti-SOX2 | Rabbit | ABCAM | 1:200 |
| Anti-TRA-1-60 | Mouse | MILLIPORE | 1:50 |

The next day, the cover slips were washed with three changes of PBS for 5 min. Secondary antibodies raised against primary antibodies (Table 2) were diluted together with Hoechst dye (INVITROGEN, 1:10000) and drops on Parafilm were prepared as before. The cover slips were incubated for 1 h at RT and then washed three times with PBS, once with $H_2O$, and mounted on glass slides using fluorescence mounting medium. The stainings were analysed using a confocal laser scanning microscope (ZEISS LSM 710).

TABLE 2

Secondary antibodies used for hiPSC/hNESC ICC

| Antibody | Host | Company | Dilution |
|---|---|---|---|
| Anti-RABBIT-568 | Goat | INVITROGEN | 1:1000 |
| Anti-MOUSE-488 | Goat | INVITROGEN | 1:1000 |
| Anti-MOUSE-568 | Goat | INVITROGEN | 1:1000 |
| Anti-RABBIT-488 | Goat | INVITROGEN | 1:1000 |

2.3 Generation of EBs

For the generation of EBs, colonies were washed once with PBS and detached using 0.5 mM EDTA (INVITROGEN). After an incubation period of 4 min at 37° C., EDTA was replaced by 1 ml pre-warmed StemPro® Accutase® (LIFE TECHNOLOGIES) and cells were incubated for another 4 min at 37° C. The colonies were detached from the dish using a 1 ml pipette tip with 1 ml of Essential8™-medium (LIFE TECHNOLOGIES). The cell suspension was transferred to a Falcon tube and triturated in order to create a single cell suspension. Two repetitions of 5 µl were collected for cell counting. While the cells were centrifuged at 270 g for 5 min at RT, cells were counted using an automated cell counter (Countess II FL LIFE TECHNOLOGIES) with trypan blue. After centrifugation, the supernatant was aspirated and cells were resuspended in 1 ml low-FGF2 hESC medium containing ROCK inhibitor (Table 3). Next, low-FGF2 hESC medium was added in order to obtain 9000 live cells per 150 µl. Finally, 150 µl were plated to each well of a round-bottom ultralow attachment 96-well-plate (CORNING), which allows the cells to settle down and favours the formation of EBs. Cells were cultured in an incubator at 37° C. and 5% $CO_2$. Medium was changed every other day by replacing half of the medium with fresh low-FGF2 hESC medium. ROCK inhibitor and low-FGF2 were added only for four days.

TABLE 3 low-FGF2 hESC medium

| Substance | Concentration |
|---|---|
| DMEM-F12/Knockout-Serum replacement (LIFE TECHNOLOGIES) | 4:1 |
| ESC-quality FBS (INVITROGEN) | 1:300 |
| MEM-NEAA (LIFE TECHNOLOGIES) | 1:100 |
| GlutaMax (INVITROGEN) | 20 mM |
| 2-Mercaptoethanol (GIBCO) | 3.85 µM |
| Y-27632 ROCK inhibitor (MERCK) - 4 days | 50 µM |
| FGF2 (PEPROTECH) - 4 days | 4 ng/ml |

2.4 Neural induction

After six days, EBs with smooth edges that brightened at the border were transferred with a cut pipette tip to an ultralow attachment 24-well-plate (CORNING) containing neural induction medium (Table 4) and cultured for four days.

TABLE 4

Neural induction medium

| DMEM-F12 (LIFE TECHNOLOGIES) supplemented with: | Concentration |
|---|---|
| N2 Supplement (LIFE TECHNOLOGIES) | 1:100 |
| MEM-NEAA (LIFE TECHNOLOGIES) | 1:100 |
| Heparin (SIGMA) | 1 µg/ml |

2.5 Transferring Neuroepithelial Tissue to MATRIGEL Droplets

To prepare a substrate that helps to generate MATRIGEL droplets, a square of Parafilm was placed over an empty tip tray for 200 µl pipette tips and small dimples were created by pressing a gloved finger into the Parafilm over the holes. The dimpled Parafilm was sprayed once again with ethanol and dried in a petri dish under the laminar flow hood. Once the Parafilm was dry, Neuroepithelial tissue was transferred into each dimple and the medium was gently removed. Next, 30 µl of MATRIGEL was added carefully and the tissue was placed in the centre of the droplet (FIG. 2.1). To allow the MATRIGEL to polymerise, it was incubated at 37° C. for 30 min. After the incubation time, the droplets were collected in 15 ml cerebral organoid differentiation medium without vitamin A (Table 5). To remove the MATRIGEL droplets from Parafilm, sterile forceps were used to hold the sheet while shaking the dish gently until the drops fell off. The dish was kept in an incubator under static conditions and the medium was changed after 48 h. After four days in static culture, the medium was changed again with fresh differentiation medium containing vitamin A. Finally, the dishes were placed on an orbital shaker installed in the incubator, shaking at approximately 80 rpm, and medium was changed every third or fourth day.

TABLE 5

Cerebral organoid differentiation medium

| Substance | Concentration Static | Concentration Dynamic |
|---|---|---|
| DMEM-F12/Neurobasal (LIFE TECHNOLOGIES) | 1:1 | 1:1 |
| N2 Supplement (LIFE TECHNOLOGIES) | 1:200 | 1:200 |
| Insulin solution (SIGMA) | 1:4000 | 1:4000 |
| MEM-NEAA (LIFE TECHNOLOGIES) | 1:200 | 1:200 |
| GlutaMax (INVITROGEN) | 20 mM | 20 mM |

TABLE 5-continued

Cerebral organoid differentiation medium

| Substance | Concentration | |
|---|---|---|
| | Static | Dynamic |
| 2-Mercaptoethanol (GIBCO) | 192.5 nM | 192.5 nM |
| Penicillin (LIFE TECHNOLOGIES) | 100 U/ml | 100 U/ml |
| Streptomycin (LIFE TECHNOLOGIES) | 100 µg/ml | 100 µg/ml |
| B27 supplement w/o vitamin A (LIFE TECHNOLOGIES) | 1:100 | — |
| B27 supplement with vitamin A (LIFE TECHNOLOGIES) | — | 1:100 |

3. Generation of Midbrain Organoids 3.1 Human Neuroepithelial Stem Cells

To generate midbrain organoids, human neuroepithelial stem cells (hNESCs) served as a starting population. These neural progenitor cells have properties of stem cells, as they are capable of a robust, immortal expansion and can differentiate into cells of the CNS, including neurons, astrocytes, oligodendrocytes, and also into neural crest lineages. They solely require small molecules for self-renewal and expansion. Neural induction was initiated through the inhibition of non-neural BMP and dorsalising TGF-β signalling. To maintain the immortal self-renewal state, WNT and SHH signals were triggered. WNT signalling induces the formation of cells at the lateral border of the neural plate, while its antagonist SHH specifies ventral neural tube fates. CHIR99021 was used to stimulate the canonical WNT signalling pathway, and purmorphamine (PMA) was added to stimulate the SHH pathway. hNESCs can be efficiently differentiated into motor neurons and mDAs, designating them as a powerful tool to study early human development and neurodegenerative diseases.

3.2 Maintenance of Human Neuroepithelial Stem Cells

A wildtype human neuroepithelial stem cell line (hNESC-K7) that was derived from human induced pluripotent stem cells served as a starting population (Reinhardt et al., 2013). Cells were cultured in freshly supplemented N2B27 maintenance medium (Table 6 and Table 7). Cells were passaged at 80-90% confluence and within one week after the last seeding. To detach the cells from the surface, the medium was replaced by 700 µl warm StemPro® Accutase® (LIFE TECHNOLOGIES) and cells were incubated at 37° C. and 5% CO$_2$ for 4-6 min. Cells were resuspended in 5 ml warm DMEM/F12 (LIFE TECHNOLOGIES) and centrifuged at 200 g for 3 min. After aspirating the supernatant, the pellet was resuspended in supplemented N2B27-maintenance medium and cells were seeded into a new plate in a ratio of 1:10-1:20, depending on the confluence. Medium was changed every other day.

TABLE 6

N2B27 medium composition

| Substance | Concentration |
|---|---|
| DMEM-F12/Neurobasal (LIFE TECHNOLOGIES) | 1:1 |
| Penicillin (LIFE TECHNOLOGIES) | 100 U/ml |
| Streptomycin (LIFE TECHNOLOGIES) | 100 µg/ml |
| L-Glutamine (LIFE TECHNOLOGIES) | 20 mM |
| B27 supplement w/o vitamin A (LIFE TECHNOLOGIES) | 1:100 |
| N2 supplement (LIFE TECHNOLOGIES) | 1:200 |

TABLE 7

N2B27 maintenance medium composition

| N2B27 supplemented with: | Concentration |
|---|---|
| CHIR-99021 (AXON MEDCHEM) | 3 µM |
| PMA (ENZO LIFE SCIENCE) | 0.75 µM |
| AA (SIGMA) | 150 µM |

3.3 Immunocytochemical Characterisation of hNESCs hNESCs were seeded on cover slips in a 24-well-plate and cultured under the conditions described in Section 3.2. After 3 days, cells were fixed with 4% PFA for 40 min at 4° C. and washed three times with PBS for 5 min. ICC was performed according to the protocol described in Section 2.2 with different primary antibodies (Table 8) and the according secondary antibodies (Table 2).

TABLE 8

Primary antibodies used for hNESC ICC

| Antibody | Host | Company | Dilution |
|---|---|---|---|
| Anti-SOX2 | Rabbit | ABCAM | 1:200 |
| Anti-FOXA2 | Mouse | SANTA CRUZ | 1:100 |
| Anti-SOX1 | Rabbit | CELL SIGNALLING | 1:200 |
| Anti-NESTIN | Mouse | BD | 1:600 |
| Anti-DCX | Rabbit | ABCAM | 1:400 |
| Anti-TUJ1 | Mouse | COVANCE | 1:600 |

3.4 Generation and Expansion of Three-Dimensional hNESC Colonies

In order to generate single 3D hNESC colonies, hNESCs were passaged as described in section 3.2. After centrifugation and resuspension in 1 ml N2B27 maintenance medium, cells were counted using an automated cell counter (Countess II FL LIFE TECHNOLOGIES) with trypan blue. N2B27 maintenance medium was added in order to obtain 9000 live cells per 150 µl. 150 µl were plated to each well of a round-bottom ultralow attachment 96-well-plate (CORNING), which allows the cells to form one single colony per well. Medium was changed every other day by replacing half of the medium with fresh N2B27 maintenance medium. After six days, the colonies were transferred to an ultralow attachment 24-well-plate (CORNING) in order to remove side colonies and to allow the tissue to expand. After two days, the colonies were embedded into MATRIGEL droplets in the same manner as described in Section 2.5. The MATRIGEL-embedded colonies were cultured for two more days under static maintenance conditions in 10 cm petri-dishes, before differentiation was initiated at day 10 with N2B27 differentiation medium containing PMA (Table 9). The differentiation protocol was adapted from Reinhardt et al. 2013 with a slight modification. FGF8 was not added for the first eight days, since this decreases the differentiation efficiency into mDA neurons. After two days under differentiation conditions, the dishes were placed on an orbital shaker and kept under dynamic conditions at approximately 80 rpm. Medium was changed every third or fourth day. PMA was only added the first six days of differentiation.

TABLE 9

N2B27 differentiation medium

| N2B27 supplemented with: | Concentration |
|---|---|
| hBDNF (PEPROTECH) | 10 ng/ml |
| hGDNF (PEPROTECH) | 10 ng/ml |
| dbcAMP (PEPROTECH) | 500 μM |
| AA (SIGMA) | 200 μM |
| TGF-β3 (PEPROTECH) | 1 ng/ml |
| PMA (ENZO LIFE SCIENCE) | 1 μM |

4. Immunohistochemical Characterisation of Human Cerebral and Midbrain Organoids During brain development, cells rearrange themselves and form different functional and interdependent regions. Simultaneously, neuroepithelial cells differentiate into the various neurons and supportive glial cells of the CNS. In order to analyse whether cerebral and midbrain organoids develop different cell types and brain regions characteristic of the developing human brain, immunohistochemical (IHC) stainings were performed. The presence of neural progenitor cells, young and mature neurons, astrocytes, oligodendrocytes, dopaminergic neurons was analysed. Moreover, immunofluorescence stainings were performed to verify whether cerebral and midbrain organoids established midbrain identity.

4.1 Sectioning

At day 6 (n=3), 7 (n=3), 16 (n=3), 30 (n=3), and 44 (n=8), cerebral and midbrain organoids were fixed in 4% PFA at RT on a shaker overnight. Bigger organoids with a diameter >900 μm were sectioned prior to IHC. The fixed tissue was washed three times in PBS for 15 min and embedded into warm 3% low-melting point agarose and allowed to cool until solid. The block of agarose was then trimmed and glued on a metal block holder, and sectioned using a vibratome (Leica, VT100 S) to 150 μm thickness at a speed of 0.5 mm/s and a frequency of 70 Hz.

4.2 IHC

The free floating agarose sections were collected in 24-well-plates containing TBS+++(lx Tris-buffered saline with 0.5% Triton-X-100, 0.1% sodium azide, 0.1% sodium citrate and 5% fetal bovine serum or normal goat serum) and blocked/permeabilised for at least 1 h at RT on a shaker. Primary antibodies (see Table 10) were diluted in TBS+++ and 300 μl of the antibody solution were added to each well. The sections were incubated for 48 h at 4° C. on a shaker and afterwards washed with three changes of TBS for 15 min. The sections were incubated in secondary antibodies (see Table 11) diluted in TBS+++ for 2 h at RT on a shaker, which was followed by three washing steps in TBS for 15 min. Finally, the sections were rinsed with $H_2O$ and mounted with mounting medium on a glass slide. The stainings were analysed using a confocal laser scanning microscope (Zeiss LSM 710).

TABLE 10

Primary antibodies used for IHC

| Antibody | Host | Company | Dilution |
|---|---|---|---|
| Day 7: | | | |
| Anti-NESTIN | Mouse | BD | 1:600 |
| Anti-OCT4 | Rabbit | ABCAM | 1:400 |
| Anti-SOX2 | Rabbit | ABCAM | 1:200 |
| Anti-SSEA4 | Mouse | MILLIPORE | 1:75 |
| Anti-TRA-1-60 | Mouse | MILLIPORE | 1:50 |
| Day 16, Day 30: | | | |
| Anti-PAX6 | Rabbit | SANTA CRUZ | 1:300 |
| Anti-TH | Rabbit | ABCAM | 1:1000 |
| Day 6, Day 16, Day 30, Day 44: | | | |
| Anti-SOX2 | Goat | R&D | 1:200 |
| Anti-TUJ1 | Mouse | COVANCE | 1:600 |
| Day 44: | | | |
| Anti-EN1 | Goat | SANTA CRUZ | 1:100 |
| Anti-FOXA2 | Mouse | SANTA CRUZ | 1:100 |
| Anti-GFAP | Chicken | MILLIPORE | 1:1000 |
| Anti-LMX1 | Rabbit | MILLIPORE | 1:200 |
| Anti-MAP2 | Mouse | MILLIPORE | 1:200 |
| Anti-O4 | Mouse | SIGMA ALDRICH | 1:400 |
| Anti-TH | Rabbit | SANTA CRUZ | 1:1000 |
| Anti-TUJ1 | Rabbit | COVANCE | 1:600 |

TABLE 11

Secondary antibodies used for IHC

| Antibody | Host | Company | Dilution |
|---|---|---|---|
| Anti-Mouse-488 | Donkey | INVITROGEN | 1:1000 |
| Anti-Goat-568 | Donkey | INVITROGEN | 1:1000 |
| Anti-Rabbit-647 | Donkey | INVITROGEN | 1:1000 |
| Anti-Rabbit-488 | Goat | INVITROGEN | 1:1000 |
| Anti-Rabbit-568 | Goat | INVITROGEN | 1:1000 |
| Anti-Mouse-488 | Goat | INVITROGEN | 1:1000 |
| Anti-Mouse-568 | Goat | INVITROGEN | 1:1000 |
| Anti-Mouse-647 | Goat | INVITROGEN | 1:1000 |
| Anti-Chicken-568 | Goat | INVITROGEN | 1:1000 |

II. Results

1. Generation of Midbrain Organoids 1.1 Immunocytochemical Characterisation of hNESCs ICC of human neuroepithelial stem cells revealed a stable expression of the neural progenitor markers SOX2 and NESTIN under maintenance conditions. Another neural progenitor marker, SOX1, was also expressed in hNESCs, though fluorescence intensities varied. FOXA2, a marker of the ventral neural tube, was slightly expressed in hNESCs. Upon early differentiation, few hNESCs differentiate into neurons that express neuron-specific class III beta-tubulin (TUJ1) and doublecortin (DCX), which mark early neurons (FIG. 3).

1.2 Development of Midbrain Organoids

For the generation of midbrain organoids, the wild type hNESC line K7 was used as a starting population. Human NESCs seeded on round-bottom ultralow attachment plates formed dense globular colonies with only few dead cells around. In some wells, small side colonies developed, which then merged with the main colony after some days. The colonies began to brighten within the first three days and showed smooth edges under maintenance conditions, indicating healthy tissue. However, early organoids at day 8 developed a dark core in the centre, indicative of cell death. (FIG. 4 a, b). After two days of differentiation, the organoids developed small processes along the surface of the tissue (FIG. 4 c). Within three weeks, the processes expanded and reached a length of approximately 1 mm with only few cell bodies outside the colony. This was not observed in colonies without Matrigel support (FIG. 4 d-f).

1.3 Immunohistochemical Characterisation of Human Midbrain Organoids

Early midbrain organoids at day 6 and day 7 under maintenance conditions were stained without sectioning. The developing three dimensional human NESC colonies showed a stable expression of the neural progenitor markers SOX2 and NESTIN, as well as early differentiated young neurons (FIG. 5). Throughout the colonies, small cavities enclosed by radially organised progenitor cells developed.

Midbrain organoids at later stages under differentiation conditions developed a dense neuronal network, which gradually increased in complexity, consistent with gross morphological changes. Immunofluorescence staining with markers of dopaminergic neurons (TUJ1/TH) revealed that already at day 16 some DA neurons developed, increasing in density with later stages. Notably, DA neurons were located in distinct areas, which is suggestive of an asymmetric polar organisation of the 3D structures, consistent with brain development in vivo (FIG. 6, FIG. 7). To further analyse DA neurons in midbrain organoids, staining for the mature neuronal marker MAP2 together with TH was performed. A staining of different sections of the same organoid revealed that mature neurons were located at the outermost part of the organoid, while young TUJ1 positive neurons were more abundant in the inner core (FIG. 7 $a$, $c$). Interestingly, some of the mature neurons also expressed TH, revealing the presence of mature DA neurons in midbrain organoids. Additionally, staining for neural progenitor marker SOX2 showed that some neural progenitor cells surrounded the inner core of the organoid at later stages. TH positive DA neurons were located adjacent to the layer of neural precursor cells (FIG. 7).

To further examine the cellular organisation of midbrain organoids, stainings of glial cell markers including GFAP (astrocytes) and O4 (oligodendrocytes) were performed. In some regions of midbrain organoids, O4 positive and TUJ1 negative cells were identified, indicating the development of oligodendrocytes in late-stage midbrain organoids (FIG. 8 $a$-$c$). Only few astrocytes were found in midbrain organoids. However, some GFAP positive processes without associated cell bodies were observed across the tissue (FIG. 8 $c$), as well as few GFAP positive cells (FIG. 8 $d$)

Finally, midbrain organoids at later stages were stained for midbrain markers LMX1A, FOXA2, and EN1. Within the analysed sections and organoids, no cells expressing these transcription factors were found. Some cells showed evidence of LMX1A expression, though it was not located in the nucleus and diffuse, potentially revealing non-specific binding. Altogether the data indicate that midbrain organoids develop various neural cell types and exhibit an asymmetric polarisation of the tissue.

2. Further Generation of Human Midbrain-Specific Organoids

2.1 Materials and Methods

2.1.1 Midbrain Organoid Culture

The hiPSC-derived hNESCs were cultured as previously described (Reinhardt, et al. "Derivation and expansion using only small molecules of human neural progenitors for neurodegenerative disease modeling." *PloS one* 8, e59252). On day 0 of the organoid culture, hNESCs at passage <20 were treated with accutase for 5 min at 37° C., followed by gentle pipetting to generate single cells. A total of 9000 cells were seeded into each well of an ultra-low attachment 96-well round bottom plate (Corning) and cultured in N2B27 media supplemented with 3 µM CHIR-99021 (Axon Medchem), 0.75 µM purmorphamine (Enzo Life Science) and 150 µM ascorbic acid (Sigma) (referred to as N2B27 maintenance media). N2B27 medium consists of DMEM-F12 (Invitrogen)/Neurobasal (Invitrogen) 50:50 with 1:200 N2 supplement (Invitrogen), 1:100 B27 supplement lacking Vitamin A (Invitrogen), 1% L-glutamine and 1% penicillin/streptomycin (Invitrogen). The medium was changed every other day for 6 days, and 3D colonies were then transferred to ultra-low attachment 24-well plates (Corning) and cultured in N2B27 maintenance media.

On day 8 of the organoid culture, the 3D colonies were transferred to droplets of hESC-qualified Matrigel (BD Bioscience) as previously described (Lancaster and Knoblich (2014) "Generation of cerebral organoids from human pluripotent stem cells." *Nature protocols* 9, 2329-2340). Droplets were cultured in N2B27 maintenance media either in 10-cm Petri dishes for short-term cultures or in ultra-low attachment 24-well plates (Corning) with one droplet per well for long-term cultures. On day 10, differentiation was initiated with N2B27 media supplemented with 10 ng/ml hBDNF (Peprotech), 10 ng/ml hGDNF (Peprotech), 500 µM dbcAMP (Peprotech), 200 µM ascorbic acid (Sigma), and 1 ng/ml TGF-83 (Peprotech). Additionally, 1 µM purmorphamine (Enzo Life Science) was added to this medium for an additional 6 days. On day 14 of the organoid culture, the plates were placed on an orbital shaker (IKA), rotating at 80 rpm, in an incubator (5% $CO_2$, 37° C.) and the organoids were kept in culture with media changes every second or third day.

2.1.2 Immunohistochemical Analysis

Organoids were fixed with 4% paraformaldehyde overnight at RT and washed 3× with PBS for 1 h. Afterwards, they were embedded in 3% low-melting point agarose in PBS and incubated for 15 min at 37° C., followed by 30 minutes incubation at RT. The solid agarose block was covered with PBS and kept overnight at 4° C. If not indicated otherwise, 50 µm sections were cut using a vibratome (Leica VT1000s), and sections were permeabilized with 0.5% Triton X-100 in PBS and blocked in 2.5% normal goat or donkey serum with 2.5% BSA, 0.1% Triton X-100, and 0.1% sodium azide. Sections were incubated on a shaker for 48-72 h at 4° C. with primary antibodies in the blocking buffer at the following dilutions: rabbit anti-TH (1:1000, Abcam), chicken anti-TH (1:1000, Abcam), rabbit anti-TH (1:1000, Santa Cruz Biotechnology), goat anti-SOX2 (1:200, R&D Systems), rabbit anti-SOX2 (1:100, Abcam), goat anti-SOX1 (1:100, R&D Systems), mouse anti-nestin (1:200, BD), mouse anti-Ki67 (1:200, BD), rabbit anti-CC3 (1:200, Cell Signalling), mouse anti-FOXA2 (1:250, Santa Cruz Biotechnology), rabbit anti-LMX1A (1:200, Abcam), chicken anti-GFAP (1:1000, Millipore), mouse anti-S100β (1:1000, Abcam), mouse anti-TUJ1 (1:600, Covance), rabbit anti-TUJ1 (1:600, Covance), chicken anti-TUJ1 (1:600 Millipore), rabbit anti-PAX6 (1:300, Covance), mouse anti-synaptophysin (1:50 Abcam), rabbit anti PSD-95 (1:300, Invitrogen), mouse anti-MAP2 (1:200, Millipore), mouse anti-CNPase (1:200, Abcam), and mouse anti-O4 (1:400, Sigma). After incubation with the primary antibodies, sections were washed three times in 0.05% Triton X-100 and blocked for 30 min at RT on a shaker, followed by incubation with the secondary antibodies in 0.1% Triton X-100 (1:1000). All secondary antibodies (Invitrogen) were conjugated to Alexa Fluor fluorochromes. Dopamine was detected using a STAINperfect Immunostaining Kit (ImmuSmol) according to manufacturer's protocol. Sections were co-stained with chicken anti-TH primary antibody (Abcam), and nuclei were counterstained with Hoechst 33342 (Invitrogen). Sections were mounted in Fluoromount-G mounting medium (Southern Biotech) and analyzed with a confocal laser scanning microscope (Zeiss LSM 710). Images were further processed with Zen Software (Zeiss) and ImageJ. Three-dimensional surface reconstructions of confocal z-stacks were created using Imaris software (Bitplane). The asymmetric distribution of DNs was assessed based on fluorescence intensities with the ImageJ Interactive 3D surface plot plugin.

2.1.3 Quantitative Real-Time PCR

Total RNA was isolated from 48 days-old organoids. Typically, five organoids were pooled for one isolation. For dissociation, the organoids were washed once with PBS and lysed with QIAzol lysis reagent (Qiagen), passed through a needle three times and homogenized with QIAshredder columns (Qiagen). RNA was isolated using the RNeasy Mini Kit (Qiagen) according to the manufacturer's instructions. Subsequently, isolated RNA was reverse-transcribed following the protocol of the High Capacity RNA to DNA Kit (Thermo Fisher Scientific). Quantitative real-time polymerase chain reactions (qRT-PCRs) were conducted with the Maxima SYBR Green qPCR Master Mix (Thermo Scientific). Amplification of 1 µg cDNA was performed in an AriaMx Real-time PCR System (Agilent Technologies) as follows: An initial denaturing step, 10 min at 95° C., 40 cycles of denaturation for 15 s at 95° C., annealing for 30 s at 60° C., and elongation for 30 s at 72° C. The expression levels were normalized relative to the expression of the housekeeping gene RPL37A using the comparative Ct-method 2-ΔΔCt. To evaluate the expression patterns of midbrain organoids, the values were compared to the expression levels of hNESCs, which were set to 1. The quality of the PCR products was assessed by melting curve analysis.

2.1.4 Evaluation of Electrophysiological Activity

Calcium imaging and multielectrode array (MEA) recording was used to analyze the spontaneous activity of organoids at day 50-52 and day 60-70, respectively. A concentration of 5 µM cell permeant Fluo-4 AM (Life Technologies) in a neurobasal medium was added to the well and incubated for 45 min at 37° C. on an orbital shaker. Fluorescent images were acquired using a live cell spinning disk confocal microscope (Zeiss) equipped with a CMOS camera (Orca Flash 4.0, Hamamatsu). Calcium time-series were acquired at 5 Hz for approximately 2 min and stored as single images. These images were analyzed using the ADINA toolbox (Diego et al. (2013) "Automated identification of neuronal activity from calcium imaging by sparse dictionary learning." Proceedings of the IEEE 10th International Symposium on Biomedical Imaging, pp. 1058-1061), which is publicly available software that has been developed to automatically segment individual cell bodies and separate the overlapping ones. Fluorescent traces, expressed as relative changes in the fluorescence intensity (ΔF/F), were then measured for segmented cell bodies.

MEA recording was conducted using the Maestro system from Axion BioSystems. A 48-well MEA plate containing a 16-electrode array per well was precoated with 0.1 mg/ml poly-D-lysine hydrobromide (Sigma-Aldrich) and subsequently coated with 10 µg/ml laminin (Sigma-Aldrich) for 1 h at room temperature (RT). Midbrain organoids were placed onto the array after day 60-70. A coverslip was placed on top to ensure the contact of the free floating organoid with the electrodes. Spontaneous activity was recorded at a sampling rate of 12.5 kHz for 5 min for up to five days at 37° C. in neuronal maturation media. Using Axion Integrated Studio (AxIS 2.1), a Butterworth band pass filter with 200-3000 Hz cutoff frequency and a threshold of 6×SD were set to minimize both false-positives and missed detections. The Neural Metric Tool (Axion BioSystems) was used to analyze the spike raster plots. Electrodes with an average of spikes/min were defined as active. The spike count files generated from the recordings were used to calculate the number of spikes/active electrode/measurement. Further details regarding the MEA system were previously described (Bardy et al. (2015) "Neuronal medium that supports basic synaptic functions and activity of human neurons in vitro." Proceedings of the National Academy of Sciences of the United States of America 112, E2725-2734).

2.2 Results

Previously described neuroepithelial stem cells (Reinhardt et al. "Derivation and expansion using only small molecules of human neural progenitors for neurodegenerative disease modeling." PloS one 8, e59252) were used as the starting population for the generation of human midbrain organoids. Compared to iPSCs as a starting population, NESCs are already patterned towards midbrain/hindbrain identity.

Typically, NESCs express the neural progenitor markers SOX1, SOX2, PAX6, and NESTIN prior to organoid generation. Cells were seeded on round-bottom ultralow adhesion 96-well plates enabling the cells to form three-dimensional colonies. They were cultured in the presence of the GSK3b inhibitor CHIR99021 to stimulate the canonical WNT signaling pathway, and the SHH pathway was activated using purmorphamine (PMA). On day 8, the three-dimensional NESC colonies were embedded into droplets of Matrigel for structural support, and two days after, specification into midbrain organoids was initiated by changing the media to differentiation media. We kept the organoids in 10 cm Petri dishes for short-term cultures or in ultralow adhesion 24-well plates for long-term cultures and placed them on an orbital shaker rotating at approximately 80 rpm (FIG. 9A).

Figures 9A, 9B:
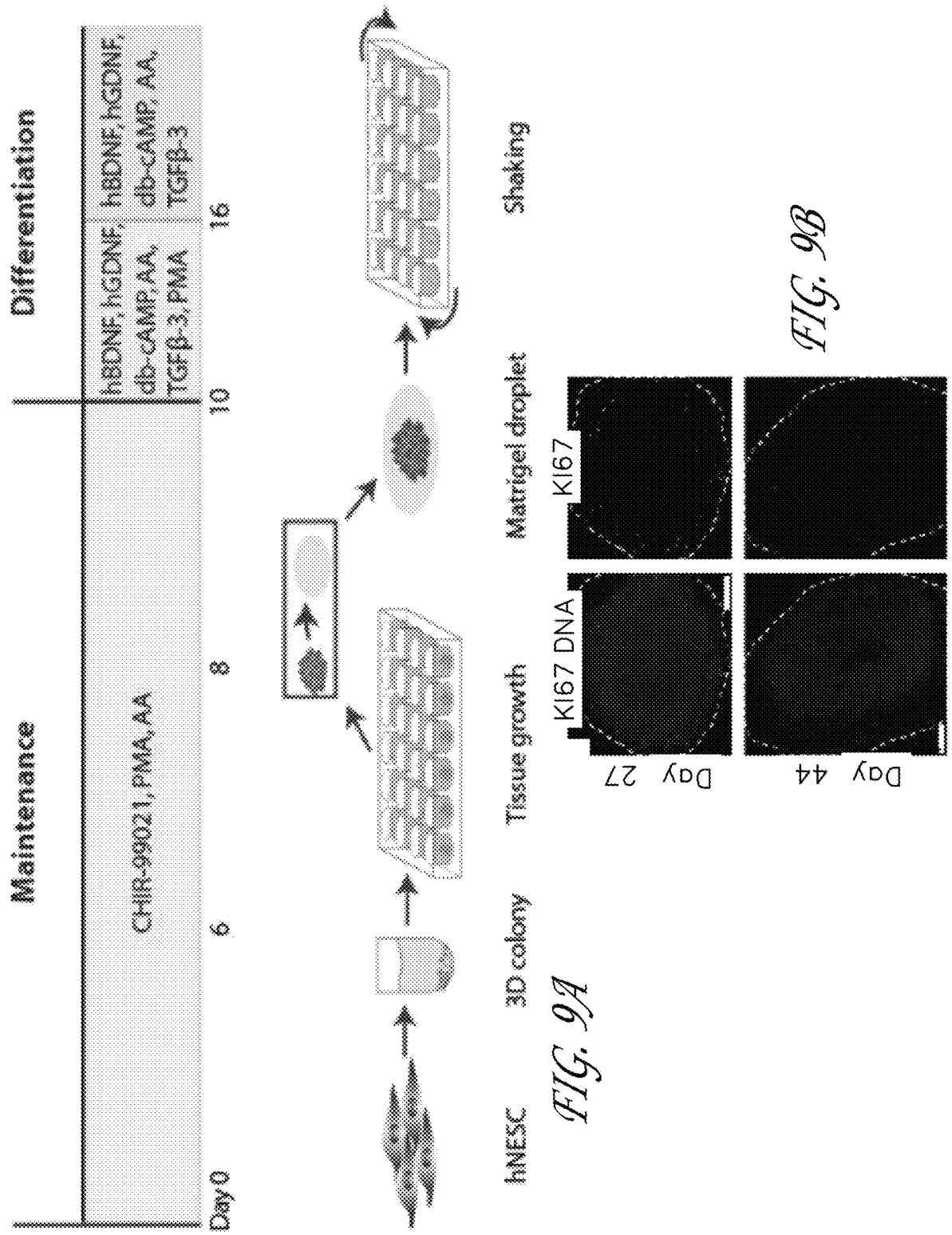
Figure 9C:
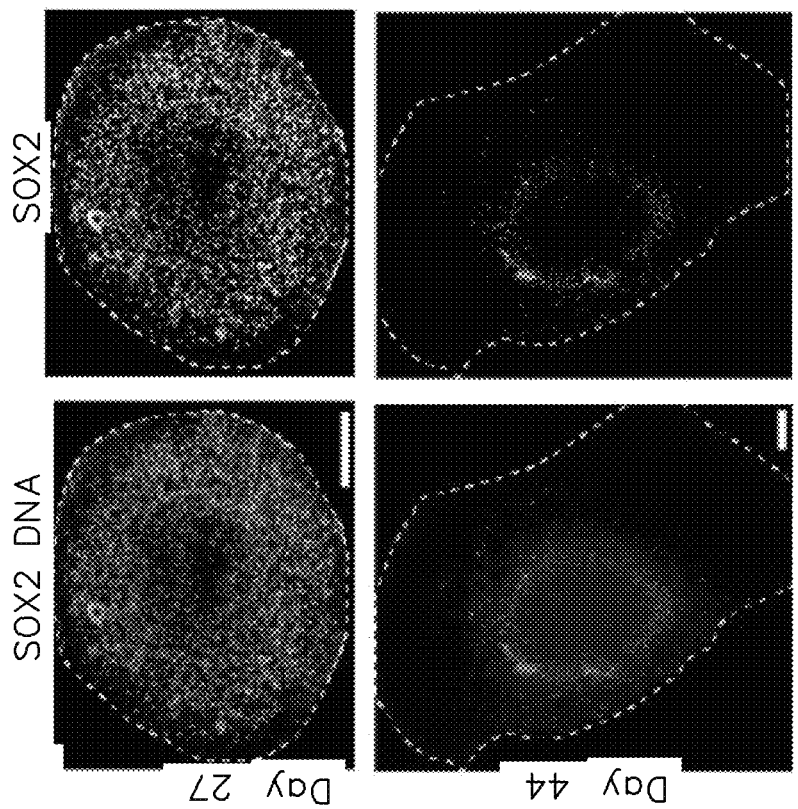

After about 27 days of the whole procedure (after about 16 days of differentiation into midbrain organoids), the early midbrain organoids widely expressed the cell proliferation marker Ki67, which decreased upon maturation (FIG. 9B). Furthermore, these organoids expressed the neural progenitor marker SOX2, which also decreases during maturation and becomes more regionally restricted, resembling the formation of a stem cell niche (FIG. 9C). Importantly, the generation of midbrain organoids from NESCs could be reproduced without significant variation.

2.1 Neuronal Differentiation and Self-Organization of Human Neuroepithelial Stem Cell Derived Midbrain Organoids After showing a decrease of proliferation and stem cell identity, neuronal differentiation and specification of midbrain dopaminergic neurons (mDNs) was assessed. Robust differentiation into TUJ1 positive neurons and TH positive DNs could be observed. These stainings revealed the formation of a complex neuronal network (FIG. 10A, 2B). Double-positive staining of the mature neuronal marker MAP2/TH demonstrated the maturation of DNs within the organoids. It was further examined whether NESC-derived organoids undergo differentiation into DNs with midbrain identity. In late-stage organoids, a large population of TH-, LMX1A-, and FOXA2-positive neurons was observed (FIG. 10C-E). qRT-PCR further revealed the upregulation of mDN differentiation markers, including LMX1A, LMX1B, EN1, NURR1, AADC, and TH (FIG. 10F, 10G). These data indicate that the obtained dopaminergic neurons indeed have midbrain identity.

Figure 10H:
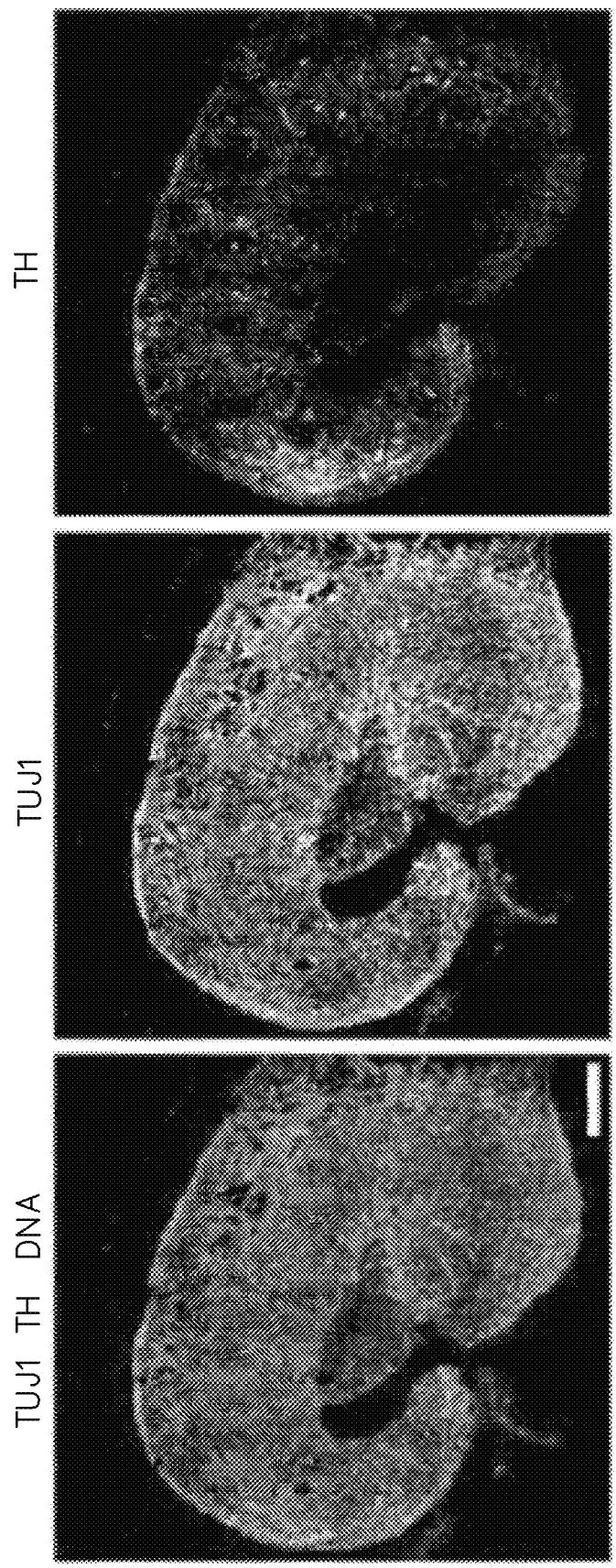

To examine the degree of spatial organization in NESC-derived midbrain organoids, we evaluated the distribution pattern DA neuronal markers TUJ1/TH and depicted the results using surface plots. Strikingly, we found that DA neurons form clearly specified clusters within midbrain organoids (FIG. 10H, 10I).

Figure 10J:
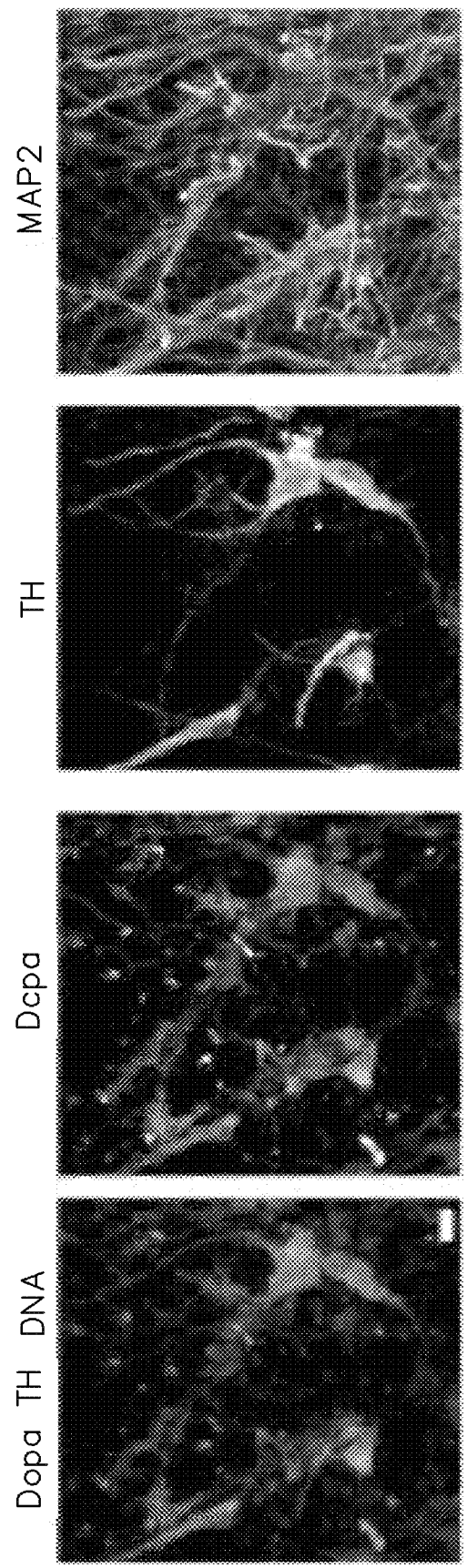

To further demonstrate the identity of TH positive neurons as dopaminergic, we analyzed their ability to produce the neurotransmitter dopamine. Immunostainings of mature organoids demonstrated the presence of dopamine and TH-double positive cells (FIG. 10J). These results indicated that mDNs of NESC-derived organoids self-organize into a complex, spatially patterned and functional neuronal tissue.

3. Glial Differentiation in Midbrain Organoids

Figure 11B:
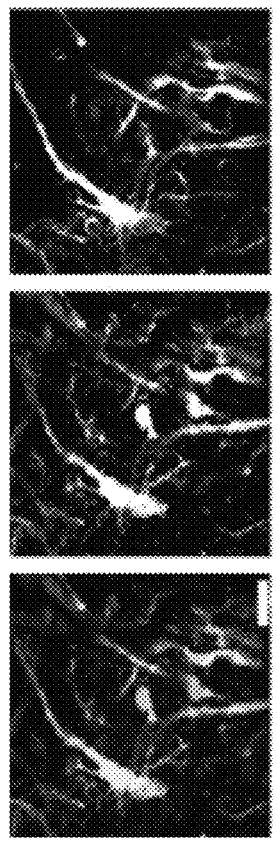
Figure 11A:
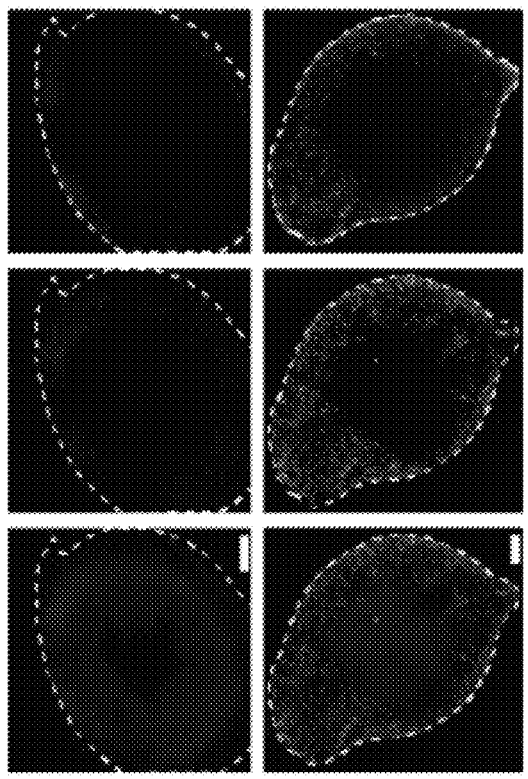

During the development of the fetal human brain, neural tube-derived cells not only differentiate into neurons but also into glia cells, including astrocytes and oligodendrocytes. Therefore, the presence of these glia cells in the midbrain organoids was investigated. In good agreement with brain development, where glia differentiation temporally follows neuronal differentiation, no significant amounts of glia cells in organoids (day 27 of the whole procedure, about 16 days after starting differentiation into midbrain organoid/early organoids) were detected. However, in more mature organoids (day 61 of the whole procedure, after about 51 days of differentiation into midbrain organoids), we observed astrocytes positive for the markers S10013 and GFAP. Interestingly, populations of astrocytes in both a quiescent state (negative for GFAP) and a reactive state characterized by GFAP expression were obtained (FIG. 11A, B).

Figure 11C:
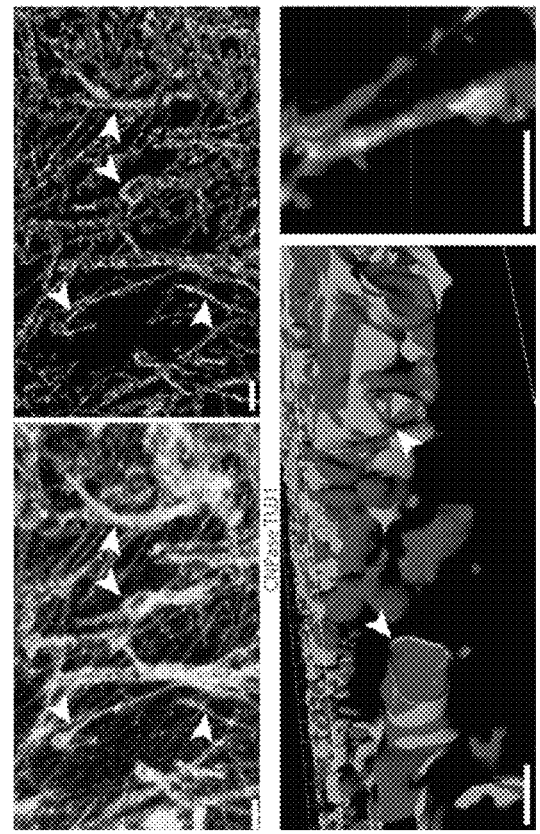

Moreover, a fraction of cells that differentiated into O4-positive oligodendrocytes at day 44 of the whole procedure (at about 34 days of differentiation into midbrain organoids) was detected. Furthermore, interestingly, these oligodendrocytes typically showed a spatially asymmetric distribution within the organoids (not shown). In the central nervous system, mature oligodendrocytes form myelin sheaths that enwrap axons to accelerate the transmission of action potentials along axons. To analyze if the oligodendrocytes within the midbrain organoids are able to execute their actual function, i.e., formation of myelin sheets, we performed immunofluorescence staining against 2',3'-cyclic-nucleotide 3'-phosphodiesterase (CNPase), a myelin-associated enzyme together with the neuronal marker TUJ1. A 3D surface reconstruction of these stainings revealed numerous TUJ1-positive neurites that were ensheathed by myelin sheets of CNPase-positive oligodendrocytes (FIG. 11C). Interestingly, these neurites often showed gaps of ensheathment, resembling the formation of nodes of Ranvier (FIG. 11C) that allow for saltatory fast neuronal transmission.

4. Functionality of Midbrain Organoids

Figure 11D:
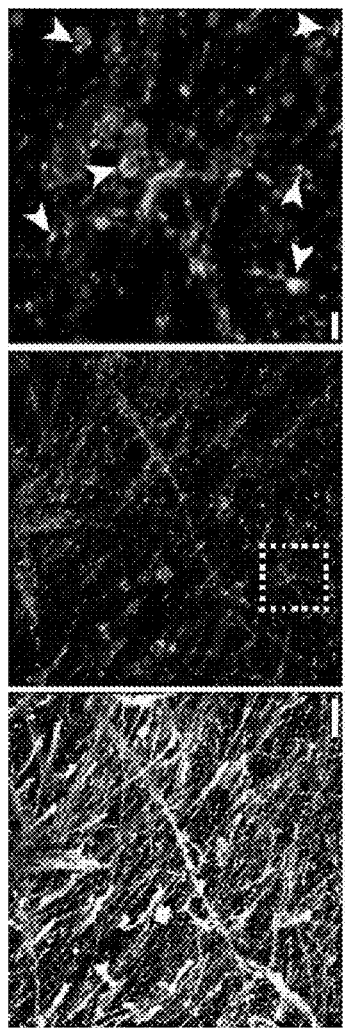
Figure 11E:
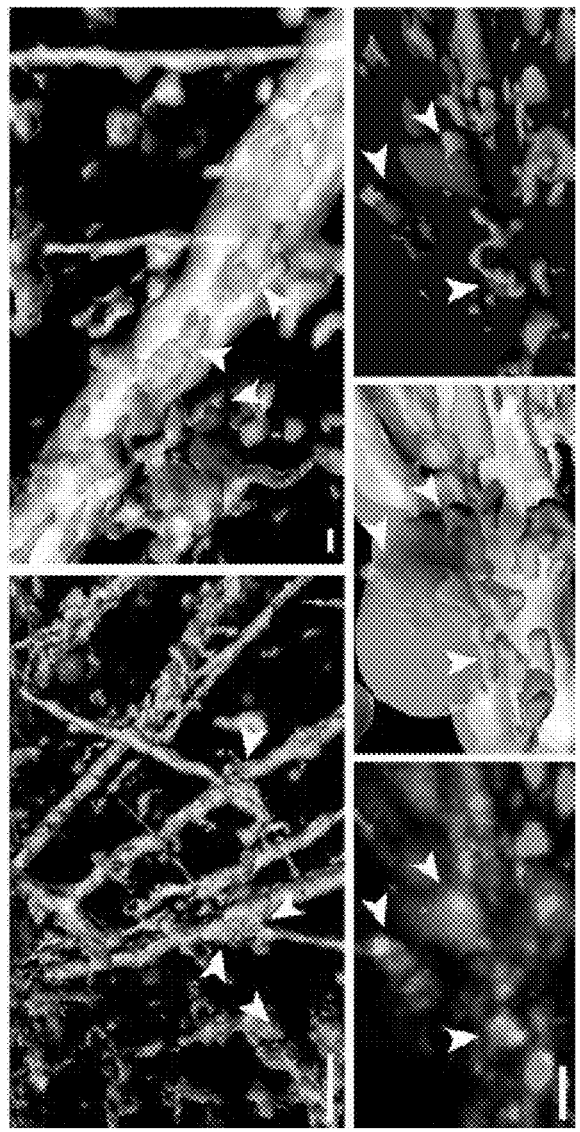

One important requirement for neuronal transmission is the development of a mature neuronal network via the formation of synaptic connections. Therefore, synaptic connectivity was investigated using immunohistological staining against the presynaptic marker synaptophysin and the postsynaptic marker PSD95 at day 61 (51 days of differentiation into midbrain organoids). A subsequent 3D surface reconstruction demonstrated not only the formation of numerous pre- and postsynaptic puncta but also multiple synaptic connections (FIG. 11D). Synaptic connections have been developed between different neurites, indicated by the direct contact of synaptophysin-positive presynapses with PSD95-positive postsynapses (FIG. 11E). Accordingly, midbrain organoids exhibit the ability to forward signals via synaptic connections and thus fulfill the prerequisite for being electrophysiologically functional.

Figure 12A:
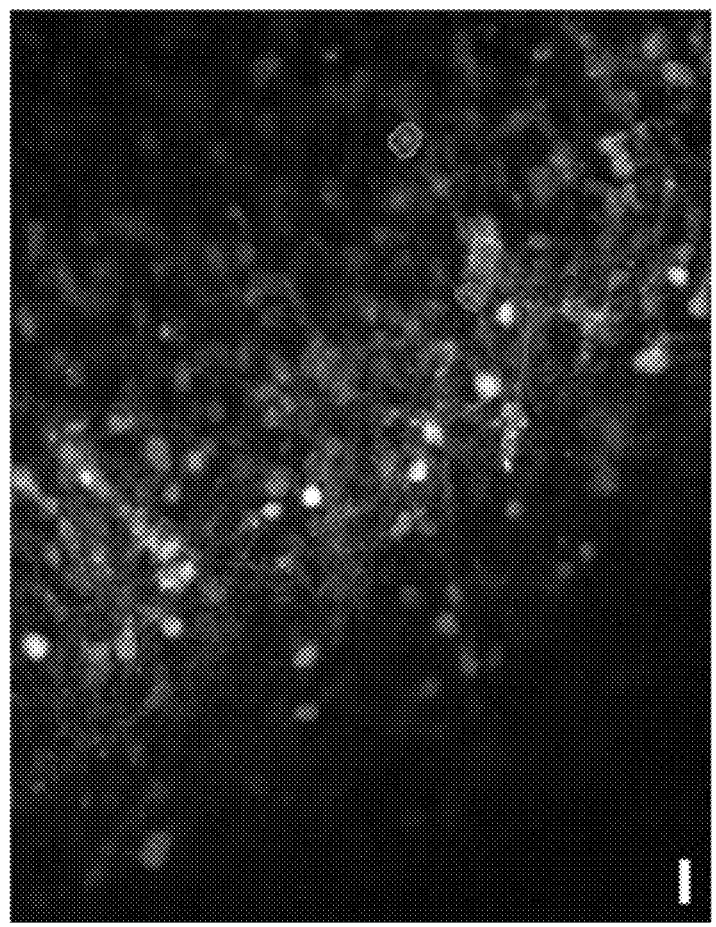
Figure 12E:
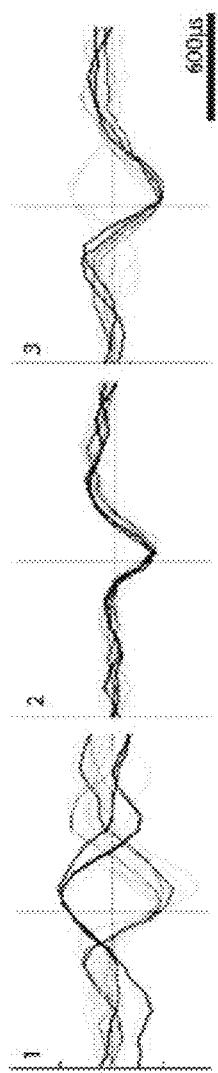
Figure 12F:
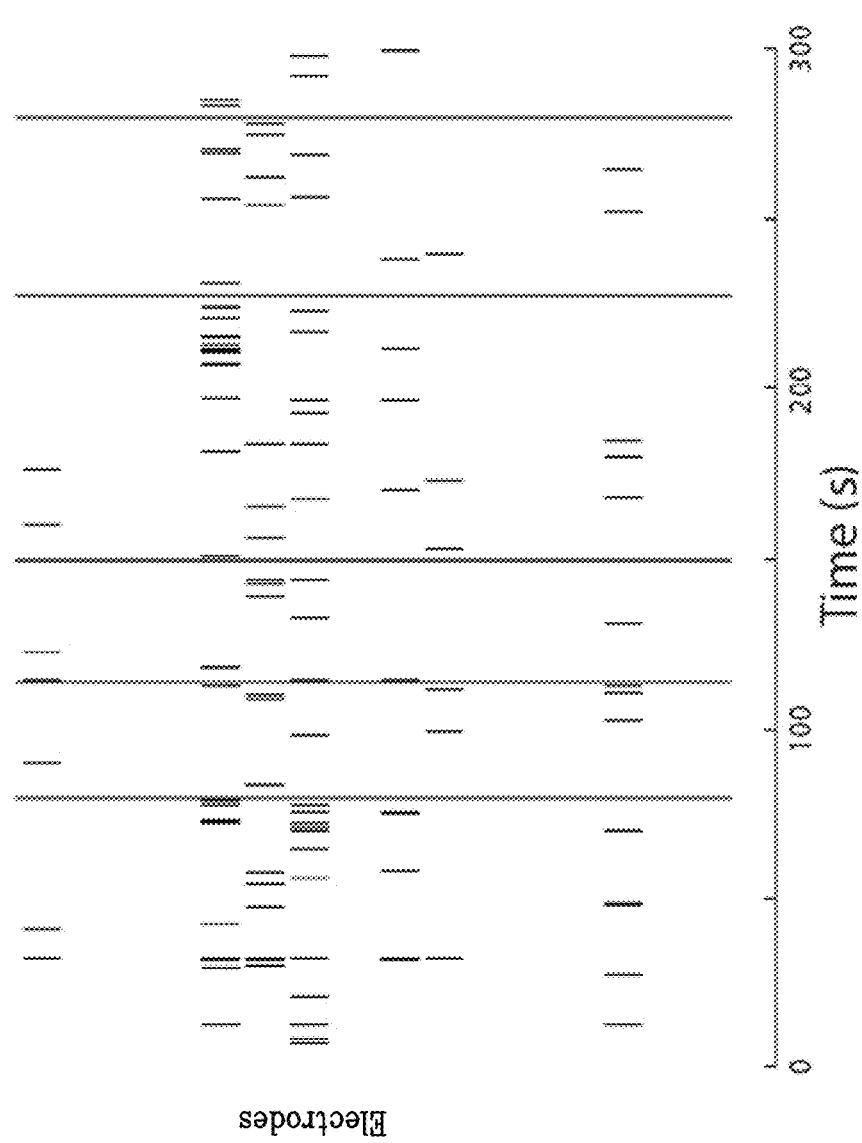

To further confirm their functionality and neuronal network activity, we performed Fluo-4AM calcium imaging on whole organoids. We measured the spontaneous neuronal activity based on calcium transients evoked by action potentials (FIG. 12A, B). Notably, some of the fluorescent traces showed regular firing patterns, which were indicative of tonic electrophysiological activity and resembled the pacemaker activity of dopaminergic neurons (Moreno et al. (2015), "Differentiation of neuroepithelial stem cells into functional dopaminergic neurons in 3D microfluidic cell culture." Lab on a chip 15, 2419-2428; Cummings et al. (2014)" Alzheimer's disease drug-development pipeline: few candidates, frequent failures." Alzheimer's research & therapy 6, 37). In addition to calcium imaging, a multielectrode array (MEA) system was used to examine the electrophysiological activity. This methodology allows non-invasive recordings of extracellular field potentials generated by action potentials. At day 60-70 (50-60 of differentiation), the midbrain organoids were placed on a grid of 16 electrodes in a 48-well tissue culture plate (FIG. 12C). Spontaneous activity was detected over several days by individual electrodes in the form of mono- and biphasic spikes (26.12±5.1 spikes/active electrode (n3), FIG. 12D,E). Furthermore, spikes occurred close in time on multiple electrodes, which represents neuronal network synchronicity (FIG. 12F). These findings indicate that midbrain organoids develop functional synaptic connections and show spontaneous neuronal activity.

REFERENCES

Abeliovich, A., and Hammond, R. (2007). Midbrain dopamine neuron differentiation: factors and fates. Developmental biology 304, 447-454.

Ang, S. L. (2009). Foxa1 and Foxa2 transcription factors regulate differentiation of midbrain dopaminergic neurons. Advances in experimental medicine and biology 651, 58-65.

Bardy, van den Hurk, Eames, March and, Hernandez, Kellogg, Gorris, Galet, Palomares, Brown, Bang, Mertens, Bohnke, Boyer, Simon, Gage (2015) "Neuronal medium that supports basic synaptic functions and activity of human neurons in vitro." Proceedings of the National Academy of Sciences of the United States of America 112, E2725-2734.

Cummings, Morstorf, Zhong, (2014) "Alzheimer's disease drug-development pipeline: few candidates, frequent failures." *Alzheimer's research & therapy* 6, 37.

Diego, Reichinnek, Both, Hamprecht (2013) "Automated identification of neuronal activity from calcium imaging by sparse dictionary learning." Proceedings of the IEEE 10th International Symposium on Biomedical Imaging, pp. 1058-1061.

Gage, F. H. (2000). Mammalian neural stem cells. Science (New York, N.Y.) 287, 1433-1438.

Gale, E., and Li, M. (2008). Midbrain dopaminergic neuron fate specification: Of mice and embryonic stem cells. Mol Brain 1, 8.

Heldin, Miyazono and ten Dijke (1997) "TGF-bold beta signaling from cell membrane to nucleus through SMAD proteins." Nature 390, 465-471.

Jiwang Zhanga, Linheng Lia (2005) BMP signaling and stem cell regulation Developmental Biology Volume 284, Issue 1, 1 Aug. 2005, Pages 1-11.

Lancaster, M. A., and Knoblich, J. A. (2014a). Generation of cerebral organoids from human pluripotent stem cells. Nature protocols 9, 2329-2340.

Lancaster, M. A., and Knoblich, J. A. (2014b). Organogenesis in a dish: modeling development and disease using organoid technologies. Science 345, 1247125.

Lancaster, M. A., Renner, M., Martin, C. A., Wenzel, D., Bicknell, L. S., Hurles, M. E., Homfray, Lancaster and Knoblich, (2014c) Generation of cerebral organoids from human pluripotent stem cells. Nature protocols 9, 2329-2340

T., Penninger, J. M., Jackson, A. P., and Knoblich, J. A. (2013). Cerebral organoids model human brain development and microcephaly. Nature 501, 373-379.

Lewis, T. L., Jr., Courchet, J., and Polleux, F. (2013). Cell biology in neuroscience: Cellular and molecular mechanisms underlying axon formation, growth, and branching. The Journal of cell biology 202, 837-848.

Logan and Nusse (2004) "The Wnt signaling pathway in development and disease." Annu. Rev. Cell Dev. Biol. 20:781-810

Moreno, Hachi, Hemmer, Trietsch, Baumuratov, Hankemeier, Vulto, Schwamborn, Fleming, (2015) "Differentiation of neuroepithelial stem cells into functional dopaminergic neurons in 3D microfluidic cell culture." Lab on a chip 15, 2419-2428.

Niwa, H. (2007). How is pluripotency determined and maintained? Development 134, 635-646.

Reinhardt, P., Glatza, M., Hemmer, K., Tsytsyura, Y., Thiel, C. S., Hoing, S., Moritz, S., Parga, J. A., Wagner, L., Bruder, J. M., et al. (2013). Derivation and expansion using only small molecules of human neural progenitors for neurodegenerative disease modeling. PloS one 8, e59252.

Reinhardt, Glatza, Hemmer, Tsytsyura, Thiel, Hoing, Moritz, Parga, Wagner, Bruder, Wu, Schmid, Ropke, Klingauf, Schwamborn, Gasser, Scholer, Sterneckert, Derivation and expansion using only small molecules of human neural progenitors for neurodegenerative disease modeling. PloS one 8, e59252.

Sharples, S. A., Koblinger, K., Humphreys, J. M., and Whelan, P. J. (2014). Dopamine: a parallel pathway for the modulation of spinal locomotor networks. Frontiers in neural circuits 8, 55.

Takahashi, K., Tanabe, K., Ohnuki, M., Narita, M., Ichisaka, T., Tomoda, K., and Yamanaka, S. (2007). Induction of pluripotent stem cells from adult human fibroblasts by defined factors. Cell 131, 861-872.

Takahashi, K., and Yamanaka, S. (2006). Induction of pluripotent stem cells from mouse embryonic and adult fibroblast cultures by defined factors. Cell 126, 663-676.

Thomson, J. A., and Odorico, J. S. (2000). Human embryonic stem cell and embryonic germ cell lines. Trends in biotechnology 18, 53-57.

Weissman, I. L. (2000). Stem cells: units of development, units of regeneration, and units in evolution. Cell 100, 157-168.

Yamanaka, S., and Blau, H. M. (2010). Nuclear reprogramming to a pluripotent state by three approaches. Nature 465, 704-712.

Yu, J., Vodyanik, M. A., Smuga-Otto, K., Antosiewicz-Bourget, J., Frane, J. L., Tian, S., Nie, J., Jonsdottir, G. A., Ruotti, V., Stewart, R., et al. (2007). Induced pluripotent stem cell lines derived from human somatic cells. Science 318, 1917-1920.

---

The invention claimed is:

1. A method of generating a midbrain organoid, comprising the steps of
   (i) culturing neuroepithelial stem cells for a first period of time with differentiation medium (I) comprising
      (a) at least two different neurotrophins, and
      (b) an antioxidant, and
      (c) a SHH-pathway activator,
   (ii) culturing neuroepithelial stem cells obtained from step (i) for a second period of time with differentiation medium (II) comprising
      (a) said at least two different neurotrophins, and
      (b) said antioxidant, and
   (iii) culturing neuroepithelial stem cells obtained from step (ii) for a third period of time
      with differentiation medium (II) which is further supplemented with FGF8, wherein in steps (i), (ii) and (iii) the neuroepithelial stem cells are cultured in a three-dimensional cell culture comprising a matrix, wherein at least a part of the-culturing in steps (i)-(iii) is performed under agitating conditions, thereby obtaining a midbrain organoid, wherein said midbrain organoid comprises one or more of astrocytes, oligodendrocytes, and oligodendrocyte progenitors, wherein said midbrain organoid comprises an asymmetric polar organization of dopaminergic neurons, and wherein said asymmetric polar organization of dopaminergic neurons within the midbrain organoid is characterized by the localization of
      (a) dopaminergic neurons expressing TUJ1 and TH in the outermost part of the midbrain organoid, and/or
      (b) dopaminergic neurons expressing MAP2 and TH in the inner part of the midbrain organoid.

2. The method of claim 1, wherein said neuroepithelial stem cells are human neuroepithelial stem cells.

3. The method of claim 1, wherein said neuroepithelial stem cells are genetically modified or obtained from a patient suffering from a neurological disease.

4. The method of claim 1, wherein said neuroepithelial stem cells have been produced from induced pluripotent stem cells (iPSCs).

5. The method of claim 1, wherein the matrix comprises one or more of polymers, metals, ceramics and/or carbon nanotubes.

6. The method of claim 1, wherein FGF8 is added to the differentiation medium (II) after 8 days of culturing in the differentiation medium (II).

7. The method of claim 1, wherein the neuroepithelial stem cells are cultured in a maintenance medium before they are cultured in step (i) with differentiation medium (I), wherein the maintenance medium comprises (i) a SHE-pathway activator; (ii) a canonical WNT-signaling activator; and (iii) an antioxidant.

8. The method of claim 1, wherein the neuroepithelial stem cells are present in a colony.

9. The method of claim 1, wherein said agitating conditions comprise shaking, spinning, stirring, moving and/or mixing of the three-dimensional cell culture.

10. The method of claim 1, wherein agitating is started after starting culturing of the neuroepithelial stem cells in step (i) and continued in steps (ii) and (iii).

11. The method of claim 1, wherein the midbrain organoid is obtained after 1 or more weeks of differentiation.

12. The method of claim 1, wherein said midbrain organoid is an early midbrain organoid or a late midbrain organoid.

13. The method of claim 1, wherein said midbrain organoid further comprises one or more of:
   (a) neural progenitor cells;
   (b) young neurons;
   (c) young dopaminergic neurons;
   (d) mature neurons;
   (e) mature dopaminergic neurons;
   and (f) processes that expand from the midbrain organoid through the matrix.

14. The method of claim 1, wherein the at least two different neurotrophins in the differentiation media are selected from the group consisting of NGF, BDNF, NT-3, NT-4, CNTF and GDNF.

* * * * *

SEQUENCE LISTING

```
<160> NUMBER OF SEQ ID NOS: 20

<210> SEQ ID NO 1
<211> LENGTH: 5844
<212> TYPE: DNA
<213> ORGANISM: Homo sapiens

<400> SEQUENCE: 1 agtctgggc gggcgctcgg gctgcgcggg ctctgggcag cagcagcagc agcagcagca      60
tcctctcttc ctttacttcc cttccgcttc tttctcttcc ttctccttct tttttccccc     120
cctccccttc ttccctaac ccttctaccc ctctccttt tctccggagg gcgctaagtc     180
cgtgagcggt ggcagtcgcg accgcgggtg catccagttt ctgcgcccag attttattga     240
tctaatccaa agtatcttat aacttctggc tggaattaag attcttcagc ttgtctctaa     300
ccgaggaagc attgattggg agctactcat tcagaaaatt aaaagaaaga agccagaaaa     360
tattatcaac cctttgagaa cacgacacaa cgaactttat attttaccac ttccttgaat     420
agttgcagga gaaataacaa ggcattgaag aatggcagat gaacggaaag atgaagcaaa     480
ggcacctcac tggacctcag caccgctaac agaggcatct gcacactcac atccacctga     540
gattaaggat caaggcggag caggggaagg acttgtccga agcgccaatg gattcccata     600
cagggaggat gaagagggtg cctttggaga gcatgggtca cagggcacct attcaaatac     660
caaagagaat gggatcaacg gagagctgac ctcagctgac agagaaacag cagaggaggt     720
gtctgcaagg atagttcaag tagtcactgc tgaggctgta gcagtcctga aaggtgaaca     780
agagaaagaa gctcaacata aagaccagac tgcagctctg cctttagcag ctgaagaaac     840
agctaatctg cctccttctc cacccccatc acctgcctca gaacagactg tcacagtgga     900
ggaagcagca ggtggggaat cagctctggc tcccagtgta tttaaacagg caaaggacaa     960
```

```
agtctctaat tctaccttgt caaagattcc tgctttacag ggtagcacaa agtccccaag    1020
atacagctca gcctgcccta gcacgactaa aagggctaca ttttctgaca gtttattaat    1080
acagcccacc tcagcaggct ccacagaccg tttgccatac tcaaaatcag ggaacaagga    1140
cggagtaacc aagagcccag aaaagcgctc ttctctccca agaccttcct ccattctccc    1200
tcctcggcga ggtgtgtcag gagacagaga tgagaattcc ttctctctca acagttctat    1260
ctcttcttca gcacggcgga ccaccaggtc agagccaatt cgcagagcag gaagagtgg    1320 tacctcaaca cccactaccc ctgggtctac tgccatcact cctggcaccc caccaagtta    1380
ttcttcacgc acaccaggca ctcctggaac ccctagctat cccaggaccc ctcacacacc    1440
aggaaccccc aagtctgcca tcttggtgcc gagtgagaag aaggtcgcca tcatacgtac    1500
tcctccaaaa tctcctgcga ctcccaagca gcttcggctt attaaccaac cactgccaga    1560
cctgaagaat gtcaaatcca aaatcggatc aacagacaac atcaaatacc agcctaaagg    1620
ggggcaggtt aggattttaa acaagaagat cgattttagc aaagttcagt ccagatgtgg    1680
ttccaaggat aacatcaaac attcggctgg gggcggaaat gtacaaattg ttaccaagaa    1740
aatagaccta agccatgtga catccaaatg tggctctctg aagaacatcc gccacaggcc    1800
aggtggcgga cgtgtgaaaa ttgagagtgt aaaactagat ttcaaagaaa aggcccaagc    1860
taaagttggt tctcttgata tgctcatca tgtacctgga ggtggtaatg tcaagattga    1920
cagccaaaag ttgaacttca gagagcatgc taaagcccgt gtggaccatg ggctgagat    1980 cattacacag tccccaggca gatccagcgt ggcatcaccc cgacgactca gcaatgtctc    2040
ctcgtctgga agcatcaacc tgctcgaatc tcctcagctt gccactttgg ctgaggatgt    2100
cactgctgca ctcgctaagc agggcttgtg aatatttctc atttagcatt gaaataataa    2160
tatttaggca tgagctcttg gcaggagtgg gctctgagca gttgttatat tcattcttta    2220
taaaccataa aataaataat ctcatcccca aactgtagta attgttacaa ttttctattt    2280
aaaaaatgaa tagtacatgc agaaattgac ctgatttcca tttgcaacag gaagacactg    2340
gctttacatg ggttcaattg gacaattatt tttgctctgc tctgttttgc atggagtatt    2400
attattttaa aaattgcatt tttaccttc atgtgcctga aggctatcca ctacattctg    2460
aaggccttgt taaaatccaa gctgctcatt tcactattct gtttctgagt gagaagataa    2520
aaactgccca ttgtaactta tttcaggtta aattaaacca aggagtctga ttgcaggaag    2580
ggaagagcat gtaagaaata agttttttta aagtgttatt ttgtataaat gggaagaaag    2640
attcaattaa gttattaaca tttgggacct ggataattat atcagagtat gtcagtccaa    2700
taaattattt aactaattaa aaaatagttg caaagcattt gagctgtggt tgaggaagtg    2760
gtgtaaaagt gcatccatta ggaatgatgc actttcatta ggatggactc gtgtctgatt    2820
agaatgtcag ttgatcagct agatttgtgt ccacactacc agtttcacac ccctttcca    2880 tctgtttgat acagtattat agatataaat atatatatat ttctctgtgg ccatttgtga    2940
tacttcctca tatacttgaa tattatactt ctttattcac agtatctgtg tctcctgcac    3000
cctttggtgt tgcaatttta gatatgtgaa agtagatgtt agcagggttc tctccctatt    3060
taaaaaaaat acattaaaaa agacaaaaaa ttttagcatg aagttgcttt ctgtaacaac    3120
tcaaagccgt aaccctgttt tagtgccaga tacaagtctc tcccgtgatg ctagacaaaa    3180
aattattttt ctttgctttc accaacatgg agtttgtggg ggtgggtcca gttatacatg    3240
aaagggttta cagattgttg gtttaagatt atggatttat ctcatttta atcacaggat    3300
```

```
agtttggggt ttattcctat tattattcat gaaaccgact taagattttt tctttatttt    3360
tcttttttt  tccatttgct aaagttgaaa gttgaaacta actataatag tttgaaacat    3420
gttttctcat ttttccaaat agtatctgtt tattaaattc tctaatagaa gatgtttgtc    3480
tttcttaccc aaagtaaaga tccctgatc agaaagaaaa aatacaatac tttgggaagc     3540
tatagctata aaacacttga gacacagata tctaaatcag ttttttttcca agactccaac   3600
attgcactct gtaaagtaac acactgtgat ctagtattat ttatcagtag ataatactgt   3660
tctgactgta tatacagtct agaactcaca aatcaattag ttcctctcac aaatcattca    3720
tcttagactt acaaataagg aatgaaatag tcaatggcct gattaaggca aagagctacc   3780
aggctagatg gacactttt  aaaaatttta tctgttcttt tcttgctca gggctggtag     3840
gttggatctg aaccattaaa atcaaatggt ccactaggcg tatgatctct ttgagccaaa    3900
tcagttcctg aatataaagg aggaaatgat gaggatgtac tgaggcaacg gggaagtata    3960
gaaacatcca agacaaaagc caagggatgc aaaggcagag acacaggtgc ttttggtga    4020
cccagtggat atggcaacca gtgtaactgc catacaagaa accctaggag caaacccaca    4080
ccactcattc tcagctaaga gattttacac aggcaaacgt gtcttaaacc atctataaat    4140
cagttatttt atatgacagt caaaaccttaa gaaaccttag gatcattata tctattttct   4200
gcctattaat tgctgtgagg tttgatttga ccaatctggg caattattc atcagcttcc    4260
cttgaagtgc accagaaaat agaagaaagg tgtgtggaga cttagggtat tttattacat   4320
gttttcatag tcttaaatag tgattaaatt tctctagaaa gaagttaaca gctcattaga    4380
aaagttttaa cctgtgaaat aagtattttt ctcaacattc tttaaagttt ttatataagt    4440
taacactagg taaacattct gcatactaga agtcagttta ttacaaatac atgtcaaaaa    4500
taaagattat acaaggcacc aaactactag atttggcatt aaaacaaatg tttatttcta    4560
atcacaacaa aattataatg aataaatgtt cttgctttgt atggaaatac aattctttat    4620
taaagttaac agaaaggaac tgatcgtttg taccagtaaa agagagaaac acacaggtta    4680
aatatcttct tgtggggtta aggggtagaa cctatcttgc cttcactctc aagataacga    4740
ctcaaattaa gcttttttgag caccactctt gtggggacac acatacgctg atctaggaat    4800
gaaatcttcg tggtctcaat tctagatcta ctatgccagt ttctctctgg ctttagcctt    4860
tgagaacctg tataagaata cgtaagtaat ccagagctgt gaagagttta aaggccaact   4920
tctccagtga actcaacctc tgggtcactt gcaaccagaa attggatacc tcataatgat   4980
gcaggaaaga cccgagttca tgatgagttt caaaggccac gttcatttag gaaccaactc   5040
tctctggatt tacctgctga gttccagcag cgtgatgggc tgacatccca cctacaagta    5100
tgacacctgt gtaacaccag ctaggtacgg ctggagaagg ctgaagagag aatgccatta    5160
aatggaagaa tgtactgatt gtagtgacct tctccacaca cacacacaca cacacacaca   5220
cacacaccta cagtaataca gcaagcgtgg aataatcagc caatatataa cattccatca   5280
gtattttatt aaggaaataa cctgaatgtg gttgattttg acatagctgc aattacagtt    5340
ttcttctatt tttcaagcca caataaggaa aataaactac tcatggtcta aatactagag    5400
ataaagtaga ttcatggctt ggtaaggaaa ttttaagcat tccttcaaag attgacgtgc    5460
taaaataagc attgatgttt tgagtttttt tacacctagg atttttagct tgggtgtgta    5520
ggtgaaggcc aagactctct gcaggaaaaa gcttattttc aaactcagaa ataaaatgt     5580
caatcataaa aatctacttc aactttagca aaaagaaaaa aaatcaaca aaaagtatac    5640
tctgtatgct gggattccga ggttccaaca cactgttaca aatctgtggg gggtttcttt    5700
```

```
cttctgataa ttctagagcc tgttaccata gaaaggcatt tcttcaatgg ctggttgtag      5760
ttagttcatg tttttcaatc aaatttgcaa atgtatttgt tgctgtatag tgattgtttt      5820
gcaaaataaa attgcttgtc acct                                             5844
```

<210> SEQ ID NO 2
<211> LENGTH: 1827
<212> TYPE: PRT
<213> ORGANISM: Homo sapiens

<400> SEQUENCE: 2

```
Met Ala Asp Glu Arg Lys Asp Glu Ala Lys Ala Pro His Trp Thr Ser
1               5                   10                  15

Ala Pro Leu Thr Glu Ala Ser Ala His Ser His Pro Glu Ile Lys
            20                  25                  30

Asp Gln Gly Gly Ala Gly Gly Leu Val Arg Ser Ala Asn Gly Phe
        35                  40                  45

Pro Tyr Arg Glu Asp Glu Glu Gly Ala Phe Gly Glu His Gly Ser Gln
    50                  55                  60

Gly Thr Tyr Ser Asn Thr Lys Glu Asn Gly Ile Asn Gly Glu Leu Thr
65                  70                  75                  80

Ser Ala Asp Arg Glu Thr Ala Glu Glu Val Ser Ala Arg Ile Val Gln
                85                  90                  95

Val Val Thr Ala Glu Ala Val Ala Val Leu Lys Gly Glu Gln Glu Lys
            100                 105                 110

Glu Ala Gln His Lys Asp Gln Thr Ala Ala Leu Pro Leu Ala Ala Glu
        115                 120                 125

Glu Thr Ala Asn Leu Pro Pro Ser Pro Pro Pro Ser Pro Ala Ser Glu
    130                 135                 140

Gln Thr Val Thr Val Glu Glu Asp Leu Leu Thr Ala Ser Lys Met Glu
145                 150                 155                 160

Phe His Asp Gln Gln Glu Leu Thr Pro Ser Thr Ala Glu Pro Ser Asp
                165                 170                 175

Gln Lys Glu Lys Glu Ser Glu Lys Gln Ser Lys Pro Gly Glu Asp Leu
            180                 185                 190

Lys His Ala Ala Leu Val Ser Gln Pro Glu Thr Thr Lys Thr Tyr Pro
        195                 200                 205

Asp Lys Lys Asp Met Gln Gly Thr Glu Glu Lys Ala Pro Leu Ala
    210                 215                 220

Leu Phe Gly His Thr Leu Val Ala Ser Leu Glu Asp Met Lys Gln Lys
225                 230                 235                 240

Thr Glu Pro Ser Leu Val Val Pro Gly Ile Asp Leu Pro Lys Glu Pro
                245                 250                 255

Pro Thr Pro Lys Glu Gln Lys Asp Trp Phe Ile Glu Met Pro Thr Glu
            260                 265                 270

Ala Lys Lys Asp Glu Trp Gly Leu Val Ala Pro Ile Ser Pro Gly Pro
        275                 280                 285

Leu Thr Pro Met Arg Glu Lys Asp Val Phe Asp Ile Pro Lys Trp
    290                 295                 300

Glu Gly Lys Gln Phe Asp Ser Pro Met Pro Ser Pro Gln Gly Gly
305                 310                 315                 320

Ser Phe Thr Leu Pro Leu Asp Val Met Lys Asn Glu Ile Val Thr Glu
                325                 330                 335

Thr Ser Pro Phe Ala Pro Ala Phe Leu Gln Pro Asp Asp Lys Lys Ser
```

```
            340             345             350
Leu Gln Gln Thr Ser Gly Pro Ala Thr Ala Lys Asp Ser Phe Lys Ile
        355                 360             365

Glu Glu Pro His Glu Ala Lys Pro Asp Lys Met Ala Glu Ala Pro Pro
    370                 375             380

Ser Glu Ala Met Thr Leu Pro Lys Asp Ala His Ile Pro Val Val Glu
385                 390             395                 400

Glu His Val Met Gly Lys Val Leu Glu Glu Lys Glu Ala Ile Asn
                405             410             415

Gln Glu Thr Val Gln Gln Arg Asp Thr Phe Thr Pro Ser Gly Gln Glu
                420             425             430

Pro Ile Leu Thr Glu Lys Glu Thr Glu Leu Lys Leu Glu Glu Lys Thr
            435             440             445

Thr Ile Ser Asp Lys Glu Ala Val Pro Lys Glu Ser Lys Pro Pro Lys
            450             455             460

Pro Ala Asp Glu Glu Ile Gly Ile Ile Gln Thr Ser Thr Glu His Thr
465                 470             475                 480

Phe Ser Glu Gln Lys Asp Gln Glu Pro Thr Thr Asp Met Leu Lys Gln
                485             490             495

Asp Ser Phe Pro Val Ser Leu Glu Gln Ala Val Thr Asp Ser Ala Met
                500             505             510

Thr Ser Lys Thr Leu Glu Lys Ala Met Thr Glu Pro Ser Ala Leu Ile
            515             520             525

Glu Lys Ser Ser Ile Gln Glu Leu Phe Glu Met Arg Val Asp Asp Lys
        530             535             540

Asp Lys Ile Glu Gly Val Gly Ala Ala Thr Ser Ala Glu Leu Asp Met
545                 550             555                 560

Pro Phe Tyr Glu Asp Lys Ser Gly Met Ser Lys Tyr Phe Glu Thr Ser
                565             570             575

Ala Leu Lys Glu Glu Ala Thr Lys Ser Ile Glu Pro Gly Ser Asp Tyr
            580             585             590

Tyr Glu Leu Ser Asp Thr Arg Glu Ser Val His Glu Ser Ile Asp Thr
        595             600             605

Met Ser Pro Met His Lys Asn Gly Asp Lys Glu Phe Gln Thr Gly Lys
    610             615             620

Glu Ser Gln Pro Ser Pro Pro Ala Gln Glu Ala Gly Tyr Ser Thr Leu
625                 630             635             640

Ala Gln Ser Tyr Pro Ser Asp Leu Pro Glu Glu Pro Ser Ser Pro Gln
            645             650             655

Glu Arg Met Phe Thr Ile Asp Pro Lys Val Tyr Gly Glu Lys Arg Asp
            660             665             670

Leu His Ser Lys Asn Lys Asp Asp Leu Thr Leu Ser Arg Ser Leu Gly
        675             680             685

Leu Gly Gly Arg Ser Ala Ile Glu Gln Arg Ser Met Ser Ile Asn Leu
    690             695             700

Pro Met Ser Cys Leu Asp Ser Ile Ala Leu Gly Phe Asn Phe Gly Arg
705             710             715             720

Gly His Asp Leu Ser Pro Leu Ala Ser Asp Ile Leu Thr Asn Thr Ser
                725             730             735

Gly Ser Met Asp Glu Gly Asp Asp Tyr Leu Pro Ala Thr Thr Pro Ala
            740             745             750

Leu Glu Lys Ala Pro Cys Phe Pro Val Glu Ser Lys Glu Glu Gln
            755             760             765
```

```
Ile Glu Lys Val Lys Ala Thr Gly Glu Glu Ser Thr Gln Ala Glu Ile
    770                 775                 780

Ser Cys Glu Ser Pro Phe Leu Ala Lys Asp Phe Tyr Lys Asn Gly Thr
785                 790                 795                 800

Val Met Ala Pro Asp Leu Pro Glu Met Leu Asp Leu Ala Gly Thr Arg
                805                 810                 815

Ser Arg Leu Ala Ser Val Ser Ala Asp Ala Glu Val Ala Arg Arg Lys
                820                 825                 830

Ser Val Pro Ser Glu Thr Val Glu Asp Ser Arg Thr Gly Leu Pro
                835                 840                 845

Pro Val Thr Asp Glu Asn His Val Ile Val Lys Thr Asp Ser Gln Leu
    850                 855                 860

Glu Asp Leu Gly Tyr Cys Val Phe Asn Lys Tyr Thr Val Pro Leu Pro
865                 870                 875                 880

Ser Pro Val Gln Asp Ser Glu Asn Leu Ser Gly Glu Ser Gly Thr Phe
                885                 890                 895

Tyr Glu Gly Thr Asp Asp Lys Val Arg Arg Asp Leu Ala Thr Asp Leu
                900                 905                 910

Ser Leu Ile Glu Val Lys Leu Ala Ala Ala Gly Arg Val Lys Asp Glu
    915                 920                 925

Phe Ser Val Asp Lys Glu Ala Ser Ala His Ile Ser Gly Asp Lys Ser
    930                 935                 940

Gly Leu Ser Lys Glu Phe Asp Gln Glu Lys Lys Ala Asn Asp Arg Leu
945                 950                 955                 960

Asp Thr Val Leu Glu Lys Ser Glu His Ala Asp Ser Lys Glu His
                965                 970                 975

Ala Lys Lys Thr Glu Glu Ala Gly Asp Glu Ile Glu Thr Phe Gly Leu
                980                 985                 990

Gly Val Thr Tyr Glu Gln Ala Leu Ala Lys Asp Leu Ser Ile Pro Thr
    995                 1000                1005

Asp Ala Ser Ser Glu Lys Ala Glu Lys Gly Leu Ser Ser Val Pro
    1010                1015                1020

Glu Ile Ala Glu Val Glu Pro Ser Lys Lys Val Glu Gln Gly Leu
    1025                1030                1035

Asp Phe Ala Val Gln Gly Gln Leu Asp Val Lys Ile Ser Asp Phe
    1040                1045                1050

Gly Gln Met Ala Ser Gly Leu Asn Ile Asp Asp Arg Arg Ala Thr
    1055                1060                1065

Glu Leu Lys Leu Glu Ala Thr Gln Asp Met Thr Pro Ser Ser Lys
    1070                1075                1080

Ala Pro Gln Glu Ala Asp Ala Phe Met Gly Val Glu Ser Gly His
    1085                1090                1095

Met Lys Glu Gly Thr Lys Val Ser Glu Thr Glu Val Lys Glu Lys
    1100                1105                1110

Val Ala Lys Pro Asp Leu Val His Gln Glu Ala Val Asp Lys Glu
    1115                1120                1125

Glu Ser Tyr Glu Ser Ser Gly Glu His Glu Ser Leu Thr Met Glu
    1130                1135                1140

Ser Leu Lys Ala Asp Glu Gly Lys Lys Glu Thr Ser Pro Glu Ser
    1145                1150                1155

Ser Leu Ile Gln Asp Glu Ile Ala Val Lys Leu Ser Val Glu Ile
    1160                1165                1170
```

```
Pro Cys Pro Pro Ala Val Ser Glu Ala Asp Leu Ala Thr Asp Glu
1175                 1180                 1185

Arg Ala Asp Val Gln Met Glu Phe Ile Gln Gly Pro Lys Glu Glu
1190                 1195                 1200

Ser Lys Glu Thr Pro Asp Ile Ser Ile Thr Pro Ser Asp Val Ala
1205                 1210                 1215

Glu Pro Leu His Glu Thr Ile Val Ser Glu Pro Ala Glu Ile Gln
1220                 1225                 1230

Ser Glu Glu Glu Glu Ile Glu Ala Gln Gly Glu Tyr Asp Lys Leu
1235                 1240                 1245

Leu Phe Arg Ser Asp Thr Leu Gln Ile Thr Asp Leu Gly Val Ser
1250                 1255                 1260

Gly Ala Arg Glu Glu Phe Val Glu Thr Cys Pro Ser Glu His Lys
1265                 1270                 1275

Gly Val Ile Glu Ser Val Val Thr Ile Glu Asp Phe Ile Thr
1280                 1285                 1290

Val Val Gln Thr Thr Thr Asp Glu Gly Glu Ser Gly Ser His Ser
1295                 1300                 1305

Val Arg Phe Ala Ala Leu Glu Gln Pro Glu Val Glu Arg Arg Pro
1310                 1315                 1320

Ser Pro His Asp Glu Glu Glu Phe Glu Val Glu Glu Ala Ala Glu
1325                 1330                 1335

Ala Gln Ala Glu Pro Lys Asp Gly Ser Pro Glu Ala Pro Ala Ser
1340                 1345                 1350

Pro Glu Arg Glu Glu Val Ala Leu Ser Glu Tyr Lys Thr Glu Thr
1355                 1360                 1365

Tyr Asp Asp Tyr Lys Asp Glu Thr Thr Ile Asp Ser Ile Met
1370                 1375                 1380

Asp Ala Asp Ser Leu Trp Val Asp Thr Gln Asp Asp Arg Ser
1385                 1390                 1395

Ile Met Thr Glu Gln Leu Glu Thr Ile Pro Lys Glu Glu Lys Ala
1400                 1405                 1410

Glu Lys Glu Ala Arg Arg Ser Ser Leu Glu Lys His Arg Lys Glu
1415                 1420                 1425

Lys Pro Phe Lys Thr Gly Arg Gly Arg Ile Ser Thr Pro Glu Arg
1430                 1435                 1440

Lys Val Ala Lys Lys Glu Pro Ser Thr Val Ser Arg Asp Glu Val
1445                 1450                 1455

Arg Arg Lys Lys Ala Val Tyr Lys Lys Ala Glu Leu Ala Lys Lys
1460                 1465                 1470

Thr Glu Val Gln Ala His Ser Pro Ser Arg Lys Phe Ile Leu Lys
1475                 1480                 1485

Pro Ala Ile Lys Tyr Thr Arg Pro Thr His Leu Ser Cys Val Lys
1490                 1495                 1500

Arg Lys Thr Thr Ala Ala Gly Gly Glu Ser Ala Leu Ala Pro Ser
1505                 1510                 1515

Val Phe Lys Gln Ala Lys Asp Lys Val Ser Asp Gly Val Thr Lys
1520                 1525                 1530

Ser Pro Glu Lys Arg Ser Ser Leu Pro Arg Pro Ser Ser Ile Leu
1535                 1540                 1545

Pro Pro Arg Arg Gly Val Ser Gly Asp Arg Asp Glu Asn Ser Phe
1550                 1555                 1560

Ser Leu Asn Ser Ser Ile Ser Ser Ser Ala Arg Arg Thr Thr Arg
```

| | | | | | | | | | | |
|---|---|---|---|---|---|---|---|---|---|---|
| | | 1565 | | | 1570 | | | 1575 | | |
| Ser | Glu | Pro | Ile | Arg | Arg | Ala | Gly | Lys | Ser | Gly | Thr | Ser | Thr | Pro |
| | 1580 | | | | 1585 | | | | 1590 | |

Ser Glu Pro Ile Arg Arg Ala Gly Lys Ser Gly Thr Ser Thr Pro
    1580                1585                1590

Thr Thr Pro Gly Ser Thr Ala Ile Thr Pro Gly Thr Pro Pro Ser
    1595                1600                1605

Tyr Ser Ser Arg Thr Pro Gly Thr Pro Gly Thr Pro Ser Tyr Pro
    1610                1615                1620

Arg Thr Pro His Thr Pro Gly Thr Pro Lys Ser Ala Ile Leu Val
    1625                1630                1635

Pro Ser Glu Lys Lys Val Ala Ile Ile Arg Thr Pro Pro Lys Ser
    1640                1645                1650

Pro Ala Thr Pro Lys Gln Leu Arg Leu Ile Asn Gln Pro Leu Pro
    1655                1660                1665

Asp Leu Lys Asn Val Lys Ser Lys Ile Gly Ser Thr Asp Asn Ile
    1670                1675                1680

Lys Tyr Gln Pro Lys Gly Gly Gln Val Gln Ile Val Thr Lys Lys
    1685                1690                1695

Ile Asp Leu Ser His Val Thr Ser Lys Cys Gly Ser Leu Lys Asn
    1700                1705                1710

Ile Arg His Arg Pro Gly Gly Gly Arg Val Lys Ile Glu Ser Val
    1715                1720                1725

Lys Leu Asp Phe Lys Glu Lys Ala Gln Ala Lys Val Gly Ser Leu
    1730                1735                1740

Asp Asn Ala His His Val Pro Gly Gly Gly Asn Val Lys Ile Asp
    1745                1750                1755

Ser Gln Lys Leu Asn Phe Arg Glu His Ala Lys Ala Arg Val Asp
    1760                1765                1770

His Gly Ala Glu Ile Ile Thr Gln Ser Pro Gly Arg Ser Ser Val
    1775                1780                1785

Ala Ser Pro Arg Arg Leu Ser Asn Val Ser Ser Ser Gly Ser Ile
    1790                1795                1800

Asn Leu Leu Glu Ser Pro Gln Leu Ala Thr Leu Ala Glu Asp Val
    1805                1810                1815

Thr Ala Ala Leu Ala Lys Gln Gly Leu
    1820                1825

<210> SEQ ID NO 3
<211> LENGTH: 1817
<212> TYPE: DNA
<213> ORGANISM: Homo sapiens

<400> SEQUENCE: 3
cggacctcca cactgagcca tgcccacccc cgacgccacc acgccacagg ccaagggctt    60
ccgcagggcc gtgtctgagc tggacgccaa gcaggcagag gccatcatgt ccccgcggtt   120
cattgggcgc aggcagagcc tcatcgagga cgcccgcaag gagcgggagg cggcggtggc   180
agcagcggcc gctgcagtcc cctcggagcc cggggacccc ctggaggctg tggcctttga   240
ggagaaggag gggaaggccg tgctaaacct gctcttctcc ccgagggcca ccaagccctc   300
ggcgctgtcc cgagctgtga aggtgtttga cgctttgaa gccaaaatcc accatctaga   360
gacccggccc gcccagaggc gcgagctggg gcccccac ctggagtact tcgtgcgcct   420
cgaggtgcgc cgaggggacc tggccgccct gctcagtggt gtgcgccagg tgtcagagga   480
cgtgcgcagc cccgcggggc ccaaggtccc ctggttccca agaaaagtgt cagagctgga   540

```
caagtgtcat cacctggtca ccaagttcga ccctgacctg gacttggacc acccgggctt    600
ctcggaccag gtgtaccgcc agcgcaggaa gctgattgct gagatcgcct tccagtacag    660
gcacggcgac ccgattcccc gtgtggagta caccgccgag gagattgcca cctggaagga    720
ggtctacacc acgctgaagg gcctctacgc cacgcacgcc tgcggggagc acctggaggc    780
ctttgctttg ctggagcgct tcagcggcta ccgggaagac aatatccccc agctggagga    840
cgtctcccgc ttcctgaagg agcgcacggg cttccagctg cggcctgtgg ccggcctgct    900
gtccgcccgg gacttcctgg ccagcctggc cttccgcgtg ttccagtgca cccagtatat    960
ccgccacgcg tcctcgccca tgcactcccc tgagccggac tgctgccacg agctgctggg   1020
gcacgtgccc atgctggccg accgcacctt cgcgcagttc tcgcaggaca ttggcctggc   1080
gtccctgggg gcctcggatg aggaaattga gaagctgtcc acgctgtact ggttcacggt   1140
ggagttcggg ctgtgtaagc agaacgggga ggtgaaggcc tatggtgccg gctgctgtc   1200
ctcctacggg gagctcctgc actgcctgtc tgaggagcct gagattcggg ccttcgaccc   1260
tgaggctgcg gccgtgcagc cctaccaaga ccagacgtac cagtcagtct acttcgtgtc   1320
tgagagcttc agtgacgcca aggacaagct caggagctat gcctcacgca tccagcgccc   1380
cttctccgtg aagttcgacc cgtacacgct ggccatcgac gtgctggaca ccccccaggc   1440
cgtgcggcgc tccctggagg gtgtccagga tgagctggac acccttgccc atgcgctgag   1500
tgccattggc taggtgcacg gcgtccctga gggcccttcc caacctcccc tggtcctgca   1560
ctgtcccgga gctcaggccc tggtgagggg ctgggtcccg ggtgcccccc atgccctccc   1620
tgctgccagg ctcccactgc ccctgcacct gcttctcagc gcaacagctg tgtgtgcccg   1680
tggtgaggtt gtgctgcctg tggtgaggtc ctgtcctggc tcccagggtc ctggggctg   1740
ctgcactgcc ctccgccctt ccctgacact gtctgctgcc ccaatcaccg tcacaataaa   1800
agaaactgtg gtctcta                                                  1817
```

<210> SEQ ID NO 4
<211> LENGTH: 528
<212> TYPE: PRT
<213> ORGANISM: Homo sapiens

<400> SEQUENCE: 4

```
Met Pro Thr Pro Asp Ala Thr Thr Pro Gln Ala Lys Gly Phe Arg Arg
1               5                   10                  15

Ala Val Ser Glu Leu Asp Ala Lys Gln Ala Glu Ala Ile Met Val Arg
            20                  25                  30

Gly Gln Gly Ala Pro Gly Pro Ser Leu Thr Gly Ser Pro Trp Pro Gly
        35                  40                  45

Thr Ala Pro Ala Ala Ser Tyr Thr Pro Thr Pro Arg Ser Pro Arg
    50                  55                  60

Phe Ile Gly Arg Arg Gln Ser Leu Ile Glu Asp Ala Arg Lys Glu Arg
65                  70                  75                  80

Glu Ala Ala Val Ala Ala Ala Ala Ala Val Pro Ser Glu Pro Gly
                85                  90                  95

Asp Pro Leu Glu Ala Val Ala Phe Glu Glu Lys Glu Gly Lys Ala Val
            100                 105                 110

Leu Asn Leu Leu Phe Ser Pro Arg Ala Thr Lys Pro Ser Ala Leu Ser
        115                 120                 125

Arg Ala Val Lys Val Phe Glu Thr Phe Glu Ala Lys Ile His His Leu
    130                 135                 140
```

```
Glu Thr Arg Pro Ala Gln Arg Pro Arg Ala Gly Gly Pro His Leu Glu
145                 150                 155                 160

Tyr Phe Val Arg Leu Glu Val Arg Arg Gly Asp Leu Ala Ala Leu Leu
                165                 170                 175

Ser Gly Val Arg Gln Val Ser Glu Asp Val Arg Ser Pro Ala Gly Pro
            180                 185                 190

Lys Val Pro Trp Phe Pro Arg Lys Val Ser Glu Leu Asp Lys Cys His
        195                 200                 205

His Leu Val Thr Lys Phe Asp Pro Asp Leu Asp Leu His Pro Gly
    210                 215                 220

Phe Ser Asp Gln Val Tyr Arg Gln Arg Lys Leu Ile Ala Glu Ile
225                 230                 235                 240

Ala Phe Gln Tyr Arg His Gly Asp Pro Ile Pro Arg Val Glu Tyr Thr
                245                 250                 255

Ala Glu Glu Ile Ala Thr Trp Lys Glu Val Tyr Thr Thr Leu Lys Gly
                260                 265                 270

Leu Tyr Ala Thr His Ala Cys Gly Glu His Leu Glu Ala Phe Ala Leu
            275                 280                 285

Leu Glu Arg Phe Ser Gly Tyr Arg Glu Asp Asn Ile Pro Gln Leu Glu
    290                 295                 300

Asp Val Ser Arg Phe Leu Lys Glu Arg Thr Gly Phe Gln Leu Arg Pro
305                 310                 315                 320

Val Ala Gly Leu Leu Ser Ala Arg Asp Phe Leu Ala Ser Leu Ala Phe
                325                 330                 335

Arg Val Phe Gln Cys Thr Gln Tyr Ile Arg His Ala Ser Ser Pro Met
                340                 345                 350

His Ser Pro Glu Pro Asp Cys Cys His Glu Leu Leu Gly His Val Pro
            355                 360                 365

Met Leu Ala Asp Arg Thr Phe Ala Gln Phe Ser Gln Asp Ile Gly Leu
    370                 375                 380

Ala Ser Leu Gly Ala Ser Asp Glu Glu Ile Glu Lys Leu Ser Thr Leu
385                 390                 395                 400

Tyr Trp Phe Thr Val Glu Phe Gly Leu Cys Lys Gln Asn Gly Glu Val
                405                 410                 415

Lys Ala Tyr Gly Ala Gly Leu Leu Ser Ser Tyr Gly Glu Leu Leu His
                420                 425                 430

Cys Leu Ser Glu Glu Pro Glu Ile Arg Ala Phe Asp Pro Glu Ala Ala
            435                 440                 445

Ala Val Gln Pro Tyr Gln Asp Gln Thr Tyr Gln Ser Val Tyr Phe Val
450                 455                 460

Ser Glu Ser Phe Ser Asp Ala Lys Asp Lys Leu Arg Ser Tyr Ala Ser
465                 470                 475                 480

Arg Ile Gln Arg Pro Phe Ser Val Lys Phe Asp Pro Tyr Thr Leu Ala
                485                 490                 495

Ile Asp Val Leu Asp Ser Pro Gln Ala Val Arg Arg Ser Leu Glu Gly
                500                 505                 510

Val Gln Asp Glu Leu Asp Thr Leu Ala His Ala Leu Ser Ala Ile Gly
            515                 520                 525

<210> SEQ ID NO 5
<211> LENGTH: 1794
<212> TYPE: DNA
<213> ORGANISM: Homo sapiens

<400> SEQUENCE: 5
```

-continued

```
gacatcagcc gatgcgaagg gcggggccgc ggctataaga gcgcgcggcc gcggtccccg    60
accctcagca gccagcccgg cccgcccgcg cccgtccgca gccgcccgcc agacgcgccc   120
agtatgaggg agatcgtgca catccaggcc ggccagtgcg gcaaccagat cggggccaag   180
ttctgggaag tcatcagtga tgagcatggc atcgacccca cgcgcaacta cgtgggcgac   240
tcggacttgc agctggagcg gatcagcgtc tactacaacg aggcctcttc tcacaagtac   300
gtgcctcgag ccattctggt ggacctggaa cccggaacca tggacagtgt ccgctcaggg   360
gcctttggac atctcttcag gcctgacaat tcatctttg gtcagagtgg ggccggcaac   420
aactgggcca agggtcacta cacgaggggg cggagctgg tggattcggt cctggatgtg    480
gtgcggaagg agtgtgaaaa ctgcgactgc ctgcagggct ccagctgac ccactcgctg     540
gggggcggca cgggctccgg catgggcacg ttgctcatca gcaaggtgcg tgaggagtat    600
cccgaccgca tcatgaacac cttcagcgtc gtgccctcac ccaaggtgtc agacacggtg   660
gtggagccct acaacgccac gctgtccatc accagctgg tggagaacac ggatgagacc    720
tactgcatcg acaacgaggc gctctacgac atctgcttcc gcaccctcaa gctggccacg   780
cccacctacg ggaccctcaa ccacctggta tcggccacca tgagcggagt caccaccctcc   840
ttgcgcttcc cgggccagct caacgctgac ctgcgcaagc tggccgtcaa catggtgccc   900
ttcccgcgcc tgcacttctt catgcccggc ttcgccccc tcacagcccg ggcagccag    960
cagtaccggg ccctgaccgt gcccgagctc acccagcaga tgttcgatgc caagaacatg  1020
atggccgcct cgacccgcg ccacggccgc tacctgacgg tggccaccgt gttccggggc   1080
cgcatgtcca tgaaggaggt ggacgagcag atgctggcca tccagagcaa gaacagcagc   1140
tacttcgtgg agtggatccc caacaacgtg aaggtggccg tgtgtgacat cccgccccgc   1200
ggcctcaaga tgtcctccac cttcatcggg aacagcacgg ccatccagga gctgttcaag   1260
cgcatctccg agcagttcac ggccatgttc cggcgcaagg ccttcctgca ctggtacacg   1320
ggcgagggca tggacgagat ggagttcacc gaggccgaga gcaacatgaa cgacctggtg   1380
tccgagtacc agcagtacca ggacgccacg gccgaggaag agggcgagat gtacgaagac   1440
gacgaggagg agtcggaggc ccagggcccc aagtgaagct gctcgcagct ggagtgagag   1500
gcaggtggcg gccggggccg aagccagcag tgtctaaacc cccggagcca tcttgctgcc   1560
gacaccctgc tttcccctcg ccctagggct cccttgccgc cctcctgcag tatttatggc   1620
ctcgtcctcc ccacctaggc cacgtgtgag ctgctcctgt ctctgtctta ttgcagctcc   1680
aggcctgacg ttttacggtt ttgttttttta ctggtttgtg tttatatttt cggggatact   1740
taataaatct attgctgtca gatacccta aaaaaaaaaa aaaaaaaaa aaaa            1794
```

<210> SEQ ID NO 6
<211> LENGTH: 450
<212> TYPE: PRT
<213> ORGANISM: Homo sapiens

<400> SEQUENCE: 6

```
Met Arg Glu Ile Val His Ile Gln Ala Gly Gln Cys Gly Asn Gln Ile
1               5                   10                  15

Gly Ala Lys Phe Trp Glu Val Ile Ser Asp Glu His Gly Ile Asp Pro
            20                  25                  30

Ser Gly Asn Tyr Val Gly Asp Ser Asp Leu Gln Leu Glu Arg Ile Ser
        35                  40                  45

Val Tyr Tyr Asn Glu Ala Ser Ser His Lys Tyr Val Pro Arg Ala Ile
```

```
                50                  55                  60
Leu Val Asp Leu Glu Pro Gly Thr Met Asp Ser Val Arg Ser Gly Ala
 65                  70                  75                  80

Phe Gly His Leu Phe Arg Pro Asp Asn Phe Ile Phe Gly Gln Ser Gly
                 85                  90                  95

Ala Gly Asn Asn Trp Ala Lys Gly His Tyr Thr Glu Gly Ala Glu Leu
            100                 105                 110

Val Asp Ser Val Leu Asp Val Val Arg Lys Glu Cys Glu Asn Cys Asp
            115                 120                 125

Cys Leu Gln Gly Phe Gln Leu Thr His Ser Leu Gly Gly Thr Gly
        130                 135                 140

Ser Gly Met Gly Thr Leu Leu Ile Ser Lys Val Arg Glu Glu Tyr Pro
145                 150                 155                 160

Asp Arg Ile Met Asn Thr Phe Ser Val Val Pro Ser Pro Lys Val Ser
                165                 170                 175

Asp Thr Val Val Glu Pro Tyr Asn Ala Thr Leu Ser Ile His Gln Leu
            180                 185                 190

Val Glu Asn Thr Asp Glu Thr Tyr Cys Ile Asp Asn Glu Ala Leu Tyr
        195                 200                 205

Asp Ile Cys Phe Arg Thr Leu Lys Leu Ala Thr Pro Thr Tyr Gly Asp
210                 215                 220

Leu Asn His Leu Val Ser Ala Thr Met Ser Gly Val Thr Thr Ser Leu
225                 230                 235                 240

Arg Phe Pro Gly Gln Leu Asn Ala Asp Leu Arg Lys Leu Ala Val Asn
                245                 250                 255

Met Val Pro Phe Pro Arg Leu His Phe Phe Met Pro Gly Phe Ala Pro
            260                 265                 270

Leu Thr Ala Arg Gly Ser Gln Gln Tyr Arg Ala Leu Thr Val Pro Glu
        275                 280                 285

Leu Thr Gln Gln Met Phe Asp Ala Lys Asn Met Met Ala Ala Cys Asp
    290                 295                 300

Pro Arg His Gly Arg Tyr Leu Thr Val Ala Thr Val Phe Arg Gly Arg
305                 310                 315                 320

Met Ser Met Lys Glu Val Asp Glu Gln Met Leu Ala Ile Gln Ser Lys
                325                 330                 335

Asn Ser Ser Tyr Phe Val Glu Trp Ile Pro Asn Asn Val Lys Val Ala
            340                 345                 350

Val Cys Asp Ile Pro Pro Arg Gly Leu Lys Met Ser Ser Thr Phe Ile
        355                 360                 365

Gly Asn Ser Thr Ala Ile Gln Glu Leu Phe Lys Arg Ile Ser Glu Gln
    370                 375                 380

Phe Thr Ala Met Phe Arg Arg Lys Ala Phe Leu His Trp Tyr Thr Gly
385                 390                 395                 400

Glu Gly Met Asp Glu Met Glu Phe Thr Glu Ala Glu Ser Asn Met Asn
                405                 410                 415

Asp Leu Val Ser Glu Tyr Gln Gln Tyr Gln Asp Ala Thr Ala Glu Glu
            420                 425                 430

Glu Gly Glu Met Tyr Glu Asp Asp Glu Glu Ser Glu Ala Gln Gly
        435                 440                 445

Pro Lys
    450

<210> SEQ ID NO 7
```

<211> LENGTH: 1839
<212> TYPE: DNA
<213> ORGANISM: Homo sapiens

<400> SEQUENCE: 7

```
atcgccagtc tagcccactc cttcataaag ccctcgcatc ccaggagcga gcagagccag      60
agcaggatgg agaggagacg catcacctcc gctgctcgcc gctcctacgt ctcctcaggg     120
gagatgatgg tgggggggcct ggctcctggc cgccgtctgg gtcctggcac ccgcctctcc    180
ctggctcgaa tgccccctcc actcccgacc cgggtggatt tctccctggc tggggcactc    240
aatgctggct tcaaggagac ccgggccagt gagcgggcag agatgatgga gctcaatgac    300
cgcttttgcca gctacatcga aaggttcgc ttcctggaac agcaaaacaa ggcgctggct    360
gctgagctga accagctgcg ggccaaggag cccaccaagc tggcagacgt ctaccaggct    420
gagctgcgag agctgcggct gcggctcgat caactcaccg ccaacagcgc ccggctggag    480
gttgagaggg acaatctggc acaggacctg gccactgtga ggcagaagct ccaggatgaa    540
accaacctga ggctggaagc cgagaacaac ctggctgcct atagacagga agcagatgaa    600
gccacccctgg cccgtctgga tctggagagg aagattgagt cgctggagga ggagatccgg    660
ttcttgagga agatccacga ggaggaggtt cgggaactcc aggagcagct ggcccgacag    720
caggtccatg tggagcttga cgtggccaag ccagacctca ccgcagccct gaaagagatc    780
cgcacgcagt atgaggcaat ggcgtccagc aacatgcatg aagccgaaga gtggtaccgc    840
tccaagtttg cagacctgac agacgctgct gcccgcaacg cggagctgct ccgccaggcc    900
aagcacgaag ccaacgacta ccggcgccag ttgcagtcct tgacctgcga cctggagtct    960
ctgcgcggca cgaacgagtc cctggagagg cagatgcgcg agcaggagga gcggcacgtg    1020
cgggaggcgg ccagttatca ggaggcgctg gcgcggctgg aggaagaggg gcagagcctc    1080
aaggacgaga tggcccgcca cttgcaggag taccaggacc tgctcaatgt caagctggcc    1140
ctggacatcg agatcgccac ctacaggaag ctgctagagg gcgaggagaa ccggatcacc    1200
attcccgtgc agaccttctc caacctgcag attcgagggg gcaaaagcac caaagacggg    1260
gaaaatcaca aggtcacaag atatctcaaa agcctcacaa tacgagttat accaatacag    1320
gctcaccaga ttgtaaatgg aacgccgccg gctcgcggtt agctgcctgc ctctcagaca    1380
cggcgctttg cccagcttga cagggagtga gcctcaccca ccccatcctc ccaatccccc    1440
tgagttccct cttcccaggc ttcccctaaa gggcctggac tgcgtcattt tcccaggaac    1500
tgcagtgccc agcccaggac gtggtacaga gtaactgtac attaaactgg cagagcttgt    1560
tagtggtaaa ggtggtgagt ccttgggtgc gcagtggagc tgctctgggg cctctgagca    1620
agcagcagcc tctgtctcac ctcttcctgt cactgggagg gccccttggg tctcgctgtg    1680
cctggacgcc aggctctctg ctttattctt tcatccctga ggctccatcg ctcagctcag    1740
tgctgactca gttcagagga ttcttccctc aggaccgcag ctcttgcagt gaataaagtt    1800
ttatgttccc tgctcttaat gttaaatatt aaaaaaaaa                           1839
```

<210> SEQ ID NO 8
<211> LENGTH: 432
<212> TYPE: PRT
<213> ORGANISM: Homo sapiens

<400> SEQUENCE: 8

```
Met Glu Arg Arg Arg Ile Thr Ser Ala Ala Arg Arg Ser Tyr Val Ser
1               5                   10                  15
```

```
Ser Gly Glu Met Met Val Gly Gly Leu Ala Pro Gly Arg Arg Leu Gly
             20                  25                  30

Pro Gly Thr Arg Leu Ser Leu Ala Arg Met Pro Pro Leu Pro Thr
         35                  40                  45

Arg Val Asp Phe Ser Leu Ala Gly Ala Leu Asn Ala Gly Phe Lys Glu
     50                  55                  60

Thr Arg Ala Ser Glu Arg Ala Glu Met Met Glu Leu Asn Asp Arg Phe
 65                  70                  75                  80

Ala Ser Tyr Ile Glu Lys Val Arg Phe Leu Gln Gln Asn Lys Ala
                 85                  90                  95

Leu Ala Ala Glu Leu Asn Gln Leu Arg Ala Lys Glu Pro Thr Lys Leu
             100                 105                 110

Ala Asp Val Tyr Gln Ala Glu Leu Arg Glu Leu Arg Leu Arg Leu Asp
         115                 120                 125

Gln Leu Thr Ala Asn Ser Ala Arg Leu Glu Val Glu Arg Asp Asn Leu
     130                 135                 140

Ala Gln Asp Leu Ala Thr Val Arg Gln Lys Leu Gln Asp Glu Thr Asn
145                 150                 155                 160

Leu Arg Leu Glu Ala Glu Asn Asn Leu Ala Ala Tyr Arg Gln Glu Ala
                 165                 170                 175

Asp Glu Ala Thr Leu Ala Arg Leu Asp Leu Glu Arg Lys Ile Glu Ser
             180                 185                 190

Leu Glu Glu Glu Ile Arg Phe Leu Arg Lys Ile His Glu Glu Val
         195                 200                 205

Arg Glu Leu Gln Glu Gln Leu Ala Arg Gln Gln Val His Val Glu Leu
     210                 215                 220

Asp Val Ala Lys Pro Asp Leu Thr Ala Ala Leu Lys Glu Ile Arg Thr
225                 230                 235                 240

Gln Tyr Glu Ala Met Ala Ser Ser Asn Met His Glu Ala Glu Glu Trp
                 245                 250                 255

Tyr Arg Ser Lys Phe Ala Asp Leu Thr Asp Ala Ala Arg Asn Ala
             260                 265                 270

Glu Leu Leu Arg Gln Ala Lys His Glu Ala Asn Asp Tyr Arg Arg Gln
         275                 280                 285

Leu Gln Ser Leu Thr Cys Asp Leu Glu Ser Leu Arg Gly Thr Asn Glu
     290                 295                 300

Ser Leu Glu Arg Gln Met Arg Glu Gln Glu Glu Arg His Val Arg Glu
305                 310                 315                 320

Ala Ala Ser Tyr Gln Glu Ala Leu Ala Arg Leu Glu Glu Glu Gly Gln
                 325                 330                 335

Ser Leu Lys Asp Glu Met Ala Arg His Leu Gln Glu Tyr Gln Asp Leu
             340                 345                 350

Leu Asn Val Lys Leu Ala Leu Asp Ile Glu Ile Ala Thr Tyr Arg Lys
         355                 360                 365

Leu Leu Glu Gly Glu Glu Asn Arg Ile Thr Ile Pro Val Gln Thr Phe
     370                 375                 380

Ser Asn Leu Gln Ile Arg Glu Thr Ser Leu Asp Thr Lys Ser Val Ser
385                 390                 395                 400

Glu Gly His Leu Lys Arg Asn Ile Val Val Lys Thr Val Glu Met Arg
                 405                 410                 415

Asp Gly Glu Val Ile Lys Glu Ser Lys Gln Glu His Lys Asp Val Met
             420                 425                 430
```

<210> SEQ ID NO 9
<211> LENGTH: 1135
<212> TYPE: DNA
<213> ORGANISM: Homo sapiens

<400> SEQUENCE: 9

```
gggcagaggg aataagaggc tgcctctgcc caccagtcct gccgcccagg acccgcagca    60
gagacgacgc ctgcagcaag gagaccagga aggggtgaga caaggaagag gatgtctgag   120
ctggagaagg ccatggtggc cctcatcgac gttttccacc aatattctgg aagggaggga   180
gacaagcaca agctgaagaa atccgaactg aaggagctca tcaacaatga gctttcccat   240
ttcttagagg aaatcaaaga gcaggaggtt gtggacaaag tcatggaaac actggacaat   300
gatggagacg gcgaatgtga cttccaggaa ttcatggcct tgttgccat ggttactact   360
gcctgccacg agttctttga acatgagtga gattagaaag cagccaaacc tttcctgtaa   420
cagagacggt catgcaagaa agcagacagc aagggcttgc agcctagtag gagctgagct   480
ttccagccgt gttgtagcta attaggaagc ttgatttgct ttgtgattga aaaattgaaa   540
acctctttcc aaaggctgtt ttaacggcct gcatcattct ttctgctata ttaggcctgt   600
gtgtaagctg actggcccca gggactcttg ttaacagtaa cttaggagtc aggtctcagt   660
gataaagcgt gcaccgtgca gcccgccatg ccgtgtaga ccctaacccg gagggaaccc    720
tgactacaga aattaccccg gggcacccct aaaacttcca ctacctttaa aaaacaaagc   780
cttatccagc attatttgaa aacactgctg ttctttaaat gcgttcctca tccatgcaga   840
taacagctgg ttggccggtg tggccctgca agggcgtggt ggcttcggcc tgcttcccgg   900
gatgcgcctg atcaccaggt gaacgctcag cgctggcagc gctcctggaa aaagcaactc   960
catcagaact cgcaatccga gccagctctg ggggctccag cgtggcctcc gtgacccatg  1020
cgattcaagt cgcggctgca ggatccttgc ctccaacgtg cctccagcac atgcggcttc  1080
cgagggcact accgggggct ctgagccacc gcgagggcct gcgttcaata aaaag       1135
```

<210> SEQ ID NO 10
<211> LENGTH: 92
<212> TYPE: PRT
<213> ORGANISM: Homo sapiens

<400> SEQUENCE: 10

```
Met Ser Glu Leu Glu Lys Ala Met Val Ala Leu Ile Asp Val Phe His
1               5                   10                  15

Gln Tyr Ser Gly Arg Glu Gly Asp Lys His Lys Leu Lys Lys Ser Glu
            20                  25                  30

Leu Lys Glu Leu Ile Asn Asn Glu Leu Ser His Phe Leu Glu Glu Ile
        35                  40                  45

Lys Glu Gln Glu Val Val Asp Lys Val Met Glu Thr Leu Asp Asn Asp
    50                  55                  60

Gly Asp Gly Glu Cys Asp Phe Gln Glu Phe Met Ala Phe Val Ala Met
65                  70                  75                  80

Val Thr Thr Ala Cys His Glu Phe Phe Glu His Glu
                85                  90
```

<210> SEQ ID NO 11
<211> LENGTH: 422
<212> TYPE: PRT
<213> ORGANISM: Homo sapiens

<400> SEQUENCE: 11

-continued

```
Met Gln Asn Ser His Ser Gly Val Asn Gln Leu Gly Gly Val Phe Val
1               5                   10                  15

Asn Gly Arg Pro Leu Pro Asp Ser Thr Arg Gln Lys Ile Val Glu Leu
            20                  25                  30

Ala His Ser Gly Ala Arg Pro Cys Asp Ile Ser Arg Ile Leu Gln Val
            35                  40                  45

Ser Asn Gly Cys Val Ser Lys Ile Leu Gly Arg Tyr Tyr Glu Thr Gly
50                      55                  60

Ser Ile Arg Pro Arg Ala Ile Gly Gly Ser Lys Pro Arg Val Ala Thr
65                  70                  75                  80

Pro Glu Val Val Ser Lys Ile Ala Gln Tyr Lys Arg Glu Cys Pro Ser
                85                  90                  95

Ile Phe Ala Trp Glu Ile Arg Asp Arg Leu Leu Ser Glu Gly Val Cys
            100                 105                 110

Thr Asn Asp Asn Ile Pro Ser Val Ser Ser Ile Asn Arg Val Leu Arg
            115                 120                 125

Asn Leu Ala Ser Glu Lys Gln Gln Met Gly Ala Asp Gly Met Tyr Asp
130                 135                 140

Lys Leu Arg Met Leu Asn Gly Gln Thr Gly Ser Trp Gly Thr Arg Pro
145                 150                 155                 160

Gly Trp Tyr Pro Gly Thr Ser Val Pro Gly Gln Pro Thr Gln Asp Gly
                165                 170                 175

Cys Gln Gln Gln Glu Gly Gly Gly Glu Asn Thr Asn Ser Ile Ser Ser
            180                 185                 190

Asn Gly Glu Asp Ser Asp Glu Ala Gln Met Arg Leu Gln Leu Lys Arg
            195                 200                 205

Lys Leu Gln Arg Asn Arg Thr Ser Phe Thr Gln Glu Gln Ile Glu Ala
210                 215                 220

Leu Glu Lys Glu Phe Glu Arg Thr His Tyr Pro Asp Val Phe Ala Arg
225                 230                 235                 240

Glu Arg Leu Ala Ala Lys Ile Asp Leu Pro Glu Ala Arg Ile Gln Val
                245                 250                 255

Trp Phe Ser Asn Arg Arg Ala Lys Trp Arg Arg Glu Glu Lys Leu Arg
            260                 265                 270

Asn Gln Arg Arg Gln Ala Ser Asn Thr Pro Ser His Ile Pro Ile Ser
            275                 280                 285

Ser Ser Phe Ser Thr Ser Val Tyr Gln Pro Ile Pro Gln Pro Thr Thr
290                 295                 300

Pro Val Ser Ser Phe Thr Ser Gly Ser Met Leu Gly Arg Thr Asp Thr
305                 310                 315                 320

Ala Leu Thr Asn Thr Tyr Ser Ala Leu Pro Pro Met Pro Ser Phe Thr
                325                 330                 335

Met Ala Asn Asn Leu Pro Met Gln Pro Pro Val Pro Ser Gln Thr Ser
            340                 345                 350

Ser Tyr Ser Cys Met Leu Pro Thr Ser Pro Ser Val Asn Gly Arg Ser
            355                 360                 365

Tyr Asp Thr Tyr Thr Pro Pro His Met Gln Thr His Met Asn Ser Gln
370                 375                 380

Pro Met Gly Thr Ser Gly Thr Thr Ser Thr Gly Leu Ile Ser Pro Gly
385                 390                 395                 400

Val Ser Val Pro Val Gln Val Pro Gly Ser Glu Pro Asp Met Ser Gln
                405                 410                 415

Tyr Trp Pro Arg Leu Gln
```

420

<210> SEQ ID NO 12
<211> LENGTH: 391
<212> TYPE: PRT
<213> ORGANISM: Homo sapiens

<400> SEQUENCE: 12

Met Tyr Ser Met Met Met Glu Thr Asp Leu His Ser Pro Gly Gly Ala
1               5                   10                  15

Gln Ala Pro Thr Asn Leu Ser Gly Pro Ala Gly Ala Gly Gly Gly Gly
            20                  25                  30

Gly Gly Gly Gly Gly Gly Gly Gly Gly Ala Lys Ala Asn Gln
        35                  40                  45

Asp Arg Val Lys Arg Pro Met Asn Ala Phe Met Val Trp Ser Arg Gly
    50                  55                  60

Gln Arg Arg Lys Met Ala Gln Glu Asn Pro Lys Met His Asn Ser Glu
65                  70                  75                  80

Ile Ser Lys Arg Leu Gly Ala Glu Trp Lys Val Met Ser Glu Ala Glu
                85                  90                  95

Lys Arg Pro Phe Ile Asp Glu Ala Lys Arg Leu Arg Ala Leu His Met
            100                 105                 110

Lys Glu His Pro Asp Tyr Lys Tyr Arg Pro Arg Arg Lys Thr Lys Thr
        115                 120                 125

Leu Leu Lys Lys Asp Lys Tyr Ser Leu Ala Gly Gly Leu Leu Ala Ala
    130                 135                 140

Gly Ala Gly Gly Gly Ala Ala Val Ala Met Gly Val Gly Val Gly Val
145                 150                 155                 160

Val Gly Ala Ala Ala Val Gly Gln Arg Leu Glu Ser Pro Gly Gly Ala
                165                 170                 175

Ala Gly Gly Gly Tyr Ala His Val Asn Gly Trp Ala Asn Gly Ala Tyr
            180                 185                 190

Pro Gly Ser Val Ala Ala Ala Ala Ala Ala Ala Met Met Gln Glu
        195                 200                 205

Ala Gln Leu Ala Tyr Gly Gln His Pro Gly Ala Gly Gly Ala His Pro
    210                 215                 220

His Ala His Pro Ala His Pro His Pro His His Pro His Ala His Pro
225                 230                 235                 240

His Asn Pro Gln Pro Met His Arg Tyr Asp Met Gly Ala Leu Gln Tyr
                245                 250                 255

Ser Pro Ile Ser Asn Ser Gln Gly Tyr Met Ser Ala Ser Pro Ser Gly
            260                 265                 270

Tyr Gly Gly Leu Pro Tyr Gly Ala Ala Ala Ala Ala Ala Ala Ala
        275                 280                 285

Gly Gly Ala His Gln Asn Ser Ala Val Ala Ala Ala Ala Ala Ala
    290                 295                 300

Ala Ala Ser Ser Gly Ala Leu Gly Ala Leu Gly Ser Leu Val Lys Ser
305                 310                 315                 320

Glu Pro Ser Gly Ser Pro Ala Pro Ala His Ser Arg Ala Pro Cys
                325                 330                 335

Pro Gly Asp Leu Arg Glu Met Ile Ser Met Tyr Leu Pro Ala Gly Glu
            340                 345                 350

Gly Gly Asp Pro Ala Ala Ala Ala Ala Ala Ala Gln Ser Arg Leu
        355                 360                 365

His Ser Leu Pro Gln His Tyr Gln Gly Ala Gly Ala Gly Val Asn Gly
370                 375                 380

Thr Val Pro Leu Thr His Ile
385                 390

<210> SEQ ID NO 13
<211> LENGTH: 317
<212> TYPE: PRT
<213> ORGANISM: Homo sapiens

<400> SEQUENCE: 13

Met Tyr Asn Met Met Glu Thr Glu Leu Lys Pro Pro Gly Pro Gln Gln
1               5                   10                  15

Thr Ser Gly Gly Gly Gly Asn Ser Thr Ala Ala Ala Ala Gly Gly
            20                  25                  30

Asn Gln Lys Asn Ser Pro Asp Arg Val Lys Arg Pro Met Asn Ala Phe
            35                  40                  45

Met Val Trp Ser Arg Gly Gln Arg Arg Lys Met Ala Gln Glu Asn Pro
50                  55                  60

Lys Met His Asn Ser Glu Ile Ser Lys Arg Leu Gly Ala Glu Trp Lys
65                  70                  75                  80

Leu Leu Ser Glu Thr Glu Lys Arg Pro Phe Ile Asp Glu Ala Lys Arg
                85                  90                  95

Leu Arg Ala Leu His Met Lys Glu His Pro Asp Tyr Lys Tyr Arg Pro
            100                 105                 110

Arg Arg Lys Thr Lys Thr Leu Met Lys Lys Asp Lys Tyr Thr Leu Pro
            115                 120                 125

Gly Gly Leu Leu Ala Pro Gly Gly Asn Ser Met Ala Ser Gly Val Gly
130                 135                 140

Val Gly Ala Gly Leu Gly Ala Gly Val Asn Gln Arg Met Asp Ser Tyr
145                 150                 155                 160

Ala His Met Asn Gly Trp Ser Asn Gly Ser Tyr Ser Met Met Gln Asp
                165                 170                 175

Gln Leu Gly Tyr Pro Gln His Pro Gly Leu Asn Ala His Gly Ala Ala
            180                 185                 190

Gln Met Gln Pro Met His Arg Tyr Asp Val Ser Ala Leu Gln Tyr Asn
            195                 200                 205

Ser Met Thr Ser Ser Gln Thr Tyr Met Asn Gly Ser Pro Thr Tyr Ser
210                 215                 220

Met Ser Tyr Ser Gln Gln Gly Thr Pro Gly Met Ala Leu Gly Ser Met
225                 230                 235                 240

Gly Ser Val Val Lys Ser Glu Ala Ser Ser Pro Pro Val Val Thr
                245                 250                 255

Ser Ser Ser His Ser Arg Ala Pro Cys Gln Ala Gly Asp Leu Arg Asp
            260                 265                 270

Met Ile Ser Met Tyr Leu Pro Gly Ala Glu Val Pro Glu Pro Ala Ala
            275                 280                 285

Pro Ser Arg Leu His Met Ser Gln His Tyr Gln Ser Gly Pro Val Pro
290                 295                 300

Gly Thr Ala Ile Asn Gly Thr Leu Pro Leu Ser His Met
305                 310                 315

<210> SEQ ID NO 14
<211> LENGTH: 1621
<212> TYPE: PRT
<213> ORGANISM: Homo sapiens

<400> SEQUENCE: 14

Met Glu Gly Cys Met Gly Glu Glu Ser Phe Gln Met Trp Glu Leu Asn
1               5                   10                  15

Arg Arg Leu Glu Ala Tyr Leu Ala Arg Val Lys Ala Leu Glu Glu Gln
            20                  25                  30

Asn Glu Leu Leu Ser Ala Glu Leu Gly Gly Leu Arg Ala Gln Ser Ala
            35                  40                  45

Asp Thr Ser Trp Arg Ala His Ala Asp Asp Glu Leu Ala Ala Leu Arg
    50                  55                  60

Ala Leu Val Asp Gln Arg Trp Arg Glu Lys His Ala Ala Glu Val Ala
65                  70                  75                  80

Arg Asp Asn Leu Ala Glu Leu Glu Gly Val Ala Gly Arg Cys Gln
                85                  90                  95

Gln Leu Arg Leu Ala Arg Glu Arg Thr Thr Glu Glu Val Ala Arg Asn
            100                 105                 110

Arg Arg Ala Val Glu Ala Glu Lys Cys Ala Arg Ala Trp Leu Ser Ser
            115                 120                 125

Gln Val Ala Glu Leu Glu Arg Glu Leu Glu Ala Leu Arg Val Ala His
    130                 135                 140

Glu Glu Glu Arg Val Gly Leu Asn Ala Gln Ala Ala Cys Ala Pro Arg
145                 150                 155                 160

Cys Pro Ala Pro Pro Arg Gly Pro Pro Ala Pro Ala Pro Glu Val Glu
                165                 170                 175

Glu Leu Ala Arg Arg Leu Gly Glu Ala Trp Arg Gly Ala Val Arg Gly
            180                 185                 190

Tyr Gln Glu Arg Val Ala His Met Glu Thr Ser Leu Gly Gln Ala Arg
    195                 200                 205

Glu Arg Leu Gly Arg Ala Val Gln Gly Ala Arg Glu Gly Arg Leu Glu
210                 215                 220

Leu Gln Gln Leu Gln Ala Glu Arg Gly Gly Leu Leu Glu Arg Arg Ala
225                 230                 235                 240

Ala Leu Glu Gln Arg Leu Glu Gly Arg Trp Gln Glu Arg Leu Arg Ala
                245                 250                 255

Thr Glu Lys Phe Gln Leu Ala Val Glu Ala Leu Glu Gln Glu Lys Gln
            260                 265                 270

Gly Leu Gln Ser Gln Ile Ala Gln Val Leu Glu Gly Arg Gln Gln Leu
            275                 280                 285

Ala His Leu Lys Met Ser Leu Ser Leu Glu Val Ala Thr Tyr Arg Thr
290                 295                 300

Leu Leu Glu Ala Glu Asn Ser Arg Leu Gln Thr Pro Gly Gly Gly Ser
305                 310                 315                 320

Lys Thr Ser Leu Ser Phe Gln Asp Pro Lys Leu Glu Leu Gln Phe Pro
                325                 330                 335

Arg Thr Pro Glu Gly Arg Arg Leu Gly Ser Leu Leu Pro Val Leu Ser
            340                 345                 350

Pro Thr Ser Leu Pro Ser Pro Leu Pro Ala Thr Leu Glu Thr Pro Val
            355                 360                 365

Pro Ala Phe Leu Lys Asn Gln Glu Phe Leu Gln Ala Arg Thr Pro Thr
    370                 375                 380

Leu Ala Ser Thr Pro Ile Pro Pro Thr Pro Gln Ala Pro Ser Pro Ala
385                 390                 395                 400

Val Asp Ala Glu Ile Arg Ala Gln Asp Ala Pro Leu Ser Leu Leu Gln

```
                405                 410                 415
Thr Gln Gly Gly Arg Lys Gln Ala Pro Glu Pro Leu Arg Ala Glu Ala
            420                 425                 430

Arg Val Ala Ile Pro Ala Ser Val Leu Pro Gly Pro Glu Glu Pro Gly
            435                 440                 445

Gly Gln Arg Gln Glu Ala Ser Thr Gly Gln Ser Pro Glu Asp His Ala
            450                 455                 460

Ser Leu Ala Pro Pro Leu Ser Pro Asp His Ser Ser Leu Glu Ala Lys
465                 470                 475                 480

Asp Gly Glu Ser Gly Gly Ser Arg Val Phe Ser Ile Cys Arg Gly Glu
                485                 490                 495

Gly Glu Gly Gln Ile Trp Gly Leu Val Glu Lys Glu Thr Ala Ile Glu
            500                 505                 510

Gly Lys Val Val Ser Ser Leu Gln Gln Glu Ile Trp Glu Glu Glu Asp
            515                 520                 525

Leu Asn Arg Lys Glu Ile Gln Asp Ser Gln Val Pro Leu Glu Lys Glu
530                 535                 540

Thr Leu Lys Ser Leu Gly Glu Glu Ile Gln Glu Ser Leu Lys Thr Leu
545                 550                 555                 560

Glu Asn Gln Ser His Glu Thr Leu Glu Arg Glu Asn Gln Glu Cys Pro
                565                 570                 575

Arg Ser Leu Glu Glu Asp Leu Glu Thr Leu Lys Ser Leu Glu Lys Glu
            580                 585                 590

Asn Lys Glu Leu Leu Lys Asp Val Glu Val Val Arg Pro Leu Glu Lys
            595                 600                 605

Glu Ala Val Gly Gln Leu Lys Pro Thr Gly Lys Glu Asp Thr Gln Thr
            610                 615                 620

Leu Gln Ser Leu Gln Lys Glu Asn Gln Glu Leu Met Lys Ser Leu Glu
625                 630                 635                 640

Gly Asn Leu Glu Thr Phe Leu Phe Pro Gly Thr Glu Asn Gln Glu Leu
                645                 650                 655

Val Ser Ser Leu Gln Glu Asn Leu Glu Ser Leu Thr Ala Leu Glu Lys
            660                 665                 670

Glu Asn Gln Glu Pro Leu Arg Ser Pro Glu Val Gly Asp Glu Glu Ala
            675                 680                 685

Leu Arg Pro Leu Thr Lys Glu Asn Gln Glu Pro Leu Arg Ser Leu Glu
            690                 695                 700

Asp Glu Asn Lys Glu Ala Phe Arg Ser Leu Glu Lys Glu Asn Gln Glu
705                 710                 715                 720

Pro Leu Lys Thr Leu Glu Glu Asp Gln Ser Ile Val Arg Pro Leu
                725                 730                 735

Glu Thr Glu Asn His Lys Ser Leu Arg Ser Leu Glu Glu Gln Asp Gln
                740                 745                 750

Glu Thr Leu Arg Thr Leu Glu Lys Glu Thr Gln Gln Arg Arg Arg Ser
            755                 760                 765

Leu Gly Glu Gln Asp Gln Met Thr Leu Arg Pro Pro Glu Lys Val Asp
            770                 775                 780

Leu Glu Pro Leu Lys Ser Leu Asp Gln Glu Ile Ala Arg Pro Leu Glu
785                 790                 795                 800

Asn Glu Asn Gln Glu Phe Leu Lys Ser Leu Lys Glu Glu Ser Val Glu
                805                 810                 815

Ala Val Lys Ser Leu Glu Thr Glu Ile Leu Glu Ser Leu Lys Ser Ala
            820                 825                 830
```

-continued

```
Gly Gln Glu Asn Leu Glu Thr Leu Lys Ser Pro Gln Thr Gln Ala Pro
        835                 840                 845

Leu Trp Thr Pro Glu Glu Ile Asn Gln Gly Ala Met Asn Pro Leu Glu
    850                 855                 860

Lys Glu Ile Gln Glu Pro Leu Glu Ser Val Glu Val Asn Gln Glu Thr
865                 870                 875                 880

Phe Arg Leu Leu Glu Glu Asn Gln Glu Ser Leu Arg Ser Leu Gly
            885                 890                 895

Ala Trp Asn Leu Glu Asn Leu Arg Ser Pro Glu Glu Val Asp Lys Glu
            900                 905                 910

Ser Gln Arg Asn Leu Glu Glu Glu Asn Leu Gly Lys Gly Glu Tyr
            915                 920                 925

Gln Glu Ser Leu Arg Ser Leu Glu Glu Gly Gln Glu Leu Pro Gln
            930                 935                 940

Ser Ala Asp Val Gln Arg Trp Glu Asp Thr Val Glu Lys Asp Gln Glu
945                 950                 955                 960

Leu Ala Gln Glu Ser Pro Pro Gly Met Ala Gly Val Glu Asn Glu Asp
                965                 970                 975

Glu Ala Glu Leu Asn Leu Arg Glu Gln Asp Gly Phe Thr Gly Lys Glu
            980                 985                 990

Glu Val Val Glu Gln Gly Glu Leu  Asn Ala Thr Glu Glu  Val Trp Ile
            995                 1000                1005

Pro Gly  Glu Gly His Pro Glu  Ser Pro Glu Pro Lys  Glu Gln Arg
    1010                1015                1020

Gly Leu  Val Glu Gly Ala Ser  Val Lys Gly Gly Ala  Glu Gly Leu
    1025                1030                1035

Gln Asp  Pro Glu Gly Gln Ser  Gln Gln Val Gly Ala  Pro Gly Leu
    1040                1045                1050

Gln Ala  Pro Gln Gly Leu Pro  Glu Ala Ile Glu Pro  Leu Val Glu
    1055                1060                1065

Asp Asp  Val Ala Pro Gly Gly  Asp Gln Ala Ser Pro  Glu Val Met
    1070                1075                1080

Leu Gly  Ser Glu Pro Ala Met  Gly Glu Ser Ala Ala  Gly Ala Glu
    1085                1090                1095

Pro Gly  Pro Gly Gln Gly Val  Gly Gly Leu Gly Asp  Pro Gly His
    1100                1105                1110

Leu Thr  Arg Glu Glu Val Met  Glu Pro Pro Leu Glu  Glu Glu Ser
    1115                1120                1125

Leu Glu  Ala Lys Arg Val Gln  Gly Leu Glu Gly Pro  Arg Lys Asp
    1130                1135                1140

Leu Glu  Glu Ala Gly Gly Leu  Gly Thr Glu Phe Ser  Glu Leu Pro
    1145                1150                1155

Gly Lys  Ser Arg Asp Pro Trp  Glu Pro Pro Arg Glu  Gly Arg Glu
    1160                1165                1170

Glu Ser  Glu Ala Glu Ala Pro  Arg Gly Ala Glu Glu  Ala Phe Pro
    1175                1180                1185

Ala Glu  Thr Leu Gly His Thr  Gly Ser Asp Ala Pro  Ser Pro Trp
    1190                1195                1200

Pro Leu  Gly Ser Glu Glu Ala  Glu Glu Asp Val Pro  Pro Val Leu
    1205                1210                1215

Val Ser  Pro Ser Pro Thr Tyr  Thr Pro Ile Leu Glu  Asp Ala Pro
    1220                1225                1230
```

```
Gly Pro Gln Pro Gln Ala Glu Gly Ser Gln Glu Ala  Ser Trp Gly
    1235                1240                1245

Val Gln Gly Arg Ala Glu Ala Leu Gly Lys Val Glu  Ser Glu Gln
    1250                1255                1260

Glu Glu Leu Gly Ser Gly Glu Ile Pro Glu Gly Pro  Gln Glu Glu
    1265                1270                1275

Gly Glu Glu Ser Arg Glu Glu Ser Glu Asp Glu Leu  Leu Gly Glu
    1280                1285                1290

Thr Leu Pro Asp Ser Thr Pro Leu Gly Phe Tyr Leu  Arg Ser Pro
    1295                1300                1305

Thr Ser Pro Arg Trp Asp Pro Thr Gly Glu Gln Arg  Pro Pro Pro
    1310                1315                1320

Gln Gly Glu Thr Gly Lys Glu Gly Trp Asp Pro Ala  Val Leu Ala
    1325                1330                1335

Ser Glu Gly Leu Glu Ala Pro Pro Ser Glu Lys Glu  Glu Gly Glu
    1340                1345                1350

Glu Gly Glu Glu Glu Cys Gly Arg Asp Ser Asp Leu  Ser Glu Glu
    1355                1360                1365

Phe Glu Asp Leu Gly Thr Glu Ala Pro Phe Leu Pro  Gly Val Pro
    1370                1375                1380

Gly Glu Val Ala Glu Pro Leu Gly Gln Val Pro Gln  Leu Leu Leu
    1385                1390                1395

Asp Pro Ala Ala Trp Asp Arg Asp Gly Glu Ser Asp  Gly Phe Ala
    1400                1405                1410

Asp Glu Glu Glu Ser Gly Glu Glu Gly Glu Glu Asp  Gln Glu Glu
    1415                1420                1425

Gly Arg Glu Pro Gly Ala Gly Arg Trp Gly Pro Gly  Ser Ser Val
    1430                1435                1440

Gly Ser Leu Gln Ala Leu Ser Ser Ser Gln Arg Gly  Glu Phe Leu
    1445                1450                1455

Glu Ser Asp Ser Val Ser Val Ser Val Pro Trp Asp  Asp Ser Leu
    1460                1465                1470

Arg Gly Ala Val Ala Gly Ala Pro Lys Thr Ala Leu  Glu Thr Glu
    1475                1480                1485

Ser Gln Asp Ser Ala Glu Pro Ser Gly Ser Glu Glu  Glu Ser Asp
    1490                1495                1500

Pro Val Ser Leu Glu Arg Glu Asp Lys Val Pro Gly  Pro Leu Glu
    1505                1510                1515

Ile Pro Ser Gly Met Glu Asp Ala Gly Pro Gly Ala  Asp Ile Ile
    1520                1525                1530

Gly Val Asn Gly Gln Gly Pro Asn Leu Glu Gly Lys  Ser Gln His
    1535                1540                1545

Val Asn Gly Gly Val Met Asn Gly Leu Glu Gln Ser  Glu Glu Val
    1550                1555                1560

Gly Gln Gly Met Pro Leu Val Ser Glu Gly Asp Arg  Gly Ser Pro
    1565                1570                1575

Phe Gln Glu Glu Glu Gly Ser Ala Leu Lys Thr Ser  Trp Ala Gly
    1580                1585                1590

Ala Pro Val His Leu Gly Gln Gly Gln Phe Leu Lys  Phe Thr Gln
    1595                1600                1605

Arg Glu Gly Asp Arg Glu Ser Trp Ser Ser Gly Glu  Asp
    1610                1615                1620
```

```
<210> SEQ ID NO 15
<211> LENGTH: 382
<212> TYPE: PRT
<213> ORGANISM: Homo sapiens

<400> SEQUENCE: 15

Met Leu Asp Gly Leu Lys Met Glu Glu Asn Phe Gln Ser Ala Ile Asp
1               5                   10                  15

Thr Ser Ala Ser Phe Ser Ser Leu Leu Gly Arg Ala Val Ser Pro Lys
            20                  25                  30

Ser Val Cys Glu Gly Cys Gln Arg Val Ile Leu Asp Arg Phe Leu Leu
        35                  40                  45

Arg Leu Asn Asp Ser Phe Trp His Glu Gln Cys Val Gln Cys Ala Ser
50                  55                  60

Cys Lys Glu Pro Leu Glu Thr Thr Cys Phe Tyr Arg Asp Lys Lys Leu
65                  70                  75                  80

Tyr Cys Lys Tyr Asp Tyr Glu Lys Leu Phe Ala Val Lys Cys Gly Gly
                85                  90                  95

Cys Phe Glu Ala Ile Ala Pro Asn Glu Phe Val Met Arg Ala Gln Lys
            100                 105                 110

Ser Val Tyr His Leu Ser Cys Phe Cys Cys Cys Val Cys Glu Arg Gln
        115                 120                 125

Leu Gln Lys Gly Asp Glu Phe Val Leu Lys Glu Gly Gln Leu Leu Cys
130                 135                 140

Lys Gly Asp Tyr Glu Lys Glu Arg Glu Leu Leu Ser Leu Val Ser Pro
145                 150                 155                 160

Ala Ala Ser Asp Ser Gly Lys Ser Asp Asp Glu Glu Ser Leu Cys Lys
                165                 170                 175

Ser Ala His Gly Ala Gly Lys Gly Thr Ala Glu Glu Gly Lys Asp His
            180                 185                 190

Lys Arg Pro Lys Arg Pro Arg Thr Ile Leu Thr Thr Gln Gln Arg Arg
        195                 200                 205

Ala Phe Lys Ala Ser Phe Glu Val Ser Ser Lys Pro Cys Arg Lys Val
210                 215                 220

Arg Glu Thr Leu Ala Ala Glu Thr Gly Leu Ser Val Arg Val Val Gln
225                 230                 235                 240

Val Trp Phe Gln Asn Gln Arg Ala Lys Met Lys Lys Leu Ala Arg Arg
                245                 250                 255

Gln Gln Gln Gln Gln Gln Asp Gln Gln Asn Thr Gln Arg Leu Ser Ser
            260                 265                 270

Ala Gln Thr Asn Gly Gly Gly Ser Ala Gly Met Glu Gly Ile Met Asn
        275                 280                 285

Pro Tyr Thr Ala Leu Pro Thr Pro Gln Gln Leu Leu Ala Ile Glu Gln
290                 295                 300

Ser Val Tyr Ser Ser Asp Pro Phe Arg Gln Gly Leu Thr Pro Pro Gln
305                 310                 315                 320

Met Pro Gly Asp His Met His Pro Tyr Gly Ala Glu Pro Leu Phe His
                325                 330                 335

Asp Leu Asp Ser Asp Asp Thr Ser Leu Ser Asn Leu Gly Asp Cys Phe
            340                 345                 350

Leu Ala Thr Ser Glu Ala Gly Pro Leu Gln Ser Arg Val Gly Asn Pro
        355                 360                 365

Ile Asp His Leu Tyr Ser Met Gln Asn Ser Tyr Phe Thr Ser
370                 375                 380
```

```
<210> SEQ ID NO 16
<211> LENGTH: 457
<212> TYPE: PRT
<213> ORGANISM: Homo sapiens

<400> SEQUENCE: 16

Met Leu Gly Ala Val Lys Met Glu Gly His Glu Pro Ser Asp Trp Ser
1               5                   10                  15

Ser Tyr Tyr Ala Glu Pro Glu Gly Tyr Ser Ser Val Ser Asn Met Asn
            20                  25                  30

Ala Gly Leu Gly Met Asn Gly Met Asn Thr Tyr Met Ser Met Ser Ala
        35                  40                  45

Ala Ala Met Gly Ser Gly Ser Gly Asn Met Ser Ala Gly Ser Met Asn
50                  55                  60

Met Ser Ser Tyr Val Gly Ala Gly Met Ser Pro Ser Leu Ala Gly Met
65                  70                  75                  80

Ser Pro Gly Ala Gly Ala Met Ala Gly Met Gly Ser Ala Gly Ala
                85                  90                  95

Ala Gly Val Ala Gly Met Gly Pro His Leu Ser Pro Ser Leu Ser Pro
            100                 105                 110

Leu Gly Gly Gln Ala Ala Gly Ala Met Gly Gly Leu Ala Pro Tyr Ala
        115                 120                 125

Asn Met Asn Ser Met Ser Pro Met Tyr Gly Gln Ala Gly Leu Ser Arg
130                 135                 140

Ala Arg Asp Pro Lys Thr Tyr Arg Arg Ser Tyr Thr His Ala Lys Pro
145                 150                 155                 160

Pro Tyr Ser Tyr Ile Ser Leu Ile Thr Met Ala Ile Gln Gln Ser Pro
                165                 170                 175

Asn Lys Met Leu Thr Leu Ser Glu Ile Tyr Gln Trp Ile Met Asp Leu
            180                 185                 190

Phe Pro Phe Tyr Arg Gln Asn Gln Gln Arg Trp Gln Asn Ser Ile Arg
        195                 200                 205

His Ser Leu Ser Phe Asn Asp Cys Phe Leu Lys Val Pro Arg Ser Pro
210                 215                 220

Asp Lys Pro Gly Lys Gly Ser Phe Trp Thr Leu His Pro Asp Ser Gly
225                 230                 235                 240

Asn Met Phe Glu Asn Gly Cys Tyr Leu Arg Arg Gln Lys Arg Phe Lys
                245                 250                 255

Cys Glu Lys Gln Leu Ala Leu Lys Glu Ala Gly Ala Ala Gly Ser
            260                 265                 270

Gly Lys Lys Ala Ala Ala Gly Ala Gln Ala Ser Gln Ala Gln Leu Gly
        275                 280                 285

Glu Ala Ala Gly Pro Ala Ser Glu Thr Pro Ala Gly Thr Glu Ser Pro
290                 295                 300

His Ser Ser Ala Ser Pro Cys Gln Glu His Lys Arg Gly Gly Leu Gly
305                 310                 315                 320

Glu Leu Lys Gly Thr Pro Ala Ala Ala Leu Ser Pro Glu Pro Ala
                325                 330                 335

Pro Ser Pro Gly Gln Gln Gln Gln Ala Ala Ala His Leu Leu Gly Pro
            340                 345                 350

Pro His His Pro Gly Leu Pro Pro Glu Ala His Leu Lys Pro Glu His
        355                 360                 365

His Tyr Ala Phe Asn His Pro Phe Ser Ile Asn Asn Leu Met Ser Ser
370                 375                 380
```

```
Glu Gln Gln His His His Ser His His His Gln Pro His Lys Met
385                 390                 395                 400

Asp Leu Lys Ala Tyr Glu Gln Val Met His Tyr Pro Gly Tyr Gly Ser
                405                 410                 415

Pro Met Pro Gly Ser Leu Ala Met Gly Pro Val Thr Asn Lys Thr Gly
            420                 425                 430

Leu Asp Ala Ser Pro Leu Ala Ala Asp Thr Ser Tyr Tyr Gln Gly Val
        435                 440                 445

Tyr Ser Arg Pro Ile Met Asn Ser Ser
    450                 455

<210> SEQ ID NO 17
<211> LENGTH: 402
<212> TYPE: PRT
<213> ORGANISM: Homo sapiens

<400> SEQUENCE: 17

Met Asp Ile Ala Thr Gly Pro Glu Ser Leu Glu Arg Cys Phe Pro Arg
1               5                   10                  15

Gly Gln Thr Asp Cys Ala Lys Met Leu Asp Gly Ile Lys Met Glu Glu
            20                  25                  30

His Ala Leu Arg Pro Gly Pro Ala Thr Leu Gly Val Leu Leu Gly Ser
        35                  40                  45

Asp Cys Pro His Pro Ala Val Cys Glu Gly Cys Gln Arg Pro Ile Ser
    50                  55                  60

Asp Arg Phe Leu Met Arg Val Asn Glu Ser Ser Trp His Glu Glu Cys
65                  70                  75                  80

Leu Gln Cys Ala Ala Cys Gln Gln Ala Leu Thr Thr Ser Cys Tyr Phe
                85                  90                  95

Arg Asp Arg Lys Leu Tyr Cys Lys Gln Asp Tyr Gln Leu Phe Ala
            100                 105                 110

Ala Lys Cys Ser Gly Cys Met Glu Lys Ile Ala Pro Thr Glu Phe Val
        115                 120                 125

Met Arg Ala Leu Glu Cys Val Tyr His Leu Gly Cys Phe Cys Cys Cys
    130                 135                 140

Val Cys Glu Arg Gln Leu Arg Lys Gly Asp Glu Phe Val Leu Lys Glu
145                 150                 155                 160

Gly Gln Leu Leu Cys Lys Gly Asp Tyr Glu Lys Glu Lys Asp Leu Leu
                165                 170                 175

Ser Ser Val Ser Pro Asp Glu Ser Asp Ser Val Lys Ser Glu Asp Glu
            180                 185                 190

Asp Gly Asp Met Lys Pro Ala Lys Gly Gln Gly Ser Gln Ser Lys Gly
        195                 200                 205

Ser Gly Asp Asp Gly Lys Asp Pro Arg Arg Pro Lys Arg Pro Arg Thr
    210                 215                 220

Ile Leu Thr Thr Gln Gln Arg Arg Ala Phe Lys Ala Ser Phe Glu Val
225                 230                 235                 240

Ser Ser Lys Pro Cys Arg Lys Val Arg Glu Thr Leu Ala Ala Glu Thr
                245                 250                 255

Gly Leu Ser Val Arg Val Val Gln Val Trp Phe Gln Asn Gln Arg Ala
            260                 265                 270

Lys Met Lys Lys Leu Ala Arg Arg His Gln Gln Gln Gln Glu Gln Gln
        275                 280                 285

Asn Ser Gln Arg Leu Gly Gln Glu Val Leu Ser Ser Arg Met Glu Gly
```

```
                290                 295                 300
Met Met Ala Ser Tyr Thr Pro Leu Ala Pro Gln Gln Gln Ile Val
305                 310                 315                 320

Ala Met Glu Gln Ser Pro Tyr Gly Ser Ser Asp Pro Phe Gln Gly
                325                 330                 335

Leu Thr Pro Pro Gln Met Pro Gly Asp His Met Asn Pro Tyr Gly Asn
                340                 345                 350

Asp Ser Ile Phe His Asp Ile Asp Ser Asp Thr Ser Leu Thr Ser Leu
                355                 360                 365

Ser Asp Cys Phe Leu Gly Ser Ser Asp Val Gly Ser Leu Gln Ala Arg
                370                 375                 380

Val Gly Asn Pro Ile Asp Arg Leu Tyr Ser Met Gln Ser Ser Tyr Phe
385                 390                 395                 400

Ala Ser

<210> SEQ ID NO 18
<211> LENGTH: 598
<212> TYPE: PRT
<213> ORGANISM: Homo sapiens

<400> SEQUENCE: 18

Met Pro Cys Val Gln Ala Gln Tyr Gly Ser Ser Pro Gln Gly Ala Ser
1               5                   10                  15

Pro Ala Ser Gln Ser Tyr Ser Tyr His Ser Ser Gly Glu Tyr Ser Ser
                20                  25                  30

Asp Phe Leu Thr Pro Glu Phe Val Lys Phe Ser Met Asp Leu Thr Asn
                35                  40                  45

Thr Glu Ile Thr Ala Thr Thr Ser Leu Pro Ser Phe Ser Thr Phe Met
                50                  55                  60

Asp Asn Tyr Ser Thr Gly Tyr Asp Val Lys Pro Pro Cys Leu Tyr Gln
65                  70                  75                  80

Met Pro Leu Ser Gly Gln Gln Ser Ser Ile Lys Val Glu Asp Ile Gln
                85                  90                  95

Met His Asn Tyr Gln Gln His Ser His Leu Pro Pro Gln Ser Glu Glu
                100                 105                 110

Met Met Pro His Ser Gly Ser Val Tyr Tyr Lys Pro Ser Ser Pro Pro
                115                 120                 125

Thr Pro Thr Thr Pro Gly Phe Gln Val Gln His Ser Pro Met Trp Asp
                130                 135                 140

Asp Pro Gly Ser Leu His Asn Phe His Gln Asn Tyr Val Ala Thr Thr
145                 150                 155                 160

His Met Ile Glu Gln Arg Lys Thr Pro Val Ser Arg Leu Ser Leu Phe
                165                 170                 175

Ser Phe Lys Gln Ser Pro Pro Gly Thr Pro Val Ser Ser Cys Gln Met
                180                 185                 190

Arg Phe Asp Gly Pro Leu His Val Pro Met Asn Pro Glu Pro Ala Gly
                195                 200                 205

Ser His His Val Val Asp Gly Gln Thr Phe Ala Val Pro Asn Pro Ile
                210                 215                 220

Arg Lys Pro Ala Ser Met Gly Phe Pro Gly Leu Gln Ile Gly His Ala
225                 230                 235                 240

Ser Gln Leu Leu Asp Thr Gln Val Pro Ser Pro Ser Arg Gly Ser
                245                 250                 255

Pro Ser Asn Glu Gly Leu Cys Ala Val Cys Gly Asp Asn Ala Ala Cys
```

```
                260                 265                 270
Gln His Tyr Gly Val Arg Thr Cys Glu Gly Cys Lys Gly Phe Phe Lys
            275                 280                 285

Arg Thr Val Gln Lys Asn Ala Lys Tyr Val Cys Leu Ala Asn Lys Asn
290                 295                 300

Cys Pro Val Asp Lys Arg Arg Arg Asn Arg Cys Gln Tyr Cys Arg Phe
305                 310                 315                 320

Gln Lys Cys Leu Ala Val Gly Met Val Lys Glu Val Val Arg Thr Asp
                325                 330                 335

Ser Leu Lys Gly Arg Arg Gly Arg Leu Pro Ser Lys Pro Lys Ser Pro
            340                 345                 350

Gln Glu Pro Ser Pro Ser Pro Val Ser Leu Ile Ser Ala Leu
            355                 360                 365

Val Arg Ala His Val Asp Ser Asn Pro Ala Met Thr Ser Leu Asp Tyr
            370                 375                 380

Ser Arg Phe Gln Ala Asn Pro Asp Tyr Gln Met Ser Gly Asp Asp Thr
385                 390                 395                 400

Gln His Ile Gln Gln Phe Tyr Asp Leu Leu Thr Gly Ser Met Glu Ile
                405                 410                 415

Ile Arg Gly Trp Ala Glu Lys Ile Pro Gly Phe Ala Asp Leu Pro Lys
            420                 425                 430

Ala Asp Gln Asp Leu Leu Phe Glu Ser Ala Phe Leu Glu Leu Phe Val
            435                 440                 445

Leu Arg Leu Ala Tyr Arg Ser Asn Pro Val Glu Gly Lys Leu Ile Phe
450                 455                 460

Cys Asn Gly Val Val Leu His Arg Leu Gln Cys Val Arg Gly Phe Gly
465                 470                 475                 480

Glu Trp Ile Asp Ser Ile Val Glu Phe Ser Ser Asn Leu Gln Asn Met
                485                 490                 495

Asn Ile Asp Ile Ser Ala Phe Ser Cys Ile Ala Ala Leu Ala Met Val
            500                 505                 510

Thr Glu Arg His Gly Leu Lys Glu Pro Lys Arg Val Glu Glu Leu Gln
            515                 520                 525

Asn Lys Ile Val Asn Cys Leu Lys Asp His Val Thr Phe Asn Asn Gly
            530                 535                 540

Gly Leu Asn Arg Pro Asn Tyr Leu Ser Lys Leu Leu Gly Lys Leu Pro
545                 550                 555                 560

Glu Leu Arg Thr Leu Cys Thr Gln Gly Leu Gln Arg Ile Phe Tyr Leu
                565                 570                 575

Lys Leu Glu Asp Leu Val Pro Pro Ala Ile Ile Asp Lys Leu Phe
            580                 585                 590

Leu Asp Thr Leu Pro Phe
        595

<210> SEQ ID NO 19
<211> LENGTH: 480
<212> TYPE: PRT
<213> ORGANISM: Homo sapiens

<400> SEQUENCE: 19

Met Asn Ala Ser Glu Phe Arg Arg Arg Gly Lys Glu Met Val Asp Tyr
1               5                   10                  15

Met Ala Asn Tyr Met Glu Gly Ile Glu Gly Arg Gln Val Tyr Pro Asp
            20                  25                  30
```

```
Val Glu Pro Gly Tyr Leu Arg Pro Leu Ile Pro Ala Ala Ala Pro Gln
         35                  40                  45

Glu Pro Asp Thr Phe Glu Asp Ile Ile Asn Asp Val Glu Lys Ile Ile
 50                  55                  60

Met Pro Gly Val Thr His Trp His Ser Pro Tyr Phe Phe Ala Tyr Phe
 65                  70                  75                  80

Pro Thr Ala Ser Ser Tyr Pro Ala Met Leu Ala Asp Met Leu Cys Gly
                 85                  90                  95

Ala Ile Gly Cys Ile Gly Phe Ser Trp Ala Ala Ser Pro Ala Cys Thr
                100                 105                 110

Glu Leu Glu Thr Val Met Met Asp Trp Leu Gly Lys Met Leu Glu Leu
            115                 120                 125

Pro Lys Ala Phe Leu Asn Glu Lys Ala Gly Glu Gly Gly Val Ile
130                 135                 140

Gln Gly Ser Ala Ser Glu Ala Thr Leu Val Ala Leu Leu Ala Ala Arg
145                 150                 155                 160

Thr Lys Val Ile His Arg Leu Gln Ala Ala Ser Pro Glu Leu Thr Gln
                165                 170                 175

Ala Ala Ile Met Glu Lys Leu Val Ala Tyr Ser Ser Asp Gln Ala His
                180                 185                 190

Ser Ser Val Glu Arg Ala Gly Leu Ile Gly Gly Val Lys Leu Lys Ala
            195                 200                 205

Ile Pro Ser Asp Gly Asn Phe Ala Met Arg Ala Ser Ala Leu Gln Glu
                210                 215                 220

Ala Leu Glu Arg Asp Lys Ala Ala Gly Leu Ile Pro Phe Phe Met Val
225                 230                 235                 240

Ala Thr Leu Gly Thr Thr Thr Cys Cys Ser Phe Asp Asn Leu Leu Glu
                245                 250                 255

Val Gly Pro Ile Cys Asn Lys Glu Asp Ile Trp Leu His Val Asp Ala
            260                 265                 270

Ala Tyr Ala Gly Ser Ala Phe Ile Cys Pro Glu Phe Arg His Leu Leu
                275                 280                 285

Asn Gly Val Glu Phe Ala Asp Ser Phe Asn Phe Asn Pro His Lys Trp
            290                 295                 300

Leu Leu Val Asn Phe Asp Cys Ser Ala Met Trp Val Lys Lys Arg Thr
305                 310                 315                 320

Asp Leu Thr Gly Ala Phe Arg Leu Asp Pro Thr Tyr Leu Lys His Ser
                325                 330                 335

His Gln Asp Ser Gly Leu Ile Thr Asp Tyr Arg His Trp Gln Ile Pro
                340                 345                 350

Leu Gly Arg Arg Phe Arg Ser Leu Lys Met Trp Phe Val Phe Arg Met
            355                 360                 365

Tyr Gly Val Lys Gly Leu Gln Ala Tyr Ile Arg Lys His Val Gln Leu
370                 375                 380

Ser His Glu Phe Glu Ser Leu Val Arg Gln Asp Pro Arg Phe Glu Ile
385                 390                 395                 400

Cys Val Glu Val Ile Leu Gly Leu Val Cys Phe Arg Leu Lys Gly Ser
                405                 410                 415

Asn Lys Val Asn Glu Ala Leu Leu Gln Arg Ile Asn Ser Ala Lys Lys
                420                 425                 430

Ile His Leu Val Pro Cys His Leu Arg Asp Lys Phe Val Leu Arg Phe
                435                 440                 445

Ala Ile Cys Ser Arg Thr Val Glu Ser Ala His Val Gln Arg Ala Trp
```

```
                    450                 455                 460
Glu His Ile Lys Glu Leu Ala Ala Asp Val Leu Arg Ala Glu Arg Glu
465                 470                 475                 480

<210> SEQ ID NO 20
<211> LENGTH: 392
<212> TYPE: PRT
<213> ORGANISM: Homo sapiens

<400> SEQUENCE: 20

Met Glu Glu Gln Gln Pro Glu Pro Lys Ser Gln Arg Asp Ser Ala Leu
1               5                   10                  15

Gly Ala Ala Ala Ala Thr Pro Gly Gly Leu Ser Leu Ser Leu Ser
                20                  25                  30

Pro Gly Ala Ser Gly Ser Ser Gly Ser Gly Ser Asp Gly Asp Ser Val
            35                  40                  45

Pro Val Ser Pro Gln Pro Ala Pro Ser Pro Pro Ala Ala Pro Cys
50                  55                  60

Leu Pro Pro Leu Ala His Pro His Leu Pro Pro His Pro Pro Pro
65                  70                  75                  80

Pro Pro Pro Gln His Leu Ala Ala Pro Ala His Gln Pro Gln Pro Ala
                85                  90                  95

Ala Gln Leu His Arg Thr Thr Asn Phe Phe Ile Asp Asn Ile Leu Arg
            100                 105                 110

Pro Asp Phe Gly Cys Lys Lys Glu Gln Pro Pro Gln Leu Leu Val
            115                 120                 125

Ala Ala Ala Arg Gly Gly Ala Gly Gly Gly Arg Val Glu Arg
130                 135                 140

Asp Arg Gly Gln Thr Ala Ala Gly Arg Asp Pro Val His Pro Leu Gly
145                 150                 155                 160

Thr Arg Ala Pro Gly Ala Ala Ser Leu Leu Cys Ala Pro Asp Ala Asn
                165                 170                 175

Cys Gly Pro Pro Asp Gly Ser Gln Pro Ala Ala Gly Ala Gly Ala
            180                 185                 190

Ser Lys Ala Gly Asn Pro Ala Ala Ala Ala Ala Ala Ala Ala
            195                 200                 205

Val Ala Ala Ala Ala Ala Ala Ala Lys Pro Ser Asp Thr Gly
210                 215                 220

Gly Gly Gly Ser Gly Gly Gly Ala Gly Ser Pro Gly Ala Gln Gly Thr
225                 230                 235                 240

Lys Tyr Pro Glu His Gly Asn Pro Ala Ile Leu Leu Met Gly Ser Ala
                245                 250                 255

Asn Gly Gly Pro Val Val Lys Thr Asp Ser Gln Gln Pro Leu Val Trp
            260                 265                 270

Pro Ala Trp Val Tyr Cys Thr Arg Tyr Ser Asp Arg Pro Ser Ser Gly
            275                 280                 285

Pro Arg Thr Arg Lys Leu Lys Lys Lys Asn Glu Lys Glu Asp Lys
290                 295                 300

Arg Pro Arg Thr Ala Phe Thr Ala Glu Gln Leu Gln Arg Leu Lys Ala
305                 310                 315                 320

Glu Phe Gln Ala Asn Arg Tyr Ile Thr Glu Gln Arg Arg Gln Thr Leu
                325                 330                 335

Ala Gln Glu Leu Ser Leu Asn Glu Ser Gln Ile Lys Ile Trp Phe Gln
            340                 345                 350
```

```
Asn Lys Arg Ala Lys Ile Lys Lys Ala Thr Gly Ile Lys Asn Gly Leu
        355                 360                 365

Ala Leu His Leu Met Ala Gln Gly Leu Tyr Asn His Ser Thr Thr Thr
        370                 375                 380

Val Gln Asp Lys Asp Glu Ser Glu
385                 390
```